(12) United States Patent
Pietras et al.

(10) Patent No.: US 9,266,901 B2
(45) Date of Patent: Feb. 23, 2016

(54) COMPOSITIONS AND METHODS FOR TREATING CANCER

(71) Applicant: The Regents of the University of California, Oakland, CA (US)

(72) Inventors: Richard J. Pietras, Sherman Oaks, CA (US); Michael E. Jung, Los Angeles, CA (US); Diana C. Marquez-Garban, Los Angeles, CA (US); Gang Deng, Los Angeles, CA (US)

(73) Assignee: The Regents of The University of Califronia, Oakland, CA (US)

( * ) Notice: Subject to any disclaimer, the term of this patent is extended or adjusted under 35 U.S.C. 154(b) by 0 days.

(21) Appl. No.: 14/505,288

(22) Filed: Oct. 2, 2014

(65) Prior Publication Data

US 2015/0031725 A1    Jan. 29, 2015

Related U.S. Application Data

(63) Continuation of application No. PCT/US2013/035010, filed on Apr. 2, 2013.

(60) Provisional application No. 61/619,289, filed on Apr. 2, 2012.

(51) Int. Cl.
| | | |
|---|---|---|
| *C07D 307/00* | (2006.01) | |
| *C07D 493/04* | (2006.01) | |
| *A61K 45/06* | (2006.01) | |
| *A61K 31/365* | (2006.01) | |
| *A61K 31/443* | (2006.01) | |
| *A61K 31/4525* | (2006.01) | |

(52) U.S. Cl.
CPC ............ *C07D 493/04* (2013.01); *A61K 31/365* (2013.01); *A61K 31/443* (2013.01); *A61K 31/4525* (2013.01); *A61K 45/06* (2013.01)

(58) Field of Classification Search
CPC ..................................................... C07D 493/04
USPC ............................................................ 549/299
See application file for complete search history.

(56) References Cited

U.S. PATENT DOCUMENTS

| | | | |
|---|---|---|---|
| 6,890,946 B2 | 5/2005 | Nakshatri et al. | |
| 7,312,242 B2 | 12/2007 | Crooks et al. | |
| 7,678,904 B2 * | 3/2010 | Crooks ............... | C07D 307/77 544/153 |
| 8,124,652 B2 | 2/2012 | Crooks et al. | |
| 2002/0058077 A1 | 5/2002 | Shen et al. | |
| 2004/0229936 A1 | 11/2004 | Hsieh et al. | |
| 2010/0009970 A1 | 1/2010 | Johansen et al. | |

FOREIGN PATENT DOCUMENTS

WO    WO-2005/007103 A2    1/2005

OTHER PUBLICATIONS

Nasim Bioorganic & Medicinal Chemistry Letters 18 (2008) 3870-3873.*
Neukirch, Bioorganic & Medicinal Chemistry (2003), 11(7),1503-1510.*
Hwang et al., "Synthesis and anti-viral activity of a series of sesquiterpene lactones and analogues in the subgenomic HCV replicon system." Bioorg Med. Chemistry, 13:83-91 (2006).
Neelakantan et al., "Aminoparthenolides as novel anti-leukemic agents: Discovery of the NF-kappaB inhibitor, DMAPT (LC-1)." Bioorg. Med. Chem. Letters. 19:4346-4349 (2009).

* cited by examiner

*Primary Examiner* — Nizal Chandrakumar
(74) *Attorney, Agent, or Firm* — Mintz, Levin, Cohn, Ferris, Glovsky and Popeo, P.C.

(57) ABSTRACT

Provided herein, inter alia, are compositions and methods useful for treating hyperproliferative diseases, including cancer and non-malignant hyperproliferative diseases.

3 Claims, 16 Drawing Sheets

COMPOSITIONS AND METHODS FOR TREATING CANCER

CROSS-REFERENCES TO RELATED APPLICATIONS

This application is a continuation application of international PCT application No. PCT/US2013/035010, filed Apr. 2, 2013, which claims the benefit of U.S. Provisional Patent Application No. 61/619,289, filed Apr. 2, 2012, which are incorporated herein by reference in their entirety and for all purposes.

STATEMENT AS TO RIGHTS TO INVENTIONS MADE UNDER FEDERALLY SPONSORED RESEARCH AND DEVELOPMENT

This invention was made with Government support under DAMD17-03-1-0381, awarded by the U.S. Army, Medical Research and Materiel Command. The Government has certain rights in the invention.

BACKGROUND

Lung Cancer is the leading cause of cancer death in women and men in the U.S. It is estimated that there will be more than 230,000 patients diagnosed with lung cancer this year, with more than 160,000 deaths, and non-small cell lung cancer (NSCLC) will account for more than three quarters of these cases (1). Survival rates of NSCLC, the predominant type of lung cancer are unacceptably low, and new approaches to treat and prevent this disease are urgently needed. Feverfew extracts and parthenolide show anticancer activity in NSCLC in vitro, while parthenolides modified to enhance solubility also show significant anticancer activity in vivo in NSCLC models. This anticancer effect may be associated with the ability of these substances to inhibit the nuclear transcription factor kappaB (NFκB) possibly leading in turn to the promotion of tumor cell apoptosis (3). Disclosed herein is a study of the role of feverfew extract and parthenolide in the treatment and prevention of NSCLC.

At diagnosis, about 70% of breast cancer patients have tumors that express estrogen receptors (ER) and/or progesterone receptors (PR). Patients with ER+ tumors can be treated with hormonal therapy such as tamoxifen which was the first effective targeted therapy for breast cancer. However, all advanced ER+ tumors eventually develop endocrine resistance, and there is an urgent need for new interventions to stop endocrine resistance. Mechanisms of endocrine resistance include HER2 overexpression (occurs in 15-20% of patients) and increased activation of NFκB signaling pathways. Activation of tumor NFκB occurs in ER+ breast cancers with resistance to hormonal therapy and in HER2+ breast tumors with resistance to Trastuzumab (Herceptin). Parthenolide analogues that block activation of NFκB are active in restoring breast tumor responses to hormonal and Trastuzumab therapies, thereby potentially helping to improve patient outcomes Tuberous sclerosis complex (TSC) is an autosomal dominant disorder with development of hamartomatous lesions in many organs (71-74). Some lesions grow progressively and require clinical intervention. TSC is due to mutations in either TSC1 or TSC2 genes. TSC1 (hamartin)/TSC2 (tuberin) protein complexes serve a critical role in negatively regulating mTOR complex 1 (mTORC1) which exerts downstream effects on cell transcription, translation, metabolism and proliferation. mTORC1 is constitutively active in cells lacking either TSC1 or TSC2 and in hamartomas of TSC patients. TSC can occur in association with pulmonary lymphangioleiomyomatosis (LAM), a progressive and often fatal interstitial lung disease that occurs largely in women and is characterized by proliferation of abnormal smooth muscle cells. TSC2-null smooth muscle cells in angiomyolipomas (AML) are very similar to those of pulmonary LAM, and data suggest LAM may be the result of benign cell metastases. Rapamycin and related drugs (everolimus) which bind and inhibit mTORC1 have clinical activity for therapy of TSC, including renal AML and pulmonary LAM (72). However, rapamycin does not elicit complete TSC regression in most cases, and termination of therapy oft leads to lesion re-growth. New therapeutic approaches to control the growth of TSC-related proliferative diseases are urgently needed.

The poor prognosis of advanced non-small cell lung cancer (NSCLC) is due, in part, to emergence of tumor resistance to chemotherapy (1). Recent data indicate that human tumors contain a small subset of cancer stem cells (CSC) responsible for drug resistance and tumor maintenance (2-5). If such minute subsets of CSC drive tumor formation and drug resistance, therapies targeting the bulk tumor mass but not CSC will fail. Since it is hypothesized that CSC are responsible for tumor regeneration after chemo-therapy (6), we performed preliminary studies to determine if drug treatment could enrich for CSCs. Treatment of human lung tumor NSCLC cell lines (A549, H23) with increasing doses of cisplatin resulted in selection of drug-resistant cells (DRC)(6). Using Fluorescence Activated Cell Sorting (FACS), DRC were selected for expression of cell surface CD133+ and cytosolic ALDH1 by Aldefluor assay (7, 8), yielding cell subsets amounting to 2%-5% of bulk tumor cell populations of H23 and A549, respectively. Furthermore, CSC-like cells grew as tumor spheres, maintained self-renewal capacity and differentiated, with differentiated progenitors losing CD133 expression and acquiring drug sensitivity. These initial studies suggest that chemotherapy leads to propagation of CSC. Importantly, resistance of CSC-like cells to cisplatin was fully reversed by treatment with parthenolide (PTL). The antitumor effect of PTL has been reported to selectively kill CSCs through inhibition of nuclear factor-KB (NF-κB) which is markedly activated by chemotherapy (9).

The aromatic plant known as feverfew (*Tanacetum parthenium*) has been used in folk medicine to treat a number of different human maladies. The plant is notably rich in a family of compounds known as sesquiterpene lactones, particularly parthenolide. One of the most important characteristics of parthenolide is its antitumor activity, with reports of cytotoxic activity against epidermoid carcinoma, fibrosarcoma, hepatocellular carcinoma, breast and prostate cancer, and leukemia and lymphoma cells. This compound has been demonstrated in vitro to inhibit different type of cancer cells (2, 4, 5). Parthenolide may promote apoptosis in neoplastic cells in part by inhibiting the cancer-promoting factor, NFκB, a critical regulator of genes involved in tumor cell proliferation, antiapoptosis (anti-cell death), DNA damage responses and angiogenesis (2, 4, 6, 7). Inhibition of NFκB signaling leads to reduced expression of many proteins including antiapoptotic proteins. The downstream consequences of these effects lead to cell cycle arrest and cell death (2, 8). Unfortunately, both feverfew herbal extract and native parthenolide have limited in vivo activity due to poor bioavailability (9). Hence, the inventors have developed improved derivatives of these naturally-ocurring compounds to be used as drug-like agents to treat and prevent lung cancer and other human malignancies.

Breast cancer is a worldwide health concern with about 1,000,000 million new cases each year. In the clinic, endocrine therapy is an important intervention in women with breast cancers that express estrogen receptor (ER), and treatment with tamoxifen has enhanced patient survival. The success of endocrine therapy is dependent on tight regulation of breast cell growth by steroids and growth factor receptors (27) most patients eventually stop responding to antiestrogen therapy. Resistance to tamoxifen (TAM) and aromatase inhibitors represents a major drawback to treatment of hormone-dependent breast cancer, and new options for endocrine therapy are urgently needed to reverse this outcome. Emerging data now confirm the existence of previously-unsuspected interactions between growth factor and estrogen signaling pathways that contribute to growth regulation in breast cancers. Targeting this signaling axis may promote introduction of more effective and less toxic antihormone treatments for human breast cancers (28-30).

Subversion of growth factor receptors often occurs in malignancy, and members of the HER family are often implicated in cancer (31). EGF receptor (EGFR), a 170-kD transmembrane protein, has an extracellular ligand-binding domain, a membrane-spanning region and a cytoplasmic EGF-stimulated tyrosine kinase. On EGF binding, EGFR undergoes dimerization and autophosphorylation on tyrosine residues. This results in activation of downstream protein kinases, such as MAP kinase and PI3 kinase/Akt kinase, and subsequent stimulation of transcription factors. The HER family includes other receptor tyrosine kinases including HER-2, a 185-kD kinase encoded by HER-2/neu oncogene, as well as HER-3 and HER-4. HER-2 receptor functions similar to EGFR (30-33), and, on binding of ligand to EGF, HER-3 or HER-4, HER-2 is often recruited as a preferred partner to form heterodimers that activate downstream signaling for growth and survival. Overexpression of HER-2 or related HER receptors occurs in two-thirds of sporadic breast tumors, while HER-2 over-expression/amplification is found in 25-30% of breast cancers (32, 33). Overexpression of HER-2 is generally a marker of poor prognosis (7), and it associates with failure of antiestrogen therapy in the clinic (28, 34-38).

It is generally held that biologic activity of estrogen in breast cells is mediated by its binding with high-affinity ER in the nucleus (27, 39) (see FIG. 10).

Upon estrogen binding, ER undergoes an activating conformational change that allows association with coactivators and target genes, thus promoting regulation of gene transcription. Ligand-bound ER in the nucleus functions as a transcription factor. Blocking estrogen binding to ER is the basis of the action of tamoxifen, a partial agonist that limits proliferative effects of estrogen in breast, while fulvestrant (Faslodex) is a new generation antiestrogen with a mechanism of action leading to downregulation of ER in tumors (42, 43). In addition to nuclear actions of estrogens, numerous reports document rapid effects of estradiol mediated by a membrane-associated ER that derives from the same transcript as nuclear ER (34-46) (FIG. 10). Interactions between ER and growth factor receptors occur in lipid rafts, assemblies of cholesterol and sphingolipids in plasma membrane (47). Caveolae are specialized rafts present in most cells (48, 49), but they are markedly reduced or absent in breast cancer cells (50). Caveolae and lipid rafts are enriched in growth factor receptors, including HER-2 receptors (48), and a portion of ER also localize in caveolae and lipid rafts (51, 52).

Conversion of estrogen-sensitive to -resistant tumors after the start of antiestrogen therapy is a major problem in the clinic (65). This resistance may be due, in part, to enhanced growth factor signaling, a cellular response to antiestrogen treatment that eventually results in increased phosphorylation of ER and/or coactivators, such as AIB1(54). Convergence between growth factor and estrogen signaling may elicit a synergistic feed-forward circuit with more robust cell growth (FIG. 10). It is notable that tumors with HER-2 overexpression tend to respond poorly to antiestrogens (69-72). A meta-analysis of 7 clinical trials indicated that breast tumors with HER-2 overexpression were resistant to tamoxifen (73-75). Such clinical data offer further evidence of the biologic interaction between HER-2 and ER. To evaluate the relation of HER-2 to clinical antiestrogen resistance, we used estrogen-responsive, MCF-7 cells with defined levels of ER that were transfected with HER-2 gene (MCF-7/HER-2). MCF-7 cells+HER-2 overexpression and parent MCF-7 cells were grown as xenografts in nude mice as before (28) (FIG. 11). As expected, growth of parent cells was markedly suppressed by tamoxifen and by fulvestrant (FIG. 11). In contrast, MCF-7/HER-2 cells were insensitive to tamoxifen, but retained partial sensitivity to fulvestrant (28). This correlates with data from the clinic suggesting tamoxifen resistance in breast tumors with high levels of HER-2 expression.

Two important systems that transmit extracellular signals into the machinery of the cell nucleus are the signaling pathways that activate nuclear factor KB (NF-κB) and estrogen receptor (ER). These two transcription factors induce expression of genes that control cell fates, including proliferation and cell death (apoptosis). Estrogen receptor (ER) and nuclear factor-kappaB (NFκB), a major regulator of pathways central to malignant progression, are known to be mutually inhibitory at several molecular levels. It has been suggested that in some ER-positive breast cancers SERMS such as tamoxifen can activate NFκB, stimulate cell growth and survival, and thereby contribute to endocrine resistance (62). Recent investigations elucidated a previously unsuspected effect of ER, namely inhibition of NFκB activation. In breast cancer, antiestrogen therapy might cause reactivation of NFκB, potentially re-routing a proliferative signal to breast cancer cells and contributing to hormone resistance (63). Thus, ligands that selectively block NFκB activation, such as parthenolides, could provide specific potential therapy for hormone-resistant ER-positive breast cancers (see FIG. 12). Disclosed herein, inter alia, are solutions to these and other problems in the art.

BRIEF SUMMARY OF THE INVENTION

In a first aspect is provided a compound, or a pharmaceutically acceptable salt thereof, wherein the compound has a formula selected from the group consisting of:

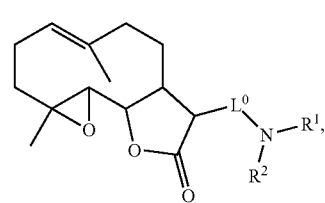

(I)

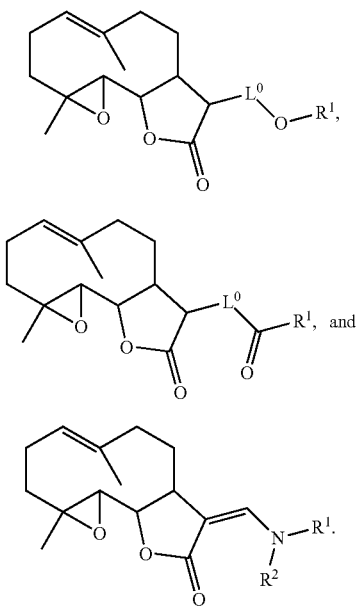

L⁰ is independently a bond or an unsubstituted $C_1$-$C_{10}$ alkylene. $R^1$ and $R^2$ are independently hydrogen, —OH, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; where $R^1$ and $R^2$ may optionally be joined to form a substituted or unsubstituted heterocycloalkyl or a substituted or unsubstituted heteroaryl; with the proviso that the compound, or the pharmaceutically acceptable salt thereof is

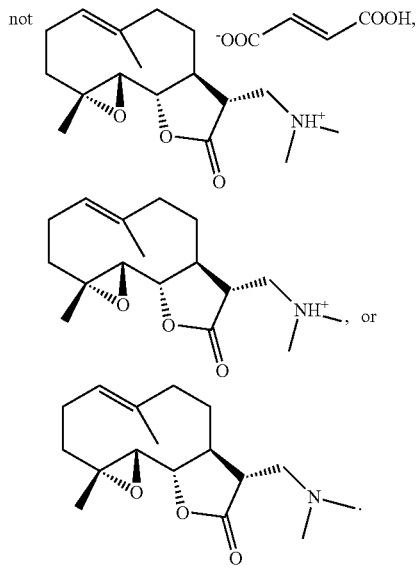

In another aspect is provided a pharmaceutical composition including a pharmaceutically acceptable excipient and a compound, or a pharmaceutically acceptable salt thereof, as described herein (including embodiments).

In another aspect is provided a method of treating cancer in a patient in need of the treatment, the method including administering a therapeutically effective amount of a compound, or a pharmaceutically acceptable salt thereof, as described herein (including embodiments) to the patient.

In another aspect is provided a method of treating a non-malignant hyperproliferative disease in a patient in need of the treatment, the method including administering a therapeutically effective amount of a compound, or a pharmaceutically acceptable salt thereof, as described herein (including embodiments) to the patient.

In another aspect is provided a method of inhibiting cancer cell growth or survival including contacting the cell with an effective amount of a compound, or a pharmaceutically acceptable salt thereof, as described herein (including embodiments).

In another aspect is provided a method of modulating the level of activity of NF-κB in a cell including contacting the cell with an effective amount of a compound, or a pharmaceutically acceptable salt thereof, as described herein (including embodiments).

In another aspect is provided a method of modulating the level of activity of TSC1 in a cell including contacting the cell with an effective amount of a compound, or a pharmaceutically acceptable salt thereof, as described herein (including embodiments).

In another aspect is provided a method of modulating the level of activity of TSC2 in a cell including contacting the cell with an effective amount of a compound, or a pharmaceutically acceptable salt thereof, as described herein (including embodiments).

In another aspect is provided a method of modulating the level of activity of mTOR in a cell including contacting the cell with an effective amount of a compound, or a pharmaceutically acceptable salt thereof, as described herein (including embodiments).

DETAILED DESCRIPTION

I. Definitions

Figure 1:
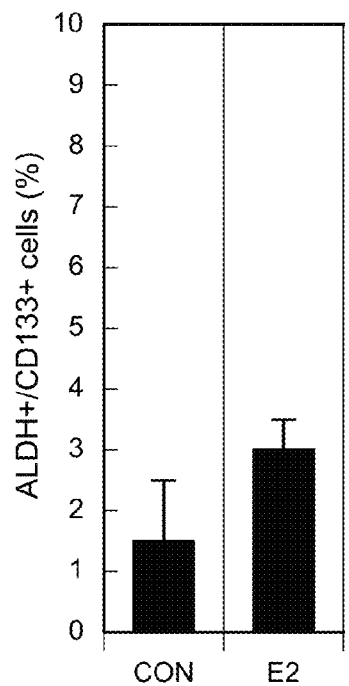
FIG. 1. Isolation of cancer stem/progenitor cell subsets as determined by assay of specific biomarkers, ALDH and CD133, and effect of estrogen exposure. NSCLC cells (A549) were treated in vitro with control (CON), 10 nM estradiol-17b (E2), or E2 in the presence of 1 mM fulvestrant. Thereafter, aldehyde dehydrogenase (ALDH) activity and CD133 expression were analyzed by established double labeling methods using an Aldefluor Assay Kit and CD133 antibody, respectively, followed by FACS sorting [11]. The numbers of ALDH+/CD133+ lung tumor cells, representing a putative CSC subset, was expressed as a percent of total lung tumor cells for each treatment group. Therapy with estrogen increases the proportion of cancer stem/progenitor cell subsets as determined by assay of specific biomarkers, ALDH and CD133 (*P<0.001). Experiments were done in triplicate.

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., —CH$_2$O— is equivalent to —OCH$_2$—.

The term "alkyl," by itself or as part of another substituent, means, unless otherwise stated, a straight (i.e., unbranched) or branched carbon chain (or carbon), or combination thereof, which may be fully saturated, mono- or polyunsaturated and can include di- and multivalent radicals, having the number of carbon atoms designated (i.e., $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, (cyclohexyl) methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—).

The term "alkylene," by itself or as part of another substituent, means, unless otherwise stated, a divalent radical derived from an alkyl, as exemplified, but not limited by, —CH$_2$CH$_2$CH$_2$CH$_2$—. Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms. The term "alkenylene," by itself or as part of another substituent, means, unless otherwise stated, a divalent radical derived from an alkene.

The term "heteroalkyl," by itself or in combination with another term, means, unless otherwise stated, a stable straight or branched chain, or combinations thereof, including at least one carbon atom and at least one heteroatom selected from the group consisting of O, N, P, Si, and S, and wherein the nitrogen and sulfur atoms may optionally be oxidized, and the nitrogen heteroatom may optionally be quaternized. The heteroatom(s) O, N, P, S, and Si may be placed at any interior position of the heteroalkyl group or at the position at which the alkyl group is attached to the remainder of the molecule. Examples include, but are not limited to: —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, —CH=CH—N(CH$_3$)—CH$_3$, —O—CH$_3$, —O—CH$_2$—CH$_3$, and —CN. Up to two or three heteroatoms may be consecutive, such as, for example, —CH$_2$—NH—OCH$_3$ and —CH$_2$—O—Si(CH$_3$)$_3$.

Similarly, the term "heteroalkylene," by itself or as part of another substituent, means, unless otherwise stated, a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—. As described above, heteroalkyl groups, as used herein, include those groups that are attached to the remainder of the molecule through a heteroatom, such as —C(O)R', —C(O)NR', —NR'R", —OR', —SR', and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl," by themselves or in combination with other terms, mean, unless otherwise stated, cyclic versions of "alkyl" and "heteroalkyl," respectively, wherein the carbons making up the ring or rings do not necessarily need to be bonded to a hydrogen due to all carbon valencies participating in bonds with non-hydrogen atoms. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively.

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo($C_1$-$C_4$)alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring. The term "heteroaryl" refers to aryl groups (or rings) that contain at least one heteroatom such as N, O, or S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively. Non-limiting examples of heteroaryl groups include pyridinyl, pyrimidinyl, thiophenyl, thienyl, furanyl, indolyl, benzoxadiazolyl, benzodioxolyl, benzodioxanyl, thianaphthanyl, pyrrolopyridinyl, indazolyl, quinolinyl, quinoxalinyl, pyridopyrazinyl, quinazolinonyl, benzoisoxazolyl, imidazopyridinyl, benzofuranyl, benzothienyl, benzothiophenyl, phenyl, naphthyl, biphenyl, pyrrolyl, pyrazolyl, imidazolyl, pyrazinyl, oxazolyl, isoxazolyl, thiazolyl, furylthienyl, pyridyl, pyrimidyl, benzothiazolyl, purinyl, benzimidazolyl, isoquinolyl, thiadiazolyl, oxadiazolyl, pyrrolyl, diazolyl, triazolyl, tetrazolyl, benzothiadiazolyl, isothiazolyl, pyrazolopyrimidinyl, pyrrolopyrimidinyl, benzotriazolyl, benzoxazolyl, or quinolyl. The examples above may be substituted or unsubstituted and divalent radicals of each heteroaryl example above are non-limiting examples of heteroarylene.

A fused ring heterocyloalkyl-aryl is an aryl fused to a heterocycloalkyl. A fused ring heterocycloalkyl-heteroaryl is a heteroaryl fused to a heterocycloalkyl. A fused ring heterocycloalkyl-cycloalkyl is a heterocycloalkyl fused to a cycloalkyl. A fused ring heterocycloalkyl-heterocycloalkyl is a heterocycloalkyl fused to another heterocycloalkyl. Fused ring heterocycloalkyl-aryl, fused ring heterocycloalkyl-heteroaryl, fused ring heterocycloalkyl-cycloalkyl, or fused ring heterocycloalkyl-heterocycloalkyl may each independently be unsubstituted or substituted with one or more of the substitutents described herein.

The term "oxo," as used herein, means an oxygen that is double bonded to a carbon atom.

The term "alkylsulfonyl," as used herein, means a moiety having the formula —S($O_2$)—R', where R' is a substituted or unsubstituted alkyl group as defined above. R' may have a specified number of carbons (e.g., "$C_1$-$C_4$ alkylsulfonyl").

Each of the above terms (e.g., "alkyl," "heteroalkyl," "aryl," and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SR', -halogen, —SiR'R"R'", —OC(O)R', —C(O)R', —$CO_2$R', —CONR"R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —NR'NR"R'", —ONR'R", —NR'C=(O)NR"NR'"R"", —CN, —$NO_2$, monophosphate (or derivatives thereof), diphosphate (or derivatives thereof), triphosphate (or derivatives thereof), in a number ranging from zero to (2m'+1), where m' is the total number of carbon atoms in such radical. R, R', R", R'", and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted heteroaryl, substituted or unsubstituted alkyl, alkoxy, or thioalkoxy groups, or arylalkyl groups. When a compound of the invention includes more than one R group, for example, each of the R groups is independently selected as are each R', R", R'", and R"" group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are varied and are selected from, for example: —OR', —NR'R", —SR', -halogen, —SiR'R"R''', —OC(O)R', —C(O)R', —CO$_2$R', —CONR'R", —OC(O)NR'R", —NR"C(O)R', —NR'—C(O)NR"R''', —NR"C(O)$_2$R', —NR—C(NR'R"R''')=NR"", —NR—C(NR'R")=NR''', —S(O)R', —S(O)$_2$R', —S(O)$_2$NR'R", —NRSO$_2$R', —NR'NR"R''', —ONR'R", —NR'C=(O)NR"NR'''R"", —CN, —NO$_2$, —R', —N$_3$, —CH(Ph)$_2$, fluoro(C$_1$-C$_4$)alkoxy, and fluoro(C$_1$-C$_4$)alkyl, in a number ranging from zero to the total number of open valences on the aromatic ring system; and where R', R", R''', and R"" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound of the invention includes more than one R group, for example, each of the R groups is independently selected as are each R', R", R''', and R"" groups when more than one of these groups is present.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula -T-C(O)—(CRR')$_q$—U—, wherein T and U are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'—, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X'—(C"R"R''')$_d$—, where s and d are independently integers of from 0 to 3, and X' is —O—, —NR'—, —S—, —S(O)—, —S(O)$_2$—, or —S(O)$_2$NR'—. The substituents R, R', R", and R''' are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include, oxygen (O), nitrogen (N), sulfur (S), phosphorus (P), and silicon (Si).

A "substituent group," as used herein, means a group selected from the following moieties:

(A) oxo, halogen, —CF$_3$, —CCl$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl, and (B) alkyl, heteroalkyl, cycloalkyl, heterocycloalkyl, aryl, heteroaryl, substituted with at least one substituent selected from:

(i) oxo, halogen, —CF$_3$, —CCl$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl, and (ii) alkyl, heteroalkyl, cycloalkyl, heterocycloalkyl, aryl, heteroaryl, substituted with at least one substituent selected from:

(a) oxo, halogen, —CF$_3$, —CCl$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl, and (b) alkyl, heteroalkyl, cycloalkyl, heterocycloalkyl, aryl, heteroaryl, substituted with at least one substituent selected from: oxo, halogen, —CF$_3$, —CCl$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl.

A "size-limited substituent" or "size-limited substituent group," as used herein, means a group selected from all of the substituents described above for a "substituent group," wherein each substituted or unsubstituted alkyl is a substituted or unsubstituted C$_1$-C$_{20}$ alkyl, each substituted or unsubstituted heteroalkyl is a substituted or unsubstituted 2 to 20 membered heteroalkyl, each substituted or unsubstituted cycloalkyl is a substituted or unsubstituted C$_3$-C$_8$ cycloalkyl, each substituted or unsubstituted heterocycloalkyl is a substituted or unsubstituted 3 to 8 membered heterocycloalkyl, each substituted or unsubstituted aryl is a substituted or unsubstituted C$_6$-C$_{10}$ aryl, and each substituted or unsubstituted heteroaryl is a substituted or unsubstituted 5 to 10 membered heteroaryl.

A "lower substituent" or "lower substituent group," as used herein, means a group selected from all of the substituents described above for a "substituent group," wherein each substituted or unsubstituted alkyl is a substituted or unsubstituted C$_1$-C$_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 9 membered heteroaryl.

In some embodiments, each substituted group described in the compounds herein is substituted with at least one substituent group. More specifically, in some embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In other embodiments, at least one or all of these groups are substituted with at least one size-limited substituent group. In other embodiments, at least one or all of these groups are substituted with at least one lower substituent group.

In other embodiments of the compounds herein, each substituted or unsubstituted alkyl may be a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 10 membered heteroaryl. In some embodiments of the compounds herein, each substituted or unsubstituted alkylene is a substituted or unsubstituted $C_1$-$C_{20}$ alkylene, each substituted or unsubstituted heteroalkylene is a substituted or unsubstituted 2 to 20 membered heteroalkylene, each substituted or unsubstituted cycloalkylene is a substituted or unsubstituted $C_3$-$C_8$ cycloalkylene, each substituted or unsubstituted heterocycloalkylene is a substituted or unsubstituted 3 to 8 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 10 membered heteroarylene.

In some embodiments, each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 9 membered heteroaryl. In some embodiments, each substituted or unsubstituted alkylene is a substituted or unsubstituted $C_1$-$C_8$ alkylene, each substituted or unsubstituted heteroalkylene is a substituted or unsubstituted 2 to 8 membered heteroalkylene, each substituted or unsubstituted cycloalkylene is a substituted or unsubstituted $C_3$-$C_7$ cycloalkylene, each substituted or unsubstituted heterocycloalkylene is a substituted or unsubstituted 3 to 7 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 9 membered heteroarylene. In some embodiments, the compound is a chemical species set forth in the Examples section below.

The term "pharmaceutically acceptable salts" is meant to include salts of the active compounds that are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, e.g., Berge et al., *Journal of Pharmaceutical Science* 66:1-19 (1977)). Certain specific compounds of the present invention contain both basic and acidic functionalities that allow the compounds to be converted into either base or acid addition salts. Other pharmaceutically acceptable carriers known to those of skill in the art are suitable for the present invention. Salts tend to be more soluble in aqueous or other protonic solvents that are the corresponding free base forms. In other cases, the preparation may be a lyophilized powder in 1 mM-50 mM histidine, 0.1%-2% sucrose, 2%-7% mannitol at a pH range of 4.5 to 5.5, that is combined with buffer prior to use.

Thus, the compounds of the present invention may exist as salts, such as with pharmaceutically acceptable acids. The present invention includes such salts. Examples of such salts include hydrochlorides, hydrobromides, sulfates, methanesulfonates, nitrates, maleates, acetates, citrates, fumarates, tartrates (e.g., (+)-tartrates, (−)-tartrates, or mixtures thereof including racemic mixtures), succinates, benzoates, and salts with amino acids such as glutamic acid. These salts may be prepared by methods known to those skilled in the art.

The neutral forms of the compounds are preferably regenerated by contacting the salt with a base or acid and isolating the parent compound in the conventional manner. The parent form of the compound differs from the various salt forms in certain physical properties, such as solubility in polar solvents.

In addition to salt forms, the present invention provides compounds, which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

As used herein, the term "salt" refers to acid or base salts of the compounds used in the methods of the present invention. Illustrative examples of acceptable salts are mineral acid (hydrochloric acid, hydrobromic acid, phosphoric acid, and the like) salts, organic acid (acetic acid, propionic acid, glutamic acid, citric acid and the like) salts, quaternary ammonium (methyl iodide, ethyl iodide, and the like) salts.

Certain compounds of the present invention possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present invention. The compounds of the present invention do not include those which are known in art to be too unstable to synthesize and/or isolate. The present invention is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another.

It will be apparent to one skilled in the art that certain compounds of this invention may exist in tautomeric forms, all such tautomeric forms of the compounds being within the scope of the invention.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}C$- or $^{14}C$-enriched carbon are within the scope of this invention.

The compounds of the present invention may also contain unnatural proportions of atomic isotopes at one or more of the atoms that constitute such compounds. For example, the compounds may be radiolabeled with radioactive isotopes, such as for example tritium ($^3H$), iodine-125 ($^{125}I$), or carbon-14 ($^{14}C$). All isotopic variations of the compounds of the present invention, whether radioactive or not, are encompassed within the scope of the present invention.

The symbol "~~" denotes the point of attachment of a chemical moiety to the remainder of a molecule or chemical formula.

The terms "a" or "an," as used in herein means one or more. In addition, the phrase "substituted with a[n]," as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls. Moreover, where a moiety is substituted with an R substituent, the group may be referred to as "R-substituted." Where a moiety is R-substituted, the moiety is substituted with at least one R substituent and each R substituent is optionally different.

Descriptions of compounds of the present invention are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

The terms "treating" or "treatment" refers to any indicia of success in the treatment or amelioration of an injury, disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation. For example, certain methods herein treat hyperproliferative disorders, such as cancer (e.g. leukemia, lung cancer, epidermoid carcinoma (i.e. squamous-cell carcinoma), fibrosarcoma, liver cancer (e.g. hepatocellular carcinoma), prostate cancer, kidney cancer (e.g. renal cell carcinoma or urothelial cell carcinoma), lymphoma, breast cancer, urinary bladder cancer, prostate cancer, or therapy resistant cancer) or non-malignant hyperproliferative diseases (e.g. hamartomatous lesion, angiomyolipoma, lymphangioleiomyomatosis, tuberous sclerosis complex, a hamartia, or a hamartoma). For example certain methods herein treat cancer by decreasing or reducing or preventing the occurrence, growth, metastasis, or progression of cancer or by decreasing or reducing or preventing a symptom of cancer. Symptoms of cancer (e.g. leukemia, lung cancer, epidermoid carcinoma (i.e. squamous-cell carcinoma), fibrosarcoma, liver cancer (e.g. hepatocellular carcinoma), prostate cancer, kidney cancer (e.g. renal cell carcinoma or urothelial cell carcinoma), lymphoma, breast cancer, urinary bladder cancer, prostate cancer, or therapy resistant cancer) would be known or may be determined by a person of ordinary skill in the art. The term "treating" and conjugations thereof, include prevention of an injury, pathology, condition, or disease (e.g. preventing the development of one or more symptoms of cancer (e.g. leukemia, lung cancer, epidermoid carcinoma (i.e. squamous-cell carcinoma), fibrosarcoma, liver cancer (e.g. hepatocellular carcinoma), prostate cancer, kidney cancer (e.g. renal cell carcinoma or urothelial cell carcinoma), lymphoma, breast cancer, urinary bladder cancer, prostate cancer, or therapy resistant cancer).

An "effective amount" is an amount sufficient to accomplish a stated purpose (e.g. achieve the effect for which it is administered, treat a disease, reduce enzyme activity, increase enzyme activity, reduce one or more symptoms of a disease or condition). An example of an "effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom(s). A "prophylactically effective amount" of a drug is an amount of a drug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. An "activity decreasing amount," as used herein, refers to an amount of antagonist (inhibitor) required to decrease the activity of an enzyme or protein relative to the absence of the antagonist. An "activity increasing amount," as used herein, refers to an amount of agonist (activator) required to increase the activity of an enzyme or protein relative to the absence of the agonist. A "function disrupting amount," as used herein, refers to the amount of antagonist (inhibitor) required to disrupt the function of an enzyme or protein relative to the absence of the antagonist. A "function increasing amount," as used herein, refers to the amount of agonist (activator) required to increase the function of an enzyme or protein relative to the absence of the agonist. The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and Remington: *The Science and Practice of Pharmacy,* 20th Edition, 2003, Gennaro, Ed., Lippincott, Williams & Wilkins).

The term "associated" or "associated with" in the context of a substance or substance activity or function associated with a disease (e.g. cancer (e.g. leukemia, lung cancer, epidermoid carcinoma (i.e. squamous-cell carcinoma), fibrosarcoma, liver cancer (e.g. hepatocellular carcinoma), prostate cancer, kidney cancer (e.g. renal cell carcinoma or urothelial cell carcinoma), lymphoma, breast cancer, urinary bladder cancer, prostate cancer, or therapy resistant cancer) means that the disease (e.g. cancer (e.g. leukemia, lung cancer, epidermoid carcinoma (i.e. squamous-cell carcinoma), fibrosarcoma, liver cancer (e.g. hepatocellular carcinoma), prostate cancer, kidney cancer (e.g. renal cell carcinoma or urothelial cell carcinoma), lymphoma, breast cancer, urinary bladder cancer, prostate cancer, or therapy resistant cancer)) is caused by (in whole or in part), or a symptom of the disease is caused by (in whole or in part) the substance or substance activity or function. For example, a symptom of a disease or condition associated with an increase in NFκB activity may be a symptom that results (entirely or partially) from an increase in NFκB activity (e.g. increase in NFκB phosphorylation or activity of phosphorylated NFκB or activity of NFκB or increase in activity of an NFκB signal transduction or signaling pathway). As used herein, what is described as being associated with a disease, if a causative agent, could be a target for treatment of the disease. For example, a disease associated with increased NFκB activity or NFκB pathway activity (e.g. phosphorylated NFκB activity or pathway), may be treated with an agent (e.g. compound as described herein) effective for decreasing the level of activity of NFκB activity or NFκB pathway or phosphorylated NFκB activity or pathway. For example, a disease associated with phosphorylated NFκB, may be treated with an agent (e.g. compound as described herein) effective for decreasing the level of activity of phosphorylated NFκB or a downstream component or effector of phosphorylated NFκB. For example, a disease associated with NFκB, may be treated with an agent (e.g. compound as described herein) effective for decreasing the level of activity of NFκB or a downstream component or effector of NFκB.

"Control" or "control experiment" is used in accordance with its plain ordinary meaning and refers to an experiment in which the subjects or reagents of the experiment are treated as in a parallel experiment except for omission of a procedure, reagent, or variable of the experiment. In some instances, the control is used as a standard of comparison in evaluating experimental effects.

"Contacting" is used in accordance with its plain ordinary meaning and refers to the process of allowing at least two distinct species (e.g. chemical compounds including biomolecules, or cells) to become sufficiently proximal to react, interact or physically touch. It should be appreciated, however, that the resulting reaction product can be produced directly from a reaction between the added reagents or from an intermediate from one or more of the added reagents which can be produced in the reaction mixture. The term "contacting" may include allowing two species to react, interact, or physically touch, wherein the two species may be a compound as described herein and a protein or enzyme (e.g. NFκB, phosphorylated NFκB, mTOR, mTORC1, TSC1, TSC2 or component of NFκB pathway, phosphorylated NFκB pathway, pathway activated by NFκB phosphorylation, mTOR pathway, mTORC1 pathway, TSC1 pathway, or TSC2 pathway). In some embodiments contacting includes allowing a compound described herein to interact with a protein or enzyme that is involved in a signaling pathway (e.g. NFκB pathway, phosphorylated NFκB pathway, pathway activated by NFκB phosphorylation, mTOR pathway, mTORC1 pathway, TSC1 pathway, or TSC2 pathway).

As defined herein, the term "inhibition", "inhibit", "inhibiting" and the like in reference to a protein-inhibitor (e.g. antagonist) interaction means negatively affecting (e.g. decreasing) the activity or function of the protein relative to the activity or function of the protein in the absence of the inhibitor. In some embodiments inhibition refers to reduction of a disease or symptoms of disease. In some embodiments, inhibition refers to a reduction in the activity of a signal transduction pathway or signaling pathway. Thus, inhibition includes, at least in part, partially or totally blocking stimulation, decreasing, preventing, or delaying activation, or inactivating, desensitizing, or down-regulating signal transduction or enzymatic activity or the amount of a protein. In some embodiments, inhibition refers to a decrease in the activity of a signal transduction pathway or signaling pathway (e.g. NFκB or phosphorylated NFκB or NFκB pathway or phosphorylated NFκB pathway or pathway activated by NFκB phosphorylation or mTOR pathway or mTOR or mTORC1 pathway or mTORC1 or TSC1 or TSC1 pathway or TSC2 or TSC2 pathway). Thus, inhibition may include, at least in part, partially or totally decreasing stimulation, decreasing or reducing activation, or inactivating, desensitizing, or down-regulating signal transduction or enzymatic activity or the amount of a protein increased in a disease (e.g. level of NFκB activity or protein or level of phosphorylated NFκB or level or activity of a component of an NFκB pathway or level of phosphorylated NFκB activity or protein or level or activity of a component of a phosphorylated NFκB pathway or mTOR pathway or mTOR or mTORC1 pathway or mTORC1 or TSC1 or TSC1 pathway or TSC2 or TSC2 pathway, wherein each is associated with a hyperproliferative disease, for example cancer (e.g. leukemia, lung cancer, epidermoid carcinoma (i.e. squamous-cell carcinoma), fibrosarcoma, liver cancer (e.g. hepatocellular carcinoma), prostate cancer, kidney cancer (e.g. renal cell carcinoma or urothelial cell carcinoma), lymphoma, breast cancer, urinary bladder cancer, prostate cancer, or therapy resistant cancer) or a non-malignant hyperproliferative disease (e.g. hamartomatous lesion, angiomyolipoma, lymphangioleiomyomatosis, tuberous sclerosis complex, a hamartia, or a hamartoma). Inhibition may include, at least in part, partially or totally decreasing stimulation, decreasing or reducing activation, or deactivating, desensitizing, or down-regulating signal transduction or enzymatic activity or the amount of a protein (e.g. NFκB or phosphorylated NFκB or NFκB pathway or phosphorylated NFκB pathway or pathway activated by NFκB phosphorylation or mTOR pathway or mTOR or mTORC1 pathway or mTORC1 or TSC1 or TSC1 pathway or TSC2 or TSC2 pathway) that may modulate the level of another protein or increase cell survival (e.g. decrease in phosphorylated NFκB pathway activity may increase cell survival in cells that may or may not have an increase in phosphorylated NFκB pathway activity relative to a non-disease control or decrease in NFκB pathway activity may increase cell survival in cells that may or may not have an increase in NFκB pathway activity relative to a non-disease control).

As defined herein, the term "activation", "activate", "activating" and the like in reference to a protein-activator (e.g. agonist) interaction means positively affecting (e.g. increasing) the activity or function of the protein (e.g. NFκB or phosphorylated NFκB or NFκB pathway or phosphorylated NFκB pathway or pathway activated by NFκB phosphorylation or mTOR pathway or mTOR or mTORC1 pathway or mTORC1 or TSC1 or TSC1 pathway or TSC2 or TSC2 pathway) relative to the activity or function of the protein in the absence of the activator (e.g. compound described herein). In some embodiments, activation refers to an increase in the activity of a signal transduction pathway or signaling pathway (e.g. NFκB pathway or phosphorylated NFκB pathway or pathway activated by NFκB phosphorylation or mTOR pathway or mTORC1 pathway or TSC1 pathway or TSC2 pathway). Thus, activation may include, at least in part, partially or totally increasing stimulation, increasing or enabling activation, or activating, sensitizing, or up-regulating signal transduction or enzymatic activity or the amount of a protein decreased in a disease (e.g. level of NFκB activity or level of protein or activity decreased by phosphorylation of NFκB or protein associated with cancer (e.g. leukemia, lung cancer, epidermoid carcinoma (i.e. squamous-cell carcinoma), fibrosarcoma, liver cancer (e.g. hepatocellular carcinoma), prostate cancer, kidney cancer (e.g. renal cell carcinoma or urothelial cell carcinoma), lymphoma, breast cancer, urinary bladder cancer, prostate cancer, or therapy resistant cancer). Activation may include, at least in part, partially or totally increasing stimulation, increasing or enabling activation, or activating, sensitizing, or up-regulating signal transduction or enzymatic activity or the amount of a protein (e.g. NFκB or phosphorylated NFκB or NFκB pathway or phosphorylated NFκB pathway or pathway activated by NFκB phosphorylation or mTOR pathway or mTOR or mTORC1 pathway or mTORC1 or TSC1 or TSC1 pathway or TSC2 or TSC2 pathway) that may modulate the level of another protein or increase cell survival (e.g. increase in NFκB activity may increase cell survival in cells that may or may not have a reduction in NFκB activity relative to a non-disease control).

The term "modulator" refers to a composition that increases or decreases the level of a target molecule or the function of a target molecule. In some embodiments, a modulator of NFκB or phosphorylated NFκB or NFκB pathway or phosphorylated NFκB pathway or pathway activated by NFκB phosphorylation or mTOR pathway or mTOR or mTORC1 pathway or mTORC1 or TSC1 or TSC1 pathway or TSC2 or TSC2 pathway is a compound that reduces the severity of one or more symptoms of a disease associated with NFκB or phosphorylated NFκB or NFκB pathway or phosphorylated NFκB pathway or pathway activated by NFκB phosphorylation or mTOR pathway or mTOR or mTORC1 pathway or mTORC1 or TSC1 or TSC1 pathway or TSC2 or TSC2 pathway (e.g. disease associated with an increase or decrease in the level of NFκB or phosphorylated NFκB or NFκB pathway or phosphorylated NFκB pathway or pathway activated by NFκB phosphorylation or mTOR pathway or mTOR or mTORC1 pathway or mTORC1 or TSC1 or TSC1 pathway or TSC2 or TSC2 pathway, for example cancer (e.g. leukemia, lung cancer, epidermoid carcinoma (i.e. squamous-cell carcinoma), fibrosarcoma, liver cancer (e.g. hepatocellular carcinoma), prostate cancer, kidney cancer (e.g. renal cell carcinoma or urothelial cell carcinoma), lymphoma, breast cancer, urinary bladder cancer, prostate cancer, or therapy resistant cancer) or a non-malignant hyperproliferative disease (e.g. hamartomatous lesion, angiomyolipoma, lymphangioleiomyomatosis, tuberous sclerosis complex, a hamartia, or a hamartoma) or a disease that is not caused by NFκB or phosphorylated NFκB or NFκB pathway or phosphorylated NFκB pathway or pathway activated by NFκB phosphorylation or mTOR pathway or mTOR or mTORC1 pathway or mTORC1 or TSC1 or TSC1 pathway or TSC2 or TSC2 pathway but may benefit from modulation of NFκB or phosphorylated NFκB or NFκB pathway or phosphorylated NFκB pathway or pathway activated by NFκB phosphorylation or mTOR pathway or mTOR or mTORC1 pathway or mTORC1 or TSC1 or TSC1 pathway or TSC2 or TSC2 pathway activity (e.g. decreasing or increasing in level or level of activity of NFκB or phosphorylated NFκB or NFκB pathway or phosphorylated NFκB pathway or pathway activated by NFκB phosphorylation or mTOR pathway or mTOR or mTORC1 pathway or mTORC1 or TSC1 or TSC1 pathway or TSC2 or TSC2 pathway). In embodiments, a modulator of NFκB or phosphorylated NFκB or NFκB pathway or phosphorylated NFκB pathway or pathway activated by NFκB phosphorylation or mTOR pathway or mTOR or mTORC1 pathway or mTORC1 or TSC1 or TSC1 pathway or TSC2 or TSC2 pathway is an anti-cancer agent.

"Patient" or "subject in need thereof" refers to a living organism suffering from or prone to a disease or condition that can be treated by administration of a compound or pharmaceutical composition, as provided herein. Non-limiting examples include humans, other mammals, bovines, rats, mice, dogs, monkeys, goat, sheep, cows, deer, and other non-mammalian animals. In some embodiments, a patient is human.

"Disease" or "condition" refer to a state of being or health status of a patient or subject capable of being treated with a compound, pharmaceutical composition, or method provided herein. In some embodiments, the disease is a disease related to (e.g. caused by) an increase in the level of activity or amount of NFκB or phosphorylated NFκB or NFκB pathway or phosphorylated NFκB pathway or pathway activated by NFκB phosphorylation or mTOR pathway or mTOR or mTORC1 pathway or mTORC1 or TSC1 or TSC1 pathway or TSC2 or TSC2 pathway. In some embodiments, the disease is a disease related to (e.g. caused by) a decrease in the level of activity or amount of NFκB or phosphorylated NFκB or NFκB pathway or phosphorylated NFκB pathway or pathway activated by NFκB phosphorylation or mTOR pathway or mTOR or mTORC1 pathway or mTORC1 or TSC1 or TSC1 pathway or TSC2 or TSC2 pathway. In some embodiments, the disease is cancer (e.g. leukemia, lung cancer, epidermoid carcinoma (i.e. squamous-cell carcinoma), fibrosarcoma, liver cancer (e.g. hepatocellular carcinoma), prostate cancer, kidney cancer (e.g. renal cell carcinoma or urothelial cell carcinoma), lymphoma, breast cancer, urinary bladder cancer, prostate cancer, or therapy resistant cancer). In some embodiments, the disease is a non-malignant hyperproliferative disease (e.g. hamartomatous lesion, angiomyolipoma, lymphangioleiomyomatosis, tuberous sclerosis complex, a hamartia, or a hamartoma), Examples of diseases, disorders, or conditions include, but are not limited to, cancer (e.g. leukemia, lung cancer, epidermoid carcinoma (i.e. squamous-cell carcinoma), fibrosarcoma, liver cancer (e.g. hepatocellular carcinoma), prostate cancer, kidney cancer (e.g. renal cell carcinoma or urothelial cell carcinoma), lymphoma, breast cancer, urinary bladder cancer, prostate cancer, or therapy resistant cancer). In some instances, "disease" or "condition" refers to cancer. In some further instances, "cancer" refers to human cancers and carcinomas, sarcomas, adenocarcinomas, lymphomas, leukemias, melanomas, etc., including solid and lymphoid cancers, kidney, breast, lung, bladder, colon, ovarian, prostate, pancreas, stomach, brain, head and neck, skin, uterine, testicular, glioma, esophagus, liver cancer, including hepatocarcinoma, lymphoma, including B-acute lymphoblastic lymphoma, non-Hodgkin's lymphomas (e.g., Burkitt's, Small Cell, and Large Cell lymphomas), Hodgkin's lymphoma, leukemia (including AML, ALL, and CML), and/or multiple myeloma. In some further instances, "cancer" refers to lung cancer, breast cancer, ovarian cancer, leukemia, lymphoma, melanoma, pancreatic cancer, sarcoma, bladder cancer, bone cancer, brain cancer, cervical cancer, colon cancer, esophageal cancer, gastric cancer, liver cancer, head and neck cancer, kidney cancer, myeloma, thyroid cancer, prostate cancer, metastatic cancer, or carcinoma. In embodiments "cancer" refers to a cancer resistant to an anti-cancer therapy (e.g. treatment with an anti-cancer agent (e.g. platinum-based compound, cisplatin, carboplatin, hormonal therapy, hormonal therapeutic agent, tamoxifen, trastuzumab, or an aromatase inhibitor)).

As used herein, the term "cancer" refers to all types of cancer, neoplasm or malignant tumors found in mammals, including leukemia, lymphoma, carcinomas and sarcomas. Exemplary cancers that may be treated with a compound, pharmaceutical composition, or method provided herein include lymphoma, sarcoma, bladder cancer, bone cancer, brain tumor, cervical cancer, colon cancer, esophageal cancer, gastric cancer, head and neck cancer, kidney cancer, myeloma, thyroid cancer, leukemia, prostate cancer, breast cancer (e.g. ER positive, ER negative, chemotherapy resistant, herceptin resistant, HER2 positive, doxorubicin resistant, tamoxifen resistant, ductal carcinoma, lobular carcinoma, primary, metastatic), ovarian cancer, pancreatic cancer, liver cancer (e.g. hepatocellular carcinoma), lung cancer (e.g. non-small cell lung carcinoma, squamous cell lung carcinoma, adenocarcinoma, large cell lung carcinoma, small cell lung carcinoma, carcinoid, sarcoma, cisplatin resistant lung cancer, carboplatin resistant lung cancer, platinum-based compound resistant lung cancer), glioblastoma multiforme, glioma, or melanoma. Additional examples include, cancer of the thyroid, endocrine system, brain, breast, cervix, colon, head & neck, liver, kidney, lung, non-small cell lung, melanoma, mesothelioma, ovary, sarcoma, stomach, uterus or Medulloblastoma, Hodgkin's Disease, Non-Hodgkin's Lymphoma, multiple myeloma, neuroblastoma, glioma, glioblastoma multiforme, ovarian cancer, rhabdomyosarcoma, primary thrombocytosis, primary macroglobulinemia, primary brain tumors, cancer, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, endometrial cancer, adrenal cortical cancer, neoplasms of the endocrine or exocrine pancreas, medullary thyroid cancer, medullary thyroid carcinoma, melanoma, colorectal cancer, papillary thyroid cancer, hepatocellular carcinoma, Paget's Disease of the Nipple, Phyllodes Tumors, Lobular Carcinoma, Ductal Carcinoma, cancer of the pancreatic stellate cells, cancer of the hepatic stellate cells, or prostate cancer.

The term "leukemia" refers broadly to progressive, malignant diseases of the blood-forming organs and is generally characterized by a distorted proliferation and development of leukocytes and their precursors in the blood and bone marrow. Leukemia is generally clinically classified on the basis of (1) the duration and character of the disease-acute or chronic; (2) the type of cell involved; myeloid (myelogenous), lymphoid (lymphogenous), or monocytic; and (3) the increase or non-increase in the number abnormal cells in the blood-leukemic or aleukemic (subleukemic). Exemplary leukemias that may be treated with a compound, pharmaceutical composition, or method provided herein include, for example, acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, multiple myeloma, plasmacytic leukemia, promyelocytic leukemia, Rieder cell leukemia, Schilling's leukemia, stem cell leukemia, subleukemic leukemia, or undifferentiated cell leukemia.

The term "sarcoma" generally refers to a tumor which is made up of a substance like the embryonic connective tissue and is generally composed of closely packed cells embedded in a fibrillar or homogeneous substance. Sarcomas that may be treated with a compound, pharmaceutical composition, or method provided herein include a chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, or telangiectaltic sarcoma.

The term "melanoma" is taken to mean a tumor arising from the melanocytic system of the skin and other organs. Melanomas that may be treated with a compound, pharmaceutical composition, or method provided herein include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma, subungal melanoma, or superficial spreading melanoma.

The term "carcinoma" refers to a malignant new growth made up of epithelial cells tending to infiltrate the surrounding tissues and give rise to metastases. Exemplary carcinomas that may be treated with a compound, pharmaceutical composition, or method provided herein include, for example, medullary thyroid carcinoma, familial medullary thyroid carcinoma, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, ductal carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatiniformi carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypernephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lobular carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tubular carcinoma, tuberous carcinoma, verrucous carcinoma, or carcinoma villosum.

The term "non-malignant hyperproliferative disease" is used in accordance with its plain ordinary meaning and refers to a disease including a growth that is not cancerous. Examples of a non-malignant hyperproliferative disease include a hamartomatous lesion, angiomyolipoma, lymphangioleiomyomatosis, tuberous sclerosis complex, a hamartia, or a hamartoma.

The term "signaling pathway" as used herein refers to a series of interactions between cellular and optionally extracellular components (e.g. proteins, nucleic acids, small molecules, ions, lipids) that conveys a change in one component to one or more other components, which in turn may convey a change to additional components, which is optionally propagated to other signaling pathway components.

"Pharmaceutically acceptable excipient" and "pharmaceutically acceptable carrier" refer to a substance that aids the administration of an active agent to and absorption by a subject and can be included in the compositions of the present invention without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethycellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention. One of skill in the art will recognize that other pharmaceutical excipients are useful in the present invention.

The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

As used herein, the term "administering" means oral administration, administration as a suppository, topical contact, intravenous, parenteral, intraperitoneal, intramuscular, intralesional, intrathecal, intracranial, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc. By "co-administer" it is meant that a composition described herein is administered at the same time, just prior to, or just after the administration of one or more additional therapies (e.g. anti-cancer agent or chemotherapeutic). The compound of the invention can be administered alone or can be co-administered to the patient. Co-administration is meant to include simultaneous or sequential administration of the compound individually or in combination (more than one compound or agent). Thus, the preparations can also be combined, when desired, with other active substances (e.g. to reduce metabolic degradation). The compositions of the present invention can be delivered by transdermally, by a topical route, formulated as applicator sticks, solutions, suspensions, emulsions, gels, creams, ointments, pastes, jellies, paints, powders, and aerosols. Oral preparations include tablets, pills, powder, dragees, capsules, liquids, lozenges, cachets, gels, syrups, slurries, suspensions, etc., suitable for ingestion by the patient. Solid form preparations include powders, tablets, pills, capsules, cachets, suppositories, and dispersible granules. Liquid form preparations include solutions, suspensions, and emulsions, for example, water or water/propylene glycol solutions. The compositions of the present invention may additionally include components to provide sustained release and/or comfort. Such components include high molecular weight, anionic mucomimetic polymers, gelling polysaccharides and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes. The compositions of the present invention can also be delivered as microspheres for slow release in the body. For example, microspheres can be administered via intradermal injection of drug-containing microspheres, which slowly release subcutaneously (see Rao, *J. Biomater Sci. Polym. Ed.* 7:623-645, 1995; as biodegradable and injectable gel formulations (see, e.g., Gao *Pharm. Res.* 12:857-863, 1995); or, as microspheres for oral administration (see, e.g., Eyles, *J. Pharm. Pharmacol.* 49:669-674, 1997). In another embodiment, the formulations of the compositions of the present invention can be delivered by the use of liposomes which fuse with the cellular membrane or are endocytosed, i.e., by employing receptor ligands attached to the liposome, that bind to surface membrane protein receptors of the cell resulting in endocytosis. By using liposomes, particularly where the liposome surface carries receptor ligands specific for target cells, or are otherwise preferentially directed to a specific organ, one can focus the delivery of the compositions of the present invention into the target cells in vivo. (See, e.g., Al-Muhammed, *J. Microencapsul.* 13:293-306, 1996; Chonn, *Curr. Opin. Biotechnol.* 6:698-708, 1995; Ostro, *Am. J. Hosp. Pharm.* 46:1576-1587, 1989). The compositions of the present invention can also be delivered as nanoparticles.

Pharmaceutical compositions provided by the present invention include compositions wherein the active ingredient (e.g. compounds described herein, including embodiments or examples) is contained in a therapeutically effective amount, i.e., in an amount effective to achieve its intended purpose. The actual amount effective for a particular application will depend, inter alia, on the condition being treated. When administered in methods to treat a disease, such compositions will contain an amount of active ingredient effective to achieve the desired result, e.g., modulating the activity of a target molecule (e.g. NFκB, phosphorylated NFκB, mTOR, mTORC1, TSC1, TSC2 or component of NFκB pathway, phosphorylated NFκB pathway, pathway activated by NFκB phosphorylation, mTOR pathway, mTORC1 pathway, TSC1 pathway, or TSC2 pathway), and/or reducing, eliminating, or slowing the progression of disease symptoms (e.g. symptoms of cancer (e.g. leukemia, lung cancer, epidermoid carcinoma (i.e. squamous-cell carcinoma), fibrosarcoma, liver cancer (e.g. hepatocellular carcinoma), prostate cancer, kidney cancer (e.g. renal cell carcinoma or urothelial cell carcinoma), lymphoma, breast cancer, urinary bladder cancer, prostate cancer, or therapy resistant cancer) or a non-malignant hyperproliferative disease (e.g. hamartomatous lesion, angiomyolipoma, lymphangioleiomyomatosis, tuberous sclerosis complex, a hamartia, or a hamartoma)). Determination of a therapeutically effective amount of a compound of the invention is well within the capabilities of those skilled in the art, especially in light of the detailed disclosure herein.

The dosage and frequency (single or multiple doses) administered to a mammal can vary depending upon a variety of factors, for example, whether the mammal suffers from another disease, and its route of administration; size, age, sex, health, body weight, body mass index, and diet of the recipient; nature and extent of symptoms of the disease being treated (e.g. symptoms of cancer (e.g. leukemia, lung cancer, epidermoid carcinoma (i.e. squamous-cell carcinoma), fibrosarcoma, liver cancer (e.g. hepatocellular carcinoma), prostate cancer, kidney cancer (e.g. renal cell carcinoma or urothelial cell carcinoma), lymphoma, breast cancer, urinary bladder cancer, prostate cancer, or therapy resistant cancer) or a non-malignant hyperproliferative disease (e.g. hamartomatous lesion, angiomyolipoma, lymphangioleiomyomatosis, tuberous sclerosis complex, a hamartia, or a hamartoma)), kind of concurrent treatment, complications from the disease being treated or other health-related problems. Other therapeutic regimens or agents can be used in conjunction with the methods and compounds of Applicants' invention. Adjustment and manipulation of established dosages (e.g., frequency and duration) are well within the ability of those skilled in the art.

For any compound described herein, the therapeutically effective amount can be initially determined from cell culture assays. Target concentrations will be those concentrations of active compound(s) that are capable of achieving the methods described herein, as measured using the methods described herein or known in the art.

As is well known in the art, therapeutically effective amounts for use in humans can also be determined from animal models. For example, a dose for humans can be formulated to achieve a concentration that has been found to be effective in animals. The dosage in humans can be adjusted by monitoring compounds effectiveness and adjusting the dosage upwards or downwards, as described above. Adjusting the dose to achieve maximal efficacy in humans based on the methods described above and other methods is well within the capabilities of the ordinarily skilled artisan.

Dosages may be varied depending upon the requirements of the patient and the compound being employed. The dose administered to a patient, in the context of the present invention should be sufficient to effect a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached.

Dosage amounts and intervals can be adjusted individually to provide levels of the administered compound effective for the particular clinical indication being treated. This will provide a therapeutic regimen that is commensurate with the severity of the individual's disease state.

Utilizing the teachings provided herein, an effective prophylactic or therapeutic treatment regimen can be planned that does not cause substantial toxicity and yet is effective to treat the clinical symptoms demonstrated by the particular patient. This planning should involve the careful choice of active compound by considering factors such as compound potency, relative bioavailability, patient body weight, presence and severity of adverse side effects, preferred mode of administration and the toxicity profile of the selected agent.

The compounds described herein can be used in combination with one another, with other active agents known to be useful in treating cancer (e.g. leukemia, lung cancer, epidermoid carcinoma (i.e. squamous-cell carcinoma), fibrosarcoma, liver cancer (e.g. hepatocellular carcinoma), prostate cancer, kidney cancer (e.g. renal cell carcinoma or urothelial cell carcinoma), lymphoma, breast cancer, urinary bladder cancer, prostate cancer, or therapy resistant cancer) or a non-malignant hyperproliferative disease (e.g. hamartomatous lesion, angiomyolipoma, lymphangioleiomyomatosis, tuberous sclerosis complex, a hamartia, or a hamartoma), or with adjunctive agents that may not be effective alone, but may contribute to the efficacy of the active agent.

In some embodiments, co-administration includes administering one active agent within 0.5, 1, 2, 4, 6, 8, 10, 12, 16, 20, or 24 hours of a second active agent. Co-administration includes administering two active agents simultaneously, approximately simultaneously (e.g., within about 1, 5, 10, 15, 20, or 30 minutes of each other), or sequentially in any order. In some embodiments, co-administration can be accomplished by co-formulation, i.e., preparing a single pharmaceutical composition including both active agents. In other embodiments, the active agents can be formulated separately. In another embodiment, the active and/or adjunctive agents may be linked or conjugated to one another. In some embodiments, the compounds described herein may be combined with treatments for cancer (e.g. leukemia, lung cancer, epidermoid carcinoma (i.e. squamous-cell carcinoma), fibrosarcoma, liver cancer (e.g. hepatocellular carcinoma), prostate cancer, kidney cancer (e.g. renal cell carcinoma or urothelial cell carcinoma), lymphoma, breast cancer, urinary bladder cancer, prostate cancer, or therapy resistant cancer) or non-malignant hyperproliferative diseases (e.g. hamartomatous lesion, angiomyolipoma, lymphangioleiomyomatosis, tuberous sclerosis complex, a hamartia, or a hamartoma) such as surgery.

The term "NFκB" or "NF-κB" refers to a protein complex controlling DNA transcription commonly referred to in the art as "nuclear factor kappa-light-chain-enhancer of activated B cells" including individual proteins thereof and homologs thereof. In embodiments, "NFκB" refers to the human protein. Included in the term "NFκB" are the wildtype and mutant forms of the protein. In embodiments, the term "NFκB" refers to the monomeric protein. In embodiments, the term "NFκB" refers to a dimer of NFκB (e.g. homodimer or heterodimer). In some embodiments, the term "NFκB" refers to a functional complex including NFκB proteins (e.g. homodimer or heterodimer). In embodiments, the term "NFκB" refers to the human protein also known as NFκB1, corresponding to Entrez 4790, OMIM 164011, RefSeq NM_003998, and/or UniProt P19838. In embodiments, the term "NFκB" refers to an NFκB dimer (e.g. homodimer or heterodimer) including the human protein corresponding to Entrez 4790, OMIM 164011, RefSeq NM_003998, and/or UniProt P19838. In embodiments, the term "NFκB" refers to the human protein also known as RelA or p65, corresponding to Entrez 5970, OMIM 164014, RefSeq NM_021975, and/or UniProt Q04206. In embodiments, the term "NFκB" refers to an NFκB dimer (e.g. homodimer or heterodimer) including the human protein corresponding to Entrez 5970, OMIM 164014, RefSeq NM_021975, and/or UniProt Q04206. In embodiments, the term "NFκB" refers to the human protein also known as NFκB2, corresponding to Entrez 4791, OMIM 164012, RefSeq NM_002502, and/or UniProt Q00653. In embodiments, the term "NFκB" refers to an NFκB dimer (e.g. homodimer or heterodimer) including the human protein corresponding to Entrez 4791, OMIM 164012, RefSeq NM_002502, and/or UniProt Q00653. In embodiments, the term "NFκB" refers to the human protein also known as RelB, corresponding to Entrez 5971, OMIM 604758, RefSeq NM_006509, and/or UniProt Q01201. In embodiments, the term "NFκB" refers to an NFκB dimer (e.g. homodimer or heterodimer) including the human protein corresponding to Entrez 5971, OMIM 604758, RefSeq NM_006509, and/or UniProt Q01201. In embodiments, the term "NFκB" refers to the human protein also known as c-Rel, corresponding to Entrez 5966, OMIM 164910, RefSeq NM_002908, and/or UniProt Q04864. In embodiments, the term "NFκB" refers to an NFκB dimer (e.g. homodimer or heterodimer) including the human protein corresponding to Entrez 5966, OMIM 164910, RefSeq NM_002908, and/or UniProt Q04864. In embodiments, "NFκB" refers to the complex of human NFκB1 and RelA. In embodiments, "NFκB" refers to the complex of human NFκB1 and NFκB2. In embodiments, "NFκB" refers to the complex of human NFκB1 and RelB. In embodiments, "NFκB" refers to the complex of human NFκB1 and c-Rel. In embodiments, "NFκB" refers to the complex of human NFκB2 and RelA. In embodiments, "NFκB" refers to the complex of human NFκB2 and RelB. In embodiments, "NFκB" refers to the complex of human NFκB2 and c-Rel. In embodiments, "NFκB" refers to the complex of human RelA and RelB. In embodiments, "NFκB" refers to the complex of human RelA and c-Rel. In embodiments, "NFκB" refers to the complex of human RelB and c-Rel. In embodiments, "NFκB" refers to the homodimer of human NFκB1. In embodiments, "NFκB" refers to the homodimer of human NFκB2. In embodiments, "NFκB" refers to the homodimer of human RelA. In embodiments, "NFκB" refers to the homodimer of human RelB. In embodiments, "NFκB" refers to the homodimer of human c-Rel. In embodiments, the reference numbers above for "NFκB" refer to the protein, and associated nucleic acids, known as of the date of filing of this application. The term "TSC1" or "hamartin" refers to the protein "tuberous sclerosis protein 1". In embodiments, "TSC1" refers to the human protein. Included in the term "TSC2" are the wildtype and mutant forms of the protein. In embodiments, "TSC1" refers to the protein associated with Entrez Gene 7248, OMIM 605284, UniProt Q92574, and/or RefSeq (protein) NP_000359. In embodiments, the reference numbers immediately above refer to the protein, and associated nucleic acids, known as of the date of filing of this application. The term "TSC2" or "tuberin" refers to the protein "tuberous sclerosis protein 2". In embodiments, "TSC2" refers to the human protein. Included in the term "TSC2" are the wildtype and mutant forms of the protein. In embodiments, "TSC2" refers to the protein associated with Entrez Gene 7249, OMIM 191092, UniProt P49815, and/or RefSeq (protein) NP_000539. In embodiments, the reference numbers immediately above refer to the protein, and associated nucleic acids, known as of the date of filing of this application. The term "mTOR" refers to the protein "mammalian target of rapamycin". In embodiments, "mTOR" refers to the human protein. Included in the term "mTOR" are the wildtype and mutant forms of the protein. In embodiments, "mTOR" refers to the protein associated with Entrez Gene 2475, OMIM 601231, UniProt P42345, and/or RefSeq (protein) NP_004949. In embodiments, the reference numbers immediately above refer to the protein, and associated nucleic acids, known as of the date of filing of this application.

"Anti-cancer agent" is used in accordance with its plain ordinary meaning and refers to a composition (e.g. compound, drug, antagonist, inhibitor, modulator) having antineoplastic properties or the ability to inhibit the growth or proliferation of cells. In some embodiments, an anti-cancer agent is a chemotherapeutic. In some embodiments, an anti-cancer agent is an agent identified herein having utility in methods of treating cancer. In some embodiments, an anti-cancer agent is an agent approved by the FDA or similar regulatory agency of a country other than the USA, for treating cancer. Examples of anti-cancer agents include, but are not limited to, MEK (e.g. MEK1, MEK2, or MEK1 and MEK2) inhibitors (e.g. XL518, CI-1040, PD035901, selumetinib/AZD6244, GSK1120212/trametinib, GDC-0973, ARRY-162, ARRY-300, AZD8330, PD0325901, U0126, PD98059, TAK-733, PD318088, AS703026, BAY 869766), alkylating agents (e.g., cyclophosphamide, ifosfamide, chlorambucil, busulfan, melphalan, mechlorethamine, uramustine, thiotepa, nitrosoureas, nitrogen mustards (e.g., mechloroethamine, cyclophosphamide, chlorambucil, meiphalan), ethylenimine and methylmelamines (e.g., hexamethlymelamine, thiotepa), alkyl sulfonates (e.g., busulfan), nitrosoureas (e.g., carmustine, lomusitne, semustine, streptozocin), triazenes (decarbazine)), anti-metabolites (e.g., 5-azathioprine, leucovorin, capecitabine, fludarabine, gemcitabine, pemetrexed, raltitrexed, folic acid analog (e.g., methotrexate), or pyrimidine analogs (e.g., fluorouracil, floxouridine, Cytarabine), purine analogs (e.g., mercaptopurine, thioguanine, pentostatin), etc.), plant alkaloids (e.g., vincristine, vinblastine, vinorelbine, vindesine, podophyllotoxin, paclitaxel, docetaxel, etc.), topoisomerase inhibitors (e.g., irinotecan, topotecan, amsacrine, etoposide (VP16), etoposide phosphate, teniposide, etc.), antitumor antibiotics (e.g., doxorubicin, adriamycin, daunorubicin, epirubicin, actinomycin, bleomycin, mitomycin, mitoxantrone, plicamycin, etc.), platinum-based compounds or platinum containing agents (e.g. cisplatin, oxaloplatin, carboplatin), anthracenedione (e.g., mitoxantrone), substituted urea (e.g., hydroxyurea), methyl hydrazine derivative (e.g., procarbazine), adrenocortical suppressant (e.g., mitotane, aminoglutethimide), epipodophyllotoxins (e.g., etoposide), antibiotics (e.g., daunorubicin, doxorubicin, bleomycin), enzymes (e.g., L-asparaginase), inhibitors of mitogen-activated protein kinase signaling (e.g. U0126, PD98059, PD184352, PD0325901, ARRY-142886, SB239063, SP600125, BAY 43-9006, wortmannin, or LY294002, Syk inhibitors, mTOR inhibitors, antibodies (e.g., rituxan), gossyphol, genasense, polyphenol E, Chlorofusin, all trans-retinoic acid (ATRA), bryostatin, tumor necrosis factor-related apoptosis-inducing ligand (TRAIL), 5-aza-2'-deoxycytidine, all trans retinoic acid, doxorubicin, vincristine, etoposide, gemcitabine, imatinib (Gleevec®), geldanamycin, 17-N-Allylamino-17-Demethoxygeldanamycin (17-AAG), flavopiridol, LY294002, bortezomib, trastuzumab, BAY 11-7082, PKC412, PD184352, 20-epi-1, 25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; 9-dioxamycin; diphenyl spiromustine; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylerie conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen-binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; zinostatin stimalamer, Adriamycin, Dactinomycin, Bleomycin, Vinblastine, Cisplatin, acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cladribine; crisnatol mesylate; cyclophosphamide; cytarabine; dacarbazine; daunorubicin hydrochloride; decitabine; dexormaplatin; dezaguanine; dezaguanine mesylate; diaziquone; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; iimofosine; interleukin I1 (including recombinant interleukin II, or rIL.sub.2), interferon alfa-2a; interferon alfa-2b; interferon alfa-n1; interferon alfa-n3; interferon beta-1a; interferon gamma-1b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazoie; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride, agents that arrest cells in the G2-M phases and/or modulate the formation or stability of microtubules, (e.g. Taxol™ (i.e. paclitaxel), Taxotere™, compounds comprising the taxane skeleton, Erbulozole (i.e. R-55104), Dolastatin 10 (i.e. DLS-10 and NSC-376128), Mivobulin isethionate (i.e. as CI-980), Vincristine, NSC-639829, Discodermolide (i.e. as NVP-XX-A-296), ABT-751 (Abbott, i.e. E-7010), Altorhyrtins (e.g. Altorhyrtin A and Altorhyrtin C), Spongistatins (e.g. Spongistatin 1, Spongistatin 2, Spongistatin 3, Spongistatin 4, Spongistatin 5, Spongistatin 6, Spongistatin 7, Spongistatin 8, and Spongistatin 9), Cemadotin hydrochloride (i.e. LU-103793 and NSC-D-669356), Epothilones (e.g. Epothilone A, Epothilone B, Epothilone C (i.e. desoxyepothilone A or dEpoA), Epothilone D (i.e. KOS-862, dEpoB, and desoxyepothilone B), Epothilone E, Epothilone F, Epothilone B N-oxide, Epothilone A N-oxide, 16-aza-epothilone B, 21-aminoepothilone B (i.e. BMS-310705), 21-hydroxyepothilone D (i.e. Desoxyepothilone F and dEpoF), 26-fluoroepothilone, Auristatin PE (i.e. NSC-654663), Soblidotin (i.e. TZT-1027), LS-4559-P (Pharmacia, i.e. LS-4577), LS-4578 (Pharmacia, i.e. LS-477-P), LS-4477 (Pharmacia), LS-4559 (Pharmacia), RPR-112378 (Aventis), Vincristine sulfate, DZ-3358 (Daiichi), FR-182877 (Fujisawa, i.e. WS-9885B), GS-164 (Takeda), GS-198 (Takeda), KAR-2 (Hungarian Academy of Sciences), BSF-223651 (BASF, i.e. ILX-651 and LU-223651), SAH-49960 (Lilly/Novartis), SDZ-268970 (Lilly/Novartis), AM-97 (Armad/Kyowa Hakko), AM-132 (Armad), AM-138 (Armad/Kyowa Hakko), IDN-5005 (Indena), Cryptophycin 52 (i.e. LY-355703), AC-7739 (Ajinomoto, i.e. AVE-8063A and CS-39.HCl), AC-7700 (Ajinomoto, i.e. AVE-8062, AVE-8062A, CS-39-L-Ser.HCl, and RPR-258062A), Vitilevuamide, Tubulysin A, Canadensol, Centaureidin (i.e. NSC-106969), T-138067 (Tularik, i.e. T-67, TL-138067 and TI-138067), COBRA-1 (Parker Hughes Institute, i.e. DDE- 261 and WHI-261), H10 (Kansas State University), H16 (Kansas State University), Oncocidin A1 (i.e. BTO-956 and DIME), DDE-313 (Parker Hughes Institute), Fijianolide B, Laulimalide, SPA-2 (Parker Hughes Institute), SPA-1 (Parker Hughes Institute, i.e. SPIKET-P), 3-IAABU (Cytoskeleton/Mt. Sinai School of Medicine, i.e. MF-569), Narcosine (also known as NSC-5366), Nascapine, D-24851 (Asta Medica), A-105972 (Abbott), Hemiasterlin, 3-BAABU (Cytoskeleton/Mt. Sinai School of Medicine, i.e. MF-191), TMPN (Arizona State University), Vanadocene acetylacetonate, T-138026 (Tularik), Monsatrol, lnanocine (i.e. NSC-698666), 3-IAABE (Cytoskeleton/Mt. Sinai School of Medicine), A-204197 (Abbott), T-607 (Tuiarik, i.e. T-900607), RPR-115781 (Aventis), Eleutherobins (such as Desmethyleleutherobin, Desaetyleleutherobin, lsoeleutherobin A, and Z-Eleutherobin), Caribaeoside, Caribaeolin, Halichondrin B, D-64131 (Asta Medica), D-68144 (Asta Medica), Diazonamide A, A-293620 (Abbott), NPI-2350 (Nereus), Taccalonolide A, TUB-245 (Aventis), A-259754 (Abbott), Diozostatin, (–)-Phenylahistin (i.e. NSCL-96F037), D-68838 (Asta Medica), D-68836 (Asta Medica), Myoseverin B, D-43411 (Zentaris, i.e. D-81862), A-289099 (Abbott), A-318315 (Abbott), HTI-286 (i.e. SPA-110, trifluoroacetate salt) (Wyeth), D-82317 (Zentaris), D-82318 (Zentaris), SC-12983 (NCI), Resverastatin phosphate sodium, BPR-OY-007 (National Health Research Institutes), and SSR-250411 (Sanofi)), steroids (e.g., dexamethasone), finasteride, aromatase inhibitors, gonadotropin-releasing hormone agonists (GnRH) such as goserelin or leuprolide, adrenocorticosteroids (e.g., prednisone), progestins (e.g., hydroxyprogesterone caproate, megestrol acetate, medroxyprogesterone acetate), estrogens (e.g., diethylstilbestrol, ethinyl estradiol), antiestrogen (e.g., tamoxifen), androgens (e.g., testosterone propionate, fluoxymesterone), antiandrogen (e.g., flutamide), immunostimulants (e.g., Bacillus Calmette-Guérin (BCG), levamisole, interleukin-2, alpha-interferon, etc.), monoclonal antibodies (e.g., anti-CD20, anti-HER2, anti-CD52, anti-HLA-DR, and anti-VEGF monoclonal antibodies), immunotoxins (e.g., anti-CD33 monoclonal antibody-calicheamicin conjugate, anti-CD22 monoclonal antibody-pseudomonas exotoxin conjugate, etc.), radioimmunotherapy (e.g., anti-CD20 monoclonal antibody conjugated to $^{111}$In, $^{90}$Y, or $^{131}$I, etc.), triptolide, homoharringtonine, dactinomycin, doxorubicin, epirubicin, topotecan, itraconazole, vindesine, cerivastatin, vincristine, deoxyadenosine, sertraline, pitavastatin, irinotecan, clofazimine, 5-nonyloxytryptamine, vemurafenib, dabrafenib, erlotinib, gefitinib, EGFR inhibitors, epidermal growth factor receptor (EGFR)-targeted therapy or therapeutic (e.g. gefitinib (Iressa™), erlotinib (Tarceva™), cetuximab (Erbitux™), lapatinib (Tykerb™), panitumumab (Vectibix™), vandetanib (Caprelsa™), afatinib/BIBW2992, CI-1033/canertinib, neratinib/HKI-272, CP-724714, TAK-285, AST-1306, ARRY334543, ARRY-380, AG-1478, dacomitinib/PF299804, OSI-420/desmethyl erlotinib, AZD8931, AEE788, pelitinib/EKB-569, CUDC-101, WZ8040, WZ4002, WZ3146, AG-490, XL647, PD153035, BMS-599626), sorafenib, imatinib, sunitinib, dasatinib, hormonal therapies, or the like.

The term "platinum-based compound" or "platinum containing agent" as used herein refers to a compound comprising a heavy metal complex containing a central atom of platinum surrounded by organic and/or inorganic functionalities. Non-limiting examples of platinum-based compounds include oxaliplatin, cisplatin, carboplatin, pharmaceutically acceptable salts thereof, stereoisomers thereof, derivatives thereof, analogs thereof, and combinations thereof. Included within platinum-based compounds are platinum-based drugs.

"Hormonal therapy" or "hormone therapy" is used in accordance with its plain ordinary meaning and refers to the treatment of a disease (e.g. cancer) by administration of an agent (e.g. compound) that modulates the production or activity of a hormone, the activity of a protein that is modulated by a hormone, or a signaling pathway that is modulated by a hormone or the activity of a hormone. An agent used in hormonal therapy may be referred to as a "hormonal therapy agent" or "hormonal therapeutic agent". Hormonal therapeutic agents include, but are not limited to, estrogens, androgens, antiestrogens, antiandrogens, endocrine therapies, steroids (e.g., dexamethasone), finasteride, fulvestrant, aromatase inhibitors (e.g. exemestane, anastrozole, aminoglutethimide, testolactone, letrozole, vorozole, formestane, or fadrozole), tamoxifen, and gonadotropin-releasing hormone agonists (GnRH) such as goserelin.

"Chemotherapeutic" or "chemotherapeutic agent" is used in accordance with its plain ordinary meaning and refers to a chemical composition or compound having antineoplastic properties or the ability to inhibit the growth or proliferation of cells.

"Therapy resistant" cancers, tumor cells, and tumors refer to cancers that have become resistant to one or more cancer therapies including, but not limited to, an anti-cancer agent, a chemotherapy (e.g. a chemotherapeutic), a hormonal therapy (e.g. a hormonal therapeutic agent), a radiotherapy, an immunotherapy, and/or combinations thereof.

Additionally, the compounds described herein can be co-administered with conventional immunotherapeutic agents including, but not limited to, immunostimulants (e.g., Bacillus Calmette-Guérin (BCG), levamisole, interleukin-2, alpha-interferon, etc.), monoclonal antibodies (e.g., anti-CD20, anti-HER2, anti-CD52, anti-HLA-DR, and anti-VEGF monoclonal antibodies), immunotoxins (e.g., anti-CD33 monoclonal antibody-calicheamicin conjugate, anti-CD22 monoclonal antibody-pseudomonas exotoxin conjugate, etc.), and radioimmunotherapy (e.g., anti-CD20 monoclonal antibody conjugated to $^{111}$In, $^{90}$Y, or $^{131}$I, etc.).

In a further embodiment, the compounds described herein can be co-administered with conventional radiotherapeutic agents including, but not limited to, radionuclides such as $^{47}$Sc, $^{64}$Cu, $^{67}$Cu, $^{89}$Sr, $^{86}$Y, $^{87}$Y, $^{90}$Y, $^{105}$Rh, $^{111}$Ag, $^{111}$In, $^{117m}$Sn, $^{149}$Pm, $^{153}$Sm, $^{166}$Ho, $^{177}$Lu, $^{186}$Re, $^{188}$Re, $^{211}$At, and $^{212}$Bi, optionally conjugated to antibodies directed against tumor antigens.

The term "cancer stem cell" is used in accordance with its plain ordinary meaning within cancer biology and cell biology and refers to cancer cells with characteristics associated with non-cancerous stem cells, including for example the ability of self-renewal and the ability to differentiate into all cell types that make up a cancer sample (e.g. tumor or cancer cells). The term "cancer progenitor cell" is used in accordance with its plain ordinary meaning within cancer biology and cell biology and refers to cancer cells with characteristics associated with non-cancerous progenitor cells. In embodiments, cancer stem cells and/or cancer progenitor cells may be identified by the presence (or absence) of cell markers (e.g. CD133 (PROM1), CD44 (PGP1), CD24 (HSA), EpCAM (epithelial cell adhesion molecule, ESA (epithelial specific antigen)), THY1 (CD90), ATP-binding cassette B5 (ABCB5), Hoechst33342, CD34, and/or ALDH1 (aldehyde dehydrogenase). In embodiments, lung cancer stem/progenitor cells may be identified by the presence of CD133 and ALDH1 (e.g. high levels of ALDH1 compared to non-lung cancer stem/progenitor cells).

A "stem cell" is a cell characterized by the ability of self-renewal through mitotic cell division and the potential to differentiate into a tissue or an organ. Among mammalian stem cells, embryonic and somatic stem cells can be distinguished. Embryonic stem cells reside in the blastocyst and give rise to embryonic tissues, whereas somatic stem cells reside in adult tissues for the purpose of tissue regeneration and repair.

"Self renewal" refers to the ability of a cell to divide and generate at least one daughter cell with the self-renewing characteristics of the parent cell. The second daughter cell may commit to a particular differentiation pathway. For example, a self-renewing hematopoietic stem cell can divide and form one daughter stem cell and another daughter cell committed to differentiation in the myeloid or lymphoid pathway. A committed progenitor cell has typically lost the self-renewal capacity, and upon cell division produces two daughter cells that display a more differentiated (i.e., restricted) phenotype. Non-self renewing cells refers to cells that undergo cell division to produce daughter cells, neither of which have the differentiation potential of the parent cell type, but instead generates differentiated daughter cells.

The term "pluripotent" or "pluripotency" refers to cells with the ability to give rise to progeny that can undergo differentiation, under appropriate conditions, into cell types that collectively exhibit characteristics associated with cell lineages from the three germ layers (endoderm, mesoderm, and ectoderm). Pluripotent stem cells can contribute to tissues of a prenatal, postnatal or adult organism. A standard art-accepted test, such as the ability to form a teratoma in 8-12 week old SCID mice, can be used to establish the pluripotency of a cell population. However, identification of various pluripotent stem cell characteristics can also be used to identify pluripotent cells.

"Pluripotent stem cell characteristics" refer to characteristics of a cell that distinguish pluripotent stem cells from other cells. Expression or non-expression of certain combinations of molecular markers are examples of characteristics of pluripotent stem cells. More specifically, human pluripotent stem cells may express at least some, and optionally all, of the markers from the following non-limiting list: SSEA-3, SSEA-4, TRA-1-60, TRA-1-81, TRA-2-49/6E, ALP, Sox2, E-cadherin, UTF-1, Oct4, Lin28, Rex1, and Nanog. Cell morphologies associated with pluripotent stem cells are also pluripotent stem cell characteristics.

The terms "induced pluripotent stem cell," "iPS" and the like refer to a pluripotent stem cell artificially derived from a non-pluripotent cell. A "non-pluripotent cell" can be a cell of lesser potency to self-renew and differentiate than a pluripotent stem cell. Cells of lesser potency can be, but are not limited to adult stem cells, tissue specific progenitor cells, primary or secondary cells.

An adult stem cell is an undifferentiated cell found in an individual after embryonic development. Adult stem cells multiply by cell division to replenish dying cells and regenerate damaged tissue. An adult stem cell has the ability to divide and create another cell like itself or to create a more differentiated cell. Even though adult stem cells are associated with the expression of pluripotency markers such as Rex1, Nanog, Oct4 or Sox2, they do not have the ability of pluripotent stem cells to differentiate into the cell types of all three germ layers. Adult stem cells have a limited ability to self renew and generate progeny of distinct cell types. Adult stem cells can include hematopoietic stem cell, a cord blood stem cell, a mesenchymal stem cell, an epithelial stem cell, a skin stem cell or a neural stem cell. A tissue specific progenitor refers to a cell devoid of self-renewal potential that is committed to differentiate into a specific organ or tissue. A primary cell includes any cell of an adult or fetal organism apart from egg cells, sperm cells and stem cells. Examples of useful primary cells include, but are not limited to, skin cells, bone cells, blood cells, cells of internal organs and cells of connective tissue. A secondary cell is derived from a primary cell and has been immortalized for long-lived in vitro cell culture.

II. Compounds

In a first aspect is provided a compound, or a pharmaceutically acceptable salt thereof, wherein the compound has a formula selected from the group consisting of:

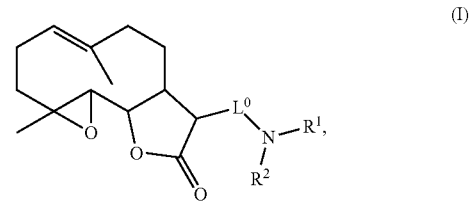

(I)

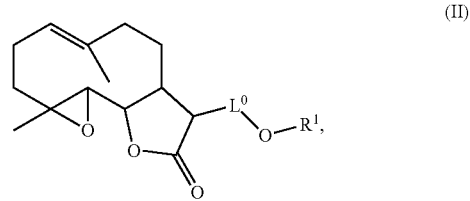

(II)

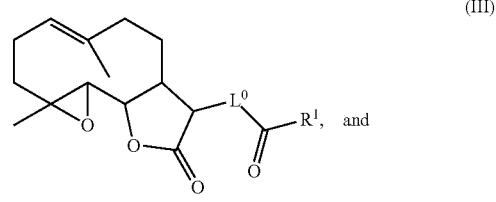

(III)

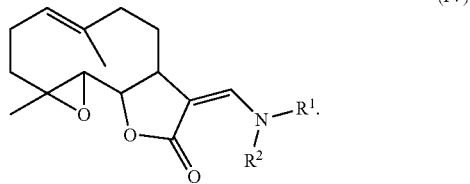

(IV)

$L^0$ is independently a bond or an unsubstituted $C_1$-$C_{10}$ alkylene. $R^1$ and $R^2$ are independently hydrogen, —OH, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; where $R^1$ and $R^2$ may optionally be joined to form a substituted or unsubstituted heterocycloalkyl or a substituted or unsubstituted heteroaryl.

In embodiments, the compound, or a pharmaceutically acceptable salt thereof, has the formula:

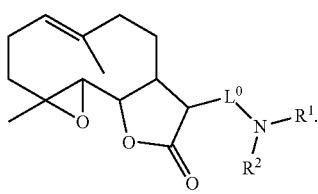

(I)

In embodiments, the compound, or a pharmaceutically acceptable salt thereof, has the formula:

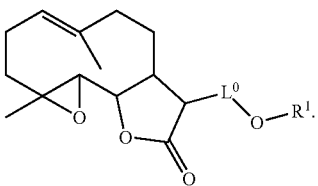

(II)

In embodiments, the compound, or a pharmaceutically acceptable salt thereof, has the formula:

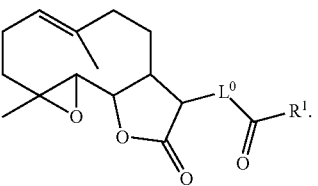

(III)

In embodiments, the compound, or a pharmaceutically acceptable salt thereof, has the formula:

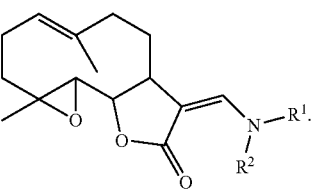

(IV)

In embodiments, the compound, or a pharmaceutically acceptable salt thereof, has the formula:

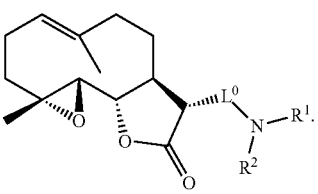

(Ia)

In embodiments, the compound, or a pharmaceutically acceptable salt thereof, has the formula:

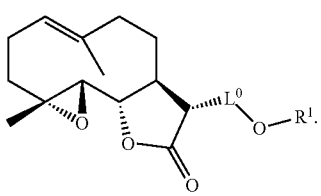

(IIa)

In embodiments, the compound, or a pharmaceutically acceptable salt thereof, has the formula:

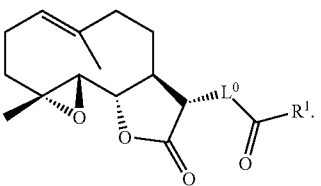

(IIIa)

In embodiments, the compound, or a pharmaceutically acceptable salt thereof, has the formula:

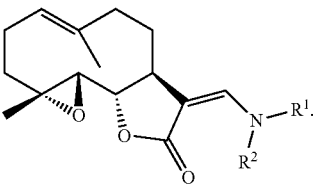

(IVa)

In embodiments, $L^0$ is a bond. In embodiments, $L^0$ is an unsubstituted $C_1$-$C_6$ alkylene. In embodiments, $L^0$ is an unsubstituted $C_1$-$C_4$ alkylene. In embodiments, $L^0$ is an unsubstituted methylene.

In embodiments, $R^1$ is $L^1$-$R^3$; $L^1$ is independently a bond or an unsubstituted $C_1$-$C_{10}$ alkylene; and $R^3$ is independently hydrogen, halogen, —$CH_3$, —$CF_3$, —$CCl_3$, —CN, —S(O)$CH_3$, —OH, —$NH_2$, —COOH, —$CONH_2$, —$NO_2$, —C(O)$CH_3$, —$CH_2CH_3$, —$CH_2CH_2OH$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)OH, —NHOH, —$OCH_3$, —$OCF_3$, —$OCHF_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, $L^0$ is a bond. In embodiments, $L^1$ is an unsubstituted $C_1$-$C_4$ alkylene. In embodiments, $L^1$ is an unsubstituted methylene.

In embodiments, $R^3$ is independently hydrogen, halogen, —$CH_3$, —$CF_3$, —$CCl_3$, —CN, —S(O)$CH_3$, —OH, —$NH_2$, —COOH, —$CONH_2$, —$NO_2$, —C(O)$CH_3$, —$CH_2CH_3$, —$CH_2CH_2OH$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)OH, —NHOH, —$OCH_3$, —$OCF_3$, —$OCHF_2$, 4-methoxybenzyl, 4-methoxyphenyl, or pyridyl.

In embodiments, $R^2$ is $L^2$-$R^4$; $L^2$ is independently a bond or an unsubstituted $C_1$-$C_{10}$ alkylene; and $R^4$ is independently hydrogen, halogen, —$CH_3$, —$CF_3$, —$CCl_3$, —CN, —S(O)$CH_3$, —OH, —$NH_2$, —COOH, —$CONH_2$, —$NO_2$, —C(O)$CH_3$, —$CH_2CH_3$, —$CH_2CH_2OH$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)OH, —NHOH, —$OCH_3$, —$OCF_3$, —$OCHF_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, $L^2$ is a bond. In embodiments, $L^2$ is an unsubstituted $C_1$-$C_4$ alkylene. In embodiments, $L^2$ is an unsubstituted methylene.

In embodiments, $R^4$ is independently hydrogen, halogen, —$CH_3$, —$CF_3$, —$CCl_3$, —CN, —S(O)$CH_3$, —OH, —$NH_2$, —COOH, —$CONH_2$, —$NO_2$, —C(O)$CH_3$, —$CH_2CH_3$, —$CH_2CH_2OH$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)OH, —NHOH, —$OCH_3$, —$OCF_3$, —$OCHF_2$, 4-methoxybenzyl, 4-methoxyphenyl, or pyridyl.

In embodiments, $R^1$ and $R^2$ are joined to form an unsubstituted heterocycloalkyl. In embodiments, $R^1$ and $R^2$ are joined to form an unsubstituted piperidinyl.

In embodiments of the pharmaceutically acceptable salt, the compound has a formula selected from the group consisting of formula I, II, IV, Ia, IIa, and IVa, wherein the compound includes a protonated nitrogen cation. In embodiments, the pharmaceutically acceptable salt of a compound described herein includes fumarate. In embodiments, the pharmaceutically acceptable salt of a compound described herein includes fumaric acid. In embodiments, the pharmaceutically acceptable salt of a compound described herein includes fumarate with a single negative charge. In embodiments, the pharmaceutically acceptable salt of a compound described herein includes chloride. In embodiments, the pharmaceutically acceptable salt of a compound described herein includes bromide. In embodiments, the pharmaceutically acceptable salt of a compound described herein includes sulfate. In embodiments, the pharmaceutically acceptable salt of a compound described herein includes methanesulfonate. In embodiments, the pharmaceutically acceptable salt of a compound described herein includes nitrate. In embodiments, the pharmaceutically acceptable salt of a compound described herein includes maleate. In embodiments, the pharmaceutically acceptable salt of a compound described herein includes acetate. In embodiments, the pharmaceutically acceptable salt of a compound described herein includes citrate. In embodiments, the pharmaceutically acceptable salt of a compound described herein includes tartrate. In embodiments, the pharmaceutically acceptable salt of a compound described herein includes succinate. In embodiments, the pharmaceutically acceptable salt of a compound described herein includes benzoate. In embodiments, the pharmaceutically acceptable salt of a compound described herein includes glutamate.

In embodiments, $R^1$ is independently hydrogen, $R^{11}$-substituted or unsubstituted alkyl, $R^{11}$-substituted or unsubstituted heteroalkyl, $R^{11}$-substituted or unsubstituted cycloalkyl, $R^1$-substituted or unsubstituted heterocycloalkyl, $R^{11}$-substituted or unsubstituted aryl, or $R^1$-substituted or unsubstituted heteroaryl. In embodiments, $R^1$ and $R^2$ may optionally be joined to form an $R^{11}$-substituted or unsubstituted heterocycloalkyl or $R^{11}$-substituted or unsubstituted heteroaryl.

$R^{11}$ is independently hydrogen, halogen, oxo, —$CH_3$, —$CF_3$, —$CCl_3$, —CN, —S(O)$CH_3$, —OH, —$NH_2$, —COOH, —$CONH_2$, —$NO_2$, —C(O)$CH_3$, —$CH_2CH_3$, —$CH_2CH_2OH$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)OH, —NHOH, —$OCH_3$, —$OCF_3$, —$OCHF_2$, $R^{12}$-substituted or unsubstituted alkyl, $R^{12}$-substituted or unsubstituted heteroalkyl, $R^{12}$-substituted or unsubstituted cycloalkyl, $R^{12}$-substituted or unsubstituted heterocycloalkyl, $R^{12}$-substituted or unsubstituted aryl, or $R^{12}$-substituted or unsubstituted heteroaryl.

In embodiments, $R^2$ is independently hydrogen, halogen, —$CH_3$, —$CF_3$, —$CCl_3$, —CN, —S(O)$CH_3$, —OH, —$NH_2$, —COOH, —$CONH_2$, —$NO_2$, —C(O)$CH_3$, —$CH_2CH_3$, —$CH_2CH_2OH$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)OH, —NHOH, —$OCH_3$, —$OCF_3$, —$OCHF_2$, $R^{13}$-substituted or unsubstituted alkyl, $R^{13}$-substituted or unsubstituted heteroalkyl, $R^{13}$-substituted or unsubstituted cycloalkyl, $R^{13}$-substituted or unsubstituted heterocycloalkyl, $R^{13}$-substituted or unsubstituted aryl, or $R^{13}$-substituted or unsubstituted heteroaryl. In embodiments, $R^1$ and $R^2$ may optionally be joined to form an $R^{13}$-substituted or unsubstituted heterocycloalkyl or $R^{13}$-substituted or unsubstituted heteroaryl.

$R^{13}$ is independently hydrogen, halogen, oxo, —$CH_3$, —$CF_3$, —$CCl_3$, —CN, —S(O)$CH_3$, —OH, —$NH_2$, —COOH, —$CONH_2$, —$NO_2$, —C(O)$CH_3$, —$CH_2CH_3$, —$CH_2CH_2OH$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)OH, —NHOH, —$OCH_3$, —$OCF_3$, —$OCHF_2$, $R^{14}$-substituted or unsubstituted alkyl, $R^{14}$-substituted or unsubstituted heteroalkyl, $R^{14}$-substituted or unsubstituted cycloalkyl, $R^{14}$-substituted or unsubstituted heterocycloalkyl, $R^{14}$-substituted or unsubstituted aryl, or $R^{14}$ substituted or unsubstituted heteroaryl.

In embodiments, $R^3$ is independently hydrogen, halogen, —$CH_3$, —$CF_3$, —$CCl_3$, —CN, —S(O)$CH_3$, —OH, —$NH_2$, —COOH, —$CONH_2$, —$NO_2$, —C(O)$CH_3$, —$CH_2CH_3$, —$CH_2CH_2OH$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)OH, —NHOH, —$OCH_3$, —$OCF_3$, —$OCHF_2$, $R^{15}$-substituted or unsubstituted alkyl, $R^{15}$-substituted or unsubstituted heteroalkyl, $R^{15}$-substituted or unsubstituted cycloalkyl, $R^{15}$-substituted or unsubstituted heterocycloalkyl, $R^{15}$-substituted or unsubstituted aryl, or $R^{15}$-substituted or unsubstituted heteroaryl.

$R^{15}$ is independently hydrogen, halogen, oxo, —$CH_3$, —$CF_3$, —$CCl_3$, —CN, —S(O)$CH_3$, —OH, —$NH_2$, —COOH, —$CONH_2$, —$NO_2$, —C(O)$CH_3$, —$CH_2CH_3$, —$CH_2CH_2OH$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)OH, —NHOH, —$OCH_3$, —$OCF_3$, —$OCHF_2$, $R^{16}$-substituted or unsubstituted alkyl, $R^{16}$-substituted or unsubstituted heteroalkyl, $R^{16}$-substituted or unsubstituted cycloalkyl, $R^{16}$-substituted or unsubstituted heterocycloalkyl, $R^{16}$-substituted or unsubstituted aryl, or $R^{16}$ substituted or unsubstituted heteroaryl.

In embodiments, $R^4$ is independently hydrogen, halogen, —$CH_3$, —$CF_3$, —$CCl_3$, —CN, —S(O)$CH_3$, —OH, —$NH_2$, —COOH, —$CONH_2$, —$NO_2$, —C(O)$CH_3$, —$CH_2CH_3$, —$CH_2CH_2OH$, —SH, —$SO_2Cl$, —$SO_3H$, —$SO_4H$, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)OH, —NHOH, —OCH$_3$, —OCF$_3$, —OCHF$_2$, R$^{17}$-substituted or unsubstituted alkyl, R$^{17}$-substituted or unsubstituted heteroalkyl, R$^{17}$-substituted or unsubstituted cycloalkyl, R$^{17}$-substituted or unsubstituted heterocycloalkyl, R$^{17}$-substituted or unsubstituted aryl, or R$^{17}$-substituted or unsubstituted heteroaryl.

R$^{17}$ is independently hydrogen, halogen, oxo, —CH$_3$, —CF$_3$, —CCl$_3$, —CN, —S(O)CH$_3$, —OH, —NH$_2$, —COOH, —CONH$_2$, —NO$_2$, —C(O)CH$_3$, —CH$_2$CH$_3$, —CH$_2$CH$_2$OH, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)OH, —NHOH, —OCH$_3$, —OCF$_3$, —OCHF$_2$, R$^{18}$-substituted or unsubstituted alkyl, R$^{18}$-substituted or unsubstituted heteroalkyl, R$^{18}$-substituted or unsubstituted cycloalkyl, R$^{18}$-substituted or unsubstituted heterocycloalkyl, R$^{18}$-substituted or unsubstituted aryl, or R$^{18}$-substituted or unsubstituted heteroaryl.

Each R$^{12}$, R$^{14}$, R$^{16}$, and R$^{18}$ is independently hydrogen, halogen, oxo, —CH$_3$, —CF$_3$, —CCl$_3$, —CN, —S(O)CH$_3$, —OH, —NH$_2$, —COOH, —CONH$_2$, —NO$_2$, —C(O)CH$_3$, —CH$_2$CH$_3$, —CH$_2$CH$_2$OH, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)OH, —NHOH, —OCH$_3$, —OCF$_3$, —OCHF$_2$, unsubstituted alkyl, unsubstituted heteroalkyl, unsubstituted cycloalkyl, unsubstituted heterocycloalkyl, unsubstituted aryl, or unsubstituted heteroaryl.

In some embodiments, a compound as described herein may include multiple instances of R$^{11}$, R$^{12}$, R$^{13}$, R$^{14}$, R$^{15}$, R$^{16}$, R$^{17}$, R$^{18}$, and/or other variables. In such embodiments, each variable may optional be different and be appropriately labeled to distinguish each group for greater clarity. For example, where each R$^{11}$, R$^{12}$, R$^{13}$, R$^{14}$, R$^{15}$, R$^{16}$, R$^{17}$, and/or R$^{18}$ is different, they may be referred to, for example, as R$^{11.1}$, R$^{11.2}$, R$^{11.3}$, R$^{11.4}$, R$^{12.1}$, R$^{12.2}$, R$^{12.3}$, R$^{12.4}$, R$^{13.1}$, R$^{13.2}$, R$^{13.3}$, R$^{13.4}$, R$^{14.1}$, R$^{14.2}$, R$^{14.3}$, R$^{14.4}$, R$^{15.1}$, R$^{15.2}$, R$^{15.3}$, R$^{15.4}$, R$^{16.1}$, R$^{16.2}$, R$^{16.3}$, R$^{16.4}$, R$^{17.1}$, R$^{17.2}$, R$^{17.3}$, R$^{17.4}$, R$^{18.1}$, R$^{18.2}$, R$^{18.3}$, and/or R$^{18.4}$, respectively, wherein the definition of R$^{11}$ is assumed by R$^{11.1}$, R$^{11.2}$, R$^{11.3}$, and/or R$^{11.4}$, the definition of R$^{12}$ is assumed by R$^{12.1}$, R$^{12.2}$, R$^{12.3}$, and/or R$^{12.4}$, the definition of R$^{13}$ is assumed by R$^{13.1}$, R$^{13.2}$, R$^{13.3}$, and/or R$^{13.4}$, the definition of R$^{14}$ is assumed by R$^{14.1}$, R$^{14.2}$, R$^{14.3}$, and/or R$^{14.4}$, the definition of R$^{15}$ is assumed by R$^{15.1}$, R$^{15.2}$, R$^{15.3}$, and/or R$^{15.4}$, the definition of R$^{16}$ is assumed by R$^{16.1}$, R$^{16.2}$, R$^{16.3}$, and/or R$^{16.4}$, the definition of R$^{17}$ is assumed by R$^{17.1}$, R$^{17.2}$, R$^{17.3}$, and/or R$^{17.4}$, and the definition of R$^{18}$ is assumed by R$^{18.1}$, R$^{18.2}$, R$^{18.3}$, and/or R$^{18.4}$. The variables used within a definition of R$^{11}$, R$^{12}$, R$^{13}$, R$^{14}$, R$^{15}$, R$^{16}$R$^{17}$, R$^{18}$, and/or other variables that appear at multiple instances and are different may similarly be appropriately labeled to distinguish each group for greater clarity.

In embodiments, the compound has formula (I) and L$^0$ is unsubstituted C$_1$-C$_{10}$ alkylene. In embodiments, the compound has formula (I) and L$^0$ is unsubstituted C$_1$-C$_8$ alkylene. In embodiments, the compound has formula (I) and L$^0$ is unsubstituted C$_1$-C$_6$ alkylene. In embodiments, the compound has formula (I) and L$^0$ is unsubstituted C$_1$-C$_4$ alkylene. In embodiments, the compound has formula (I) and L$^0$ is unsubstituted C$_1$-C$_3$ alkylene. In embodiments, the compound has formula (I) and L$^0$ is unsubstituted C$_1$-C$_2$ alkylene. In embodiments, the compound has formula (I) and L$^0$ is unsubstituted branched C$_1$-C$_4$ alkylene. In embodiments, the compound has formula (I) and L$^0$ is unsubstituted branched C$_1$-C$_3$ alkylene. In embodiments, the compound has formula (I) and L$^0$ is unsubstituted methylene. In embodiments, the compound has formula (I) and L$^0$ is unsubstituted ethylene. In embodiments, the compound has formula (I) and L$^0$ is a bond.

In embodiments, the compound has formula (I) and R$^1$ is independently hydrogen. In embodiments, the compound has formula (I) and R$^1$ is independently halogen. In embodiments, the compound has formula (I) and R$^1$ is independently —CH$_3$. In embodiments, the compound has formula (I) and R$^1$ is independently —CF$_3$. In embodiments, the compound has formula (I) and R$^1$ is independently —OH. In embodiments, the compound has formula (I) and R$^1$ is independently substituted 4-methoxybenzyl. In embodiments, the compound has formula (I) and R$^1$ is independently substituted 4-methoxyphenyl. In embodiments, the compound has formula (I) and R$^1$ is independently substituted pyridyl. In embodiments, the compound has formula (I) and R$^1$ is independently unsubstituted 4-methoxybenzyl. In embodiments, the compound has formula (I) and R$^1$ is independently unsubstituted 4-methoxyphenyl. In embodiments, the compound has formula (I) and R$^1$ is independently unsubstituted pyridyl. In embodiments, the compound has formula (I) and R$^1$ is substituted or unsubstituted alkyl. In embodiments, the compound has formula (I) and R$^1$ is substituted or unsubstituted heteroalkyl. In embodiments, the compound has formula (I) and R$^1$ is substituted or unsubstituted cycloalkyl. In embodiments, the compound has formula (I) and R$^1$ is substituted or unsubstituted heterocycloalkyl. In embodiments, the compound has formula (I) and R$^1$ is substituted or unsubstituted aryl. In embodiments, the compound has formula (I) and R$^1$ is substituted or unsubstituted heteroaryl. In embodiments, the compound has formula (I) and R$^1$ is unsubstituted alkyl. In embodiments, the compound has formula (I) and R$^1$ is unsubstituted heteroalkyl. In embodiments, the compound has formula (I) and R$^1$ is unsubstituted cycloalkyl. In embodiments, the compound has formula (I) and R$^1$ is unsubstituted heterocycloalkyl. In embodiments, the compound has formula (I) and R$^1$ is unsubstituted aryl. In embodiments, the compound has formula (I) and R$^1$ is unsubstituted heteroaryl. In embodiments, the compound has formula (I) and R$^1$ is substituted or unsubstituted C$_1$-C$_8$ alkyl. In embodiments, the compound has formula (I) and R$^1$ is substituted or unsubstituted C$_1$-C$_6$ alkyl. In embodiments, the compound has formula (I) and R$^1$ is substituted or unsubstituted C$_1$-C$_4$ alkyl. In embodiments, the compound has formula (I) and R$^1$ is substituted or unsubstituted C$_1$-C$_2$ alkyl. In embodiments, the compound has formula (I) and R$^1$ is substituted or unsubstituted methyl. In embodiments, the compound has formula (I) and R$^1$ is unsubstituted methyl. In embodiments, the compound has formula (I) and R$^1$ is substituted or unsubstituted 2 to 8 membered heteroalkyl. In embodiments, the compound has formula (I) and R$^1$ is substituted or unsubstituted 2 to 6 membered heteroalkyl. In embodiments, the compound has formula (I) and R$^1$ is substituted or unsubstituted 2 to 4 membered heteroalkyl. In embodiments, the compound has formula (I) and R$^1$ is substituted or unsubstituted 2 to 3 membered heteroalkyl. In embodiments, the compound has formula (I) and R$^1$ is substituted or unsubstituted C$_3$-C$_7$ cycloalkyl. In embodiments, the compound has formula (I) and R$^1$ is substituted or unsubstituted 3 to 7 membered heterocycloalkyl. In embodiments, the compound has formula (I) and R$^1$ is substituted or unsubstituted 5 to 7 membered heterocycloalkyl. In embodiments, the compound has formula (I) and R$^1$ is substituted or unsubstituted 5 to 6 membered heterocycloalkyl. In embodiments, the compound has formula (I) and R$^1$ is substituted or unsubstituted C$_6$-C$_{10}$ aryl. In embodiments, the compound has formula (I) and R$^1$ is substituted or unsubstituted phenyl. In embodiments, the compound has formula (I) and $R^1$ is substituted or unsubstituted 5 to 9 membered heteroaryl. In embodiments, the compound has formula (I) and $R^1$ is substituted or unsubstituted 5 to 6 membered heteroaryl. In embodiments, the compound has formula (I) and $R^1$ is substituted or unsubstituted 5 membered heteroaryl. In embodiments, the compound has formula (I) and $R^1$ is substituted or unsubstituted 6 membered heteroaryl. In embodiments, the compound has formula (I) and $R^1$ is substituted or unsubstituted fused ring heteroaryl. In embodiments, the compound has formula (I) and $R^1$ is substituted or unsubstituted 9 membered heteroaryl. In embodiments, the compound has formula (I) and $R^1$ is substituted or unsubstituted 10 membered heteroaryl. In embodiments, the compound has formula (I) and $R^1$ is —$OCH_3$. In embodiments, the compound has formula (I) and $R^1$ is —$CH_2CH_2OH$. In embodiments, the compound has formula (I) and $R^1$ is —$CH_2CH_3$.

In embodiments, the compound has formula (I) and $R^1$ is $L^1$-$R^3$. In embodiments, the compound has formula (I) and $L^1$ is unsubstituted $C_1$-$C_{10}$ alkylene. In embodiments, the compound has formula (I) and $L^1$ is unsubstituted $C_1$-$C_8$ alkylene. In embodiments, the compound has formula (I) and $L^1$ is unsubstituted $C_1$-$C_6$ alkylene. In embodiments, the compound has formula (I) and $L^1$ is unsubstituted $C_1$-$C_4$ alkylene. In embodiments, the compound has formula (I) and $L^1$ is unsubstituted $C_1$-$C_3$ alkylene. In embodiments, the compound has formula (I) and $L^1$ is unsubstituted $C_1$-$C_2$ alkylene. In embodiments, the compound has formula (I) and $L^1$ is unsubstituted branched $C_1$-$C_4$ alkylene. In embodiments, the compound has formula (I) and $L^1$ is unsubstituted branched $C_1$-$C_3$ alkylene. In embodiments, the compound has formula (I) and $L^1$ is unsubstituted methylene. In embodiments, the compound has formula (I) and $L^1$ is unsubstituted ethylene. In embodiments, the compound has formula (I) and $L^1$ is a bond. In embodiments, the compound has formula (I) and $R^3$ is independently hydrogen. In embodiments, the compound has formula (I) and $R^3$ is independently halogen. In embodiments, the compound has formula (I) and $R^3$ is independently —$CH_3$. In embodiments, the compound has formula (I) and $R^3$ is independently —$CF_3$. In embodiments, the compound has formula (I) and $R^3$ is independently —OH. In embodiments, the compound has formula (I) and $R^3$ is independently substituted 4-methoxybenzyl. In embodiments, the compound has formula (I) and $R^3$ is independently substituted 4-methoxyphenyl. In embodiments, the compound has formula (I) and $R^3$ is independently substituted pyridyl. In embodiments, the compound has formula (I) and $R^3$ is independently unsubstituted 4-methoxybenzyl. In embodiments, the compound has formula (I) and $R^3$ is independently unsubstituted 4-methoxyphenyl. In embodiments, the compound has formula (I) and $R^3$ is independently unsubstituted pyridyl. In embodiments, the compound has formula (I) and $R^3$ is substituted or unsubstituted alkyl. In embodiments, the compound has formula (I) and $R^3$ is substituted or unsubstituted heteroalkyl. In embodiments, the compound has formula (I) and $R^3$ is substituted or unsubstituted cycloalkyl. In embodiments, the compound has formula (I) and $R^3$ is substituted or unsubstituted heterocycloalkyl. In embodiments, the compound has formula (I) and $R^3$ is substituted or unsubstituted aryl. In embodiments, the compound has formula (I) and $R^3$ is substituted or unsubstituted heteroaryl. In embodiments, the compound has formula (I) and $R^3$ is unsubstituted alkyl. In embodiments, the compound has formula (I) and $R^3$ is unsubstituted heteroalkyl. In embodiments, the compound has formula (I) and $R^3$ is unsubstituted cycloalkyl. In embodiments, the compound has formula (I) and $R^3$ is unsubstituted heterocycloalkyl. In embodiments, the compound has formula (I) and $R^3$ is unsubstituted aryl. In embodiments, the compound has formula (I) and $R^3$ is unsubstituted heteroaryl. In embodiments, the compound has formula (I) and $R^3$ is substituted or unsubstituted $C_1$-$C_8$ alkyl. In embodiments, the compound has formula (I) and $R^3$ is substituted or unsubstituted $C_1$-$C_6$ alkyl. In embodiments, the compound has formula (I) and $R^3$ is substituted or unsubstituted $C_1$-$C_4$ alkyl. In embodiments, the compound has formula (I) and $R^3$ is substituted or unsubstituted $C_1$-$C_2$ alkyl. In embodiments, the compound has formula (I) and $R^3$ is substituted or unsubstituted methyl. In embodiments, the compound has formula (I) and $R^3$ is unsubstituted methyl. In embodiments, the compound has formula (I) and $R^3$ is substituted or unsubstituted 2 to 8 membered heteroalkyl. In embodiments, the compound has formula (I) and $R^3$ is substituted or unsubstituted 2 to 6 membered heteroalkyl. In embodiments, the compound has formula (I) and $R^3$ is substituted or unsubstituted 2 to 4 membered heteroalkyl. In embodiments, the compound has formula (I) and $R^3$ is substituted or unsubstituted 2 to 3 membered heteroalkyl. In embodiments, the compound has formula (I) and $R^3$ is substituted or unsubstituted $C_3$-$C_7$ cycloalkyl. In embodiments, the compound has formula (I) and $R^3$ is substituted or unsubstituted 3 to 7 membered heterocycloalkyl. In embodiments, the compound has formula (I) and $R^3$ is substituted or unsubstituted 5 to 7 membered heterocycloalkyl. In embodiments, the compound has formula (I) and $R^3$ is substituted or unsubstituted 5 to 6 membered heterocycloalkyl. In embodiments, the compound has formula (I) and $R^3$ is substituted or unsubstituted $C_6$-$C_{10}$ aryl. In embodiments, the compound has formula (I) and $R^3$ is substituted or unsubstituted phenyl. In embodiments, the compound has formula (I) and $R^3$ is substituted or unsubstituted 5 to 9 membered heteroaryl. In embodiments, the compound has formula (I) and $R^3$ is substituted or unsubstituted 5 to 6 membered heteroaryl. In embodiments, the compound has formula (I) and $R^3$ is substituted or unsubstituted 5 membered heteroaryl. In embodiments, the compound has formula (I) and $R^3$ is substituted or unsubstituted 6 membered heteroaryl. In embodiments, the compound has formula (I) and $R^3$ is substituted or unsubstituted fused ring heteroaryl. In embodiments, the compound has formula (I) and $R^3$ is substituted or unsubstituted 9 membered heteroaryl. In embodiments, the compound has formula (I) and $R^3$ is substituted or unsubstituted 10 membered heteroaryl. In embodiments, the compound has formula (I) and $R^3$ is —$OCH_3$. In embodiments, the compound has formula (I) and $R^3$ is —$CH_2CH_2OH$. In embodiments, the compound has formula (I) and $R^3$ is —$CH_2CH_3$.

In embodiments, the compound has formula (I) and $R^2$ is independently hydrogen. In embodiments, the compound has formula (I) and $R^2$ is independently halogen. In embodiments, the compound has formula (I) and $R^2$ is independently —$CH_3$. In embodiments, the compound has formula (I) and $R^2$ is independently —$CF_3$. In embodiments, the compound has formula (I) and $R^2$ is independently —OH. In embodiments, the compound has formula (I) and $R^2$ is independently substituted 4-methoxybenzyl. In embodiments, the compound has formula (I) and $R^2$ is independently substituted 4-methoxyphenyl. In embodiments, the compound has formula (I) and $R^2$ is independently substituted pyridyl. In embodiments, the compound has formula (I) and $R^2$ is independently unsubstituted 4-methoxybenzyl. In embodiments, the compound has formula (I) and $R^2$ is independently unsubstituted 4-methoxyphenyl. In embodiments, the compound has formula (I) and $R^2$ is independently unsubstituted pyridyl. In embodiments, the compound has formula (I) and $R^2$ is substituted or unsubstituted alkyl. In embodiments, the compound has formula (I) and $R^2$ is substituted or unsubstituted heteroalkyl. In embodiments, the compound has formula (I) and $R^2$ is substituted or unsubstituted cycloalkyl. In embodiments, the compound has formula (I) and $R^2$ is substituted or unsubstituted heterocycloalkyl. In embodiments, the compound has formula (I) and $R^2$ is substituted or unsubstituted aryl. In embodiments, the compound has formula (I) and $R^2$ is substituted or unsubstituted heteroaryl. In embodiments, the compound has formula (I) and $R^2$ is unsubstituted alkyl. In embodiments, the compound has formula (I) and $R^2$ is unsubstituted heteroalkyl. In embodiments, the compound has formula (I) and $R^2$ is unsubstituted cycloalkyl. In embodiments, the compound has formula (I) and $R^2$ is unsubstituted heterocycloalkyl. In embodiments, the compound has formula (I) and $R^2$ is unsubstituted aryl. In embodiments, the compound has formula (I) and $R^2$ is unsubstituted heteroaryl. In embodiments, the compound has formula (I) and $R^2$ is substituted or unsubstituted $C_1$-$C_8$ alkyl. In embodiments, the compound has formula (I) and $R^2$ is substituted or unsubstituted $C_1$-$C_6$ alkyl. In embodiments, the compound has formula (I) and $R^2$ is substituted or unsubstituted $C_1$-$C_4$ alkyl. In embodiments, the compound has formula (I) and $R^2$ is substituted or unsubstituted $C_1$-$C_2$ alkyl. In embodiments, the compound has formula (I) and $R^2$ is substituted or unsubstituted methyl. In embodiments, the compound has formula (I) and $R^2$ is unsubstituted methyl. In embodiments, the compound has formula (I) and $R^2$ is substituted or unsubstituted 2 to 8 membered heteroalkyl. In embodiments, the compound has formula (I) and $R^2$ is substituted or unsubstituted 2 to 6 membered heteroalkyl. In embodiments, the compound has formula (I) and $R^2$ is substituted or unsubstituted 2 to 4 membered heteroalkyl. In embodiments, the compound has formula (I) and $R^2$ is substituted or unsubstituted 2 to 3 membered heteroalkyl. In embodiments, the compound has formula (I) and $R^2$ is substituted or unsubstituted $C_3$-$C_7$ cycloalkyl. In embodiments, the compound has formula (I) and $R^2$ is substituted or unsubstituted 3 to 7 membered heterocycloalkyl. In embodiments, the compound has formula (I) and $R^2$ is substituted or unsubstituted 5 to 7 membered heterocycloalkyl. In embodiments, the compound has formula (I) and $R^2$ is substituted or unsubstituted 5 to 6 membered heterocycloalkyl. In embodiments, the compound has formula (I) and $R^2$ is substituted or unsubstituted $C_6$-$C_{10}$ aryl. In embodiments, the compound has formula (I) and $R^2$ is substituted or unsubstituted phenyl. In embodiments, the compound has formula (I) and $R^2$ is substituted or unsubstituted 5 to 9 membered heteroaryl. In embodiments, the compound has formula (I) and $R^2$ is substituted or unsubstituted 5 to 6 membered heteroaryl. In embodiments, the compound has formula (I) and $R^2$ is substituted or unsubstituted 5 membered heteroaryl. In embodiments, the compound has formula (I) and $R^2$ is substituted or unsubstituted 6 membered heteroaryl. In embodiments, the compound has formula (I) and $R^2$ is substituted or unsubstituted fused ring heteroaryl. In embodiments, the compound has formula (I) and $R^2$ is substituted or unsubstituted 9 membered heteroaryl. In embodiments, the compound has formula (I) and $R^2$ is substituted or unsubstituted 10 membered heteroaryl. In embodiments, the compound has formula (I) and $R^2$ is —$OCH_3$. In embodiments, the compound has formula (I) and $R^2$ is —$CH_2CH_2OH$. In embodiments, the compound has formula (I) and $R^2$ is —$CH_2CH_3$.

In embodiments, the compound has formula (I) and $R^1$ and $R^2$ are joined to form a substituted or unsubstituted heterocloalkyl or a substituted or unsubstituted heteroaryl. In embodiments, the compound has formula (I) and $R^1$ and $R^2$ are joined to form a substituted heterocycloalkyl. In embodiments, the compound has formula (I) and $R^1$ and $R^2$ are joined to form an unsubstituted heterocycloalkyl. In embodiments, the compound has formula (I) and $R^1$ and $R^2$ are joined to form a substituted heteroaryl. In embodiments, the compound has formula (I) and $R^1$ and $R^2$ are joined to form an unsubstituted heteroaryl. In embodiments, the compound has formula (I) and $R^1$ and $R^2$ are joined to form a substituted or unsubstituted 3 to 7 membered heterocycloalkyl. In embodiments, the compound has formula (I) and $R^1$ and $R^2$ are joined to form a substituted or unsubstituted 5 to 7 membered heterocycloalkyl. In embodiments, the compound has formula (I) and $R^1$ and $R^2$ are joined to form a substituted or unsubstituted 5 to 6 membered heterocycloalkyl. In embodiments, the compound has formula (I) and $R^1$ and $R^2$ are joined to form a substituted or unsubstituted 5 to 9 membered heteroaryl. In embodiments, the compound has formula (I) and $R^1$ and $R^2$ are joined to form a substituted or unsubstituted 5 to 6 membered heteroaryl. In embodiments, the compound has formula (I) and $R^1$ and $R^2$ are joined to form a substituted or unsubstituted 5 membered heteroaryl. In embodiments, the compound has formula (I) and $R^1$ and $R^2$ are joined to form a substituted or unsubstituted 6 membered heteroaryl. In embodiments, the compound has formula (I) and $R^1$ and $R^2$ are joined to form a substituted or unsubstituted fused ring heteroaryl. In embodiments, the compound has formula (I) and $R^1$ and $R^2$ are joined to form a substituted or unsubstituted 9 membered heteroaryl. In embodiments, the compound has formula (I) and $R^1$ and $R^2$ are joined to form a substituted or unsubstituted 10 membered heteroaryl. In embodiments, the compound has formula (I) and $R^1$ and $R^2$ are joined to form a substituted piperidinyl. In embodiments, the compound has formula (I) and $R^1$ and $R^2$ are joined to form an unsubstituted piperidinyl.

In embodiments, the compound has formula (I) and $R^2$ is $L^2$-$R^4$. In embodiments, the compound has formula (I) and $L^2$ is unsubstituted $C_1$-$C_{10}$ alkylene. In embodiments, the compound has formula (I) and $L^2$ is unsubstituted $C_1$-$C_8$ alkylene. In embodiments, the compound has formula (I) and $L^2$ is unsubstituted $C_1$-$C_6$ alkylene. In embodiments, the compound has formula (I) and $L^2$ is unsubstituted $C_1$-$C_4$ alkylene. In embodiments, the compound has formula (I) and $L^2$ is unsubstituted $C_1$-$C_3$ alkylene. In embodiments, the compound has formula (I) and $L^2$ is unsubstituted $C_1$-$C_2$ alkylene. In embodiments, the compound has formula (I) and $L^2$ is unsubstituted branched $C_1$-$C_4$ alkylene. In embodiments, the compound has formula (I) and $L^2$ is unsubstituted branched $C_1$-$C_3$ alkylene. In embodiments, the compound has formula (I) and $L^2$ is unsubstituted methylene. In embodiments, the compound has formula (I) and $L^2$ is unsubstituted ethylene. In embodiments, the compound has formula (I) and $L^2$ is a bond. In embodiments, the compound has formula (I) and $R^4$ is independently hydrogen. In embodiments, the compound has formula (I) and $R^4$ is independently halogen. In embodiments, the compound has formula (I) and $R^4$ is independently —$CH_3$. In embodiments, the compound has formula (I) and $R^4$ is independently —$CF_3$. In embodiments, the compound has formula (I) and $R^4$ is independently —OH. In embodiments, the compound has formula (I) and $R^4$ is independently substituted 4-methoxybenzyl. In embodiments, the compound has formula (I) and $R^4$ is independently substituted 4-methoxyphenyl. In embodiments, the compound has formula (I) and $R^4$ is independently substituted pyridyl. In embodiments, the compound has formula (I) and $R^4$ is independently unsubstituted 4-methoxybenzyl. In embodiments, the compound has formula (I) and $R^4$ is independently unsubstituted 4-methoxyphenyl. In embodiments, the compound has formula (I) and $R^4$ is independently unsubstituted pyridyl.

In embodiments, the compound has formula (I) and $R^4$ is substituted or unsubstituted alkyl. In embodiments, the compound has formula (I) and $R^4$ is substituted or unsubstituted heteroalkyl. In embodiments, the compound has formula (I) and $R^4$ is substituted or unsubstituted cycloalkyl. In embodiments, the compound has formula (I) and $R^4$ is substituted or unsubstituted heterocycloalkyl. In embodiments, the compound has formula (I) and $R^4$ is substituted or unsubstituted aryl. In embodiments, the compound has formula (I) and $R^4$ is substituted or unsubstituted heteroaryl. In embodiments, the compound has formula (I) and $R^4$ is unsubstituted alkyl. In embodiments, the compound has formula (I) and $R^4$ is unsubstituted heteroalkyl. In embodiments, the compound has formula (I) and $R^4$ is unsubstituted cycloalkyl. In embodiments, the compound has formula (I) and $R^4$ is unsubstituted heterocycloalkyl. In embodiments, the compound has formula (I) and $R^4$ is unsubstituted aryl. In embodiments, the compound has formula (I) and $R^4$ is unsubstituted heteroaryl. In embodiments, the compound has formula (I) and $R^4$ is substituted or unsubstituted $C_1$-$C_8$ alkyl. In embodiments, the compound has formula (I) and $R^4$ is substituted or unsubstituted $C_1$-$C_6$ alkyl. In embodiments, the compound has formula (I) and $R^4$ is substituted or unsubstituted $C_1$-$C_4$ alkyl. In embodiments, the compound has formula (I) and $R^4$ is substituted or unsubstituted $C_1$-$C_2$ alkyl. In embodiments, the compound has formula (I) and $R^4$ is substituted or unsubstituted methyl. In embodiments, the compound has formula (I) and $R^4$ is unsubstituted methyl. In embodiments, the compound has formula (I) and $R^4$ is substituted or unsubstituted 2 to 8 membered heteroalkyl. In embodiments, the compound has formula (I) and $R^4$ is substituted or unsubstituted 2 to 6 membered heteroalkyl. In embodiments, the compound has formula (I) and $R^4$ is substituted or unsubstituted 2 to 4 membered heteroalkyl. In embodiments, the compound has formula (I) and $R^4$ is substituted or unsubstituted 2 to 3 membered heteroalkyl. In embodiments, the compound has formula (I) and $R^4$ is substituted or unsubstituted $C_3$-$C_7$ cycloalkyl. In embodiments, the compound has formula (I) and $R^4$ is substituted or unsubstituted 3 to 7 membered heterocycloalkyl. In embodiments, the compound has formula (I) and $R^4$ is substituted or unsubstituted 5 to 7 membered heterocycloalkyl. In embodiments, the compound has formula (I) and $R^4$ is substituted or unsubstituted 5 to 6 membered heterocycloalkyl. In embodiments, the compound has formula (I) and $R^4$ is substituted or unsubstituted $C_6$-$C_{10}$ aryl. In embodiments, the compound has formula (I) and $R^4$ is substituted or unsubstituted phenyl. In embodiments, the compound has formula (I) and $R^4$ is substituted or unsubstituted 5 to 9 membered heteroaryl. In embodiments, the compound has formula (I) and $R^4$ is substituted or unsubstituted 5 to 6 membered heteroaryl. In embodiments, the compound has formula (I) and $R^4$ is substituted or unsubstituted 5 membered heteroaryl. In embodiments, the compound has formula (I) and $R^4$ is substituted or unsubstituted 6 membered heteroaryl. In embodiments, the compound has formula (I) and $R^4$ is substituted or unsubstituted fused ring heteroaryl. In embodiments, the compound has formula (I) and $R^4$ is substituted or unsubstituted 9 membered heteroaryl. In embodiments, the compound has formula (I) and $R^4$ is substituted or unsubstituted 10 membered heteroaryl. In embodiments, the compound has formula (I) and $R^4$ is —$OCH_3$. In embodiments, the compound has formula (I) and $R^4$ is —$CH_2CH_2OH$. In embodiments, the compound has formula (I) and $R^4$ is —$CH_2CH_3$.

In embodiments, the compound has formula (Ia) and $L^0$, $L^1$, $L^2$, $R^1$, $R^2$, $R^3$, and $R^4$ of any one of the embodiments for the compound of formula (I) described herein above.

In embodiments, the compound has formula (II) and $L^0$, $L^1$, $R^1$, and $R^3$ of any one of the embodiments for the compound of formula (I) described herein above.

In embodiments, the compound has formula (IIa) and $L^0$, $L^1$, $R^1$, and $R^3$ of any one of the embodiments for the compound of formula (I) described herein above.

In embodiments, the compound has formula (III) and $L^0$, $L^1$, $R^1$, and $R^3$ of any one of the embodiments for the compound of formula (I) described herein above.

In embodiments, the compound has formula (IIIa) and $L^0$, $L^1$, $R^1$, and $R^3$ of any one of the embodiments for the compound of formula (I) described herein above.

In embodiments, the compound has formula (IV) and $L^0$, $L^1$, $L^2$, $R^1$, $R^2$, $R^3$, and $R^4$ of any one of the embodiments for the compound of formula (I) described herein above.

In embodiments, the compound has formula (IVa) and $L^0$, $L^1$, $L^2$, $R^1$, $R^2$, $R^3$, and $R^4$ of any one of the embodiments for the compound of formula (I) described herein above.

In embodiments, the compound is selected from the group consisting of

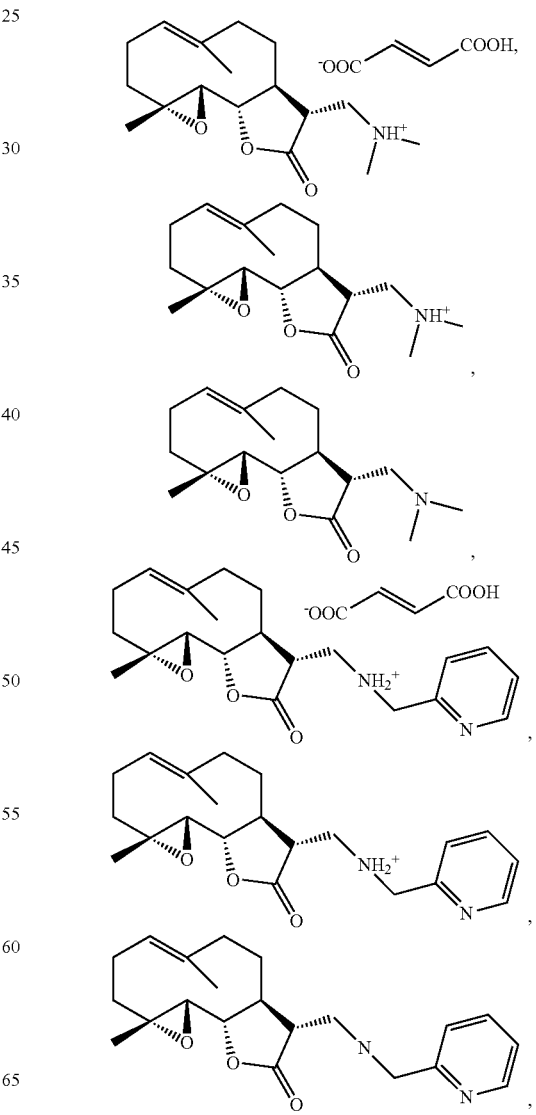

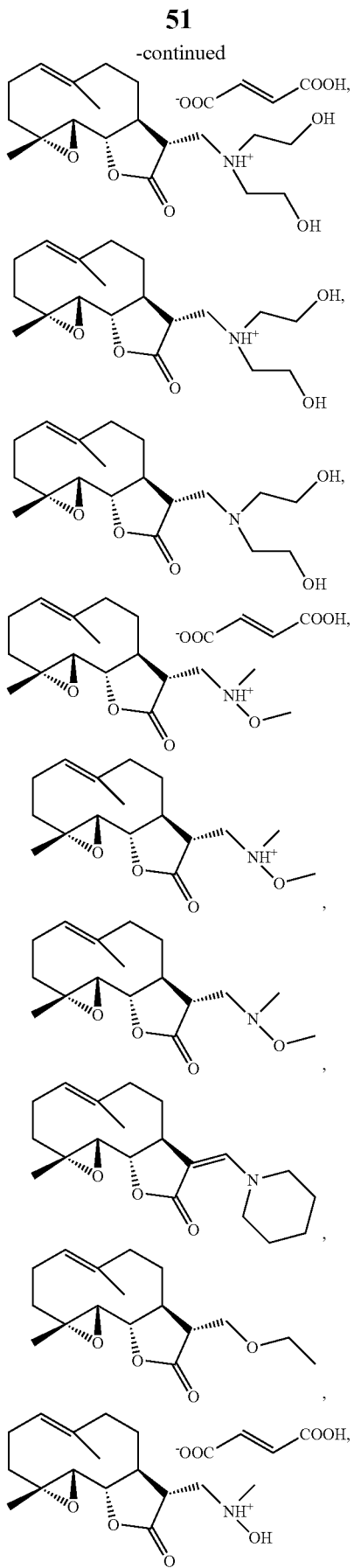

In some embodiments, the compound is selected from the group consisting of JD202, JD203, JD204, JD205, JD206, JD207, JD208, JD209, and JD2010 (including from the neutral compound, protonated cationic compound, and pharmaceutically acceptable salt of the compound). In embodiments, the compound is not JD201 (i.e. DMAPT). In embodiments, the compound is not the neutral form of JD201. In embodiments, the compound is not a protonated cationic form of JD201. In embodiments, the compound is not a fumarate salt of JD201. In embodiments, the compound is not a pharmaceutically acceptable salt of JD201.

In embodiments, the compound is not a compound of formula (I) or (Ia) wherein $L^0$ is unsubstituted methylene and $R^1$ and $R^2$ are independently hydrogen or unsubstituted methyl or ethyl. In embodiments, the compound is not a compound of formula (I) or (Ia) wherein $L^0$ is unsubstituted methylene and $R^1$ and $R^2$ are unsubstituted ethyl. In embodiments, the compound is not a compound of formula (I) or (Ia) wherein $L^0$ is unsubstituted methylene and $R^1$ and $R^2$ are independently hydrogen or unsubstituted $C_1$-$C_3$ alkyl. In embodiments, the compound is not a compound of formula (I) or (Ia) wherein $L^0$ is unsubstituted methylene and $R^1$ and $R^2$ are independently hydrogen or unsubstituted linear $C_1$-$C_3$ alkyl. In embodiments, the compound is not a compound of formula (I) or (Ia) wherein $L^0$ is unsubstituted methylene and $R^1$ and $R^2$ are independently hydrogen or unsubstituted $C_1$-$C_4$ alkyl. In embodiments, the compound is not a compound of formula (I) or (Ia) wherein $L^0$ is unsubstituted methylene and $R^1$ and $R^2$ are independently hydrogen or unsubstituted linear $C_1$-$C_4$ alkyl. In embodiments, the compound is not a compound of formula (I) or (Ia) wherein $L^0$ is unsubstituted methylene and $R^1$ and $R^2$ are independently hydrogen or halogen substituted methyl or unsubstituted methyl. In embodiments, the compound is not a compound of formula (I) or (Ia) wherein $L^0$ is unsubstituted methylene and $R^1$ and $R^2$ are independently hydrogen or halogen substituted $C_1$-$C_2$ alkyl or unsubstituted $C_1$-$C_2$ alkyl. In embodiments, the compound is not a compound of formula (I) or (Ia) wherein $L^0$ is unsubstituted methylene and $R^1$ and $R^2$ are independently hydrogen or halogen substituted $C_1$-$C_3$ alkyl or unsubstituted $C_1$-$C_3$ alkyl. In embodiments, the compound is not a compound of formula (I) or (Ia) wherein $L^0$ is unsubstituted methylene and $R^1$ and $R^2$ are independently hydrogen or unsubstituted methyl or methyl substituted with —$CF_3$, —$CCl_3$, —CN, —S(O)$CH_3$, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)OH, or —NHOH. In embodiments, the compound is not a compound of formula (I) or (Ia) wherein $L^0$ is unsubstituted methylene and $R^1$ and $R^2$ are independently hydrogen, unsubstituted $C_1$-$C_2$ alkyl or $C_1$-$C_2$ alkyl substituted with —$CF_3$, —$CCl_3$, —CN, —S(O)$CH_3$, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)OH, or —NHOH.

In embodiments, the compound is not a compound of formula (I) or (Ia) wherein $L^0$ is a bond and $R^1$ and $R^2$ are independently hydrogen or unsubstituted methyl or ethyl. In embodiments, the compound is not a compound of formula (I) or (Ia) wherein $L^0$ is a bond and $R^1$ and $R^2$ are unsubstituted ethyl. In embodiments, the compound is not a compound of formula (I) w or (Ia) herein $L^0$ is a bond and $R^1$ and $R^2$ are independently hydrogen or unsubstituted $C_1$-$C_3$ alkyl. In embodiments, the compound is not a compound of formula (I) or (Ia) wherein $L^0$ is a bond and $R^1$ and $R^2$ are independently hydrogen or unsubstituted linear $C_1$-$C_3$ alkyl. In embodiments, the compound is not a compound of formula (I) w or (Ia) herein $L^0$ is a bond and $R^1$ and $R^2$ are independently hydrogen or unsubstituted $C_1$-$C_4$ alkyl. In embodiments, the compound is not a compound of formula (I) or (Ia) wherein $L^0$ is a bond and $R^1$ and $R^2$ are independently hydrogen or unsubstituted linear $C_1$-$C_4$ alkyl. In embodiments, the compound is not a compound of formula (I) or (Ia) wherein $L^0$ is a bond and $R^1$ and $R^2$ are independently hydrogen or halogen substituted methyl or unsubstituted methyl. In embodiments, the compound is not a compound of formula (I) w or (Ia) herein $L^0$ is a bond and $R^1$ and $R^2$ are independently hydrogen or halogen substituted $C_1$-$C_2$ alkyl or unsubstituted $C_1$-$C_2$ alkyl. In embodiments, the compound is not a compound of formula (I) or (Ia) wherein $L^0$ is a bond and $R^1$ and $R^2$ are independently hydrogen or halogen substituted $C_1$-$C_3$ alkyl or unsubstituted $C_1$-$C_3$ alkyl. In embodiments, the compound is not a compound of formula (I) or (Ia) wherein $L^0$ is a bond and $R^1$ and $R^2$ are independently hydrogen or unsubstituted methyl or methyl substituted with —$CF_3$, —$CCl_3$, —CN, —S(O)$CH_3$, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)OH, or —NHOH.

In embodiments, the compound is not a compound of formula (I) or (Ia) wherein $L^0$ is unsubstituted $C_1$-$C_2$ alkylene and $R^1$ and $R^2$ are independently hydrogen or unsubstituted methyl or ethyl. In embodiments, the compound is not a compound of formula (I) or (Ia) wherein $L^0$ is independently hydrogen or unsubstituted $C_1$-$C_2$ alkylene and $R^1$ and $R^2$ are unsubstituted ethyl. In embodiments, the compound is not a compound of formula (I) or (Ia) wherein $L^0$ is unsubstituted $C_1$-$C_2$ alkylene and $R^1$ and $R^2$ are independently hydrogen or unsubstituted $C_1$-$C_3$ alkyl. In embodiments, the compound is not a compound of formula (I) w or (Ia) herein $L^0$ is unsubstituted $C_1$-$C_2$ alkylene and $R^1$ and $R^2$ are independently hydrogen or unsubstituted linear $C_1$-$C_3$ alkyl. In embodiments, the compound is not a compound of formula (I) or (Ia) wherein $L^0$ is unsubstituted $C_1$-$C_2$ alkylene and $R^1$ and $R^2$ are independently hydrogen or unsubstituted $C_1$-$C_4$ alkyl. In embodiments, the compound is not a compound of formula (I) or (Ia) herein $L^0$ is unsubstituted $C_1$-$C_2$ alkylene and $R^1$ and $R^2$ are independently hydrogen or unsubstituted linear $C_1$-$C_4$ alkyl. In embodiments, the compound is not a compound of formula (I) or (Ia) wherein $L^0$ is unsubstituted $C_1$-$C_2$ alkylene and $R^1$ and $R^2$ are independently hydrogen or halogen substituted methyl or unsubstituted methyl. In embodiments, the compound is not a compound of formula (I) or (Ia) wherein $L^0$ is unsubstituted $C_1$-$C_2$ alkylene and $R^1$ and $R^2$ are independently hydrogen or halogen substituted $C_1$-$C_2$ alkyl or unsubstituted $C_1$-$C_2$ alkyl. In embodiments, the compound is not a compound of formula (I) or (Ia) wherein $L^0$ is unsubstituted $C_1$-$C_2$ alkylene and $R^1$ and $R^2$ are independently hydrogen or halogen substituted $C_1$-$C_3$ alkyl or unsubstituted $C_1$-$C_3$ alkyl. In embodiments, the compound is not a compound of formula (I) or (Ia) wherein $L^0$ is unsubstituted $C_1$-$C_2$ alkylene and $R^1$ and $R^2$ are independently hydrogen or unsubstituted methyl or methyl substituted with —$CF_3$, —$CCl_3$, —CN, —S(O)$CH_3$, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)OH, or —NHOH.

III. Pharmaceutical Compositions

In another aspect is provided a pharmaceutical composition including a pharmaceutically acceptable excipient and a compound, or a pharmaceutically acceptable salt thereof, as described herein (including embodiments).

In embodiments of the pharmaceutical compositions, the compound (e.g. as described herein, including embodiments), or pharmaceutically acceptable salt thereof, is included in a therapeutically effective amount. In embodiments of the pharmaceutical compositions, the pharmaceutical composition includes a second agent (e.g. therapeutic agent). In embodiments of the pharmaceutical compositions, the pharmaceutical composition includes a second agent (e.g. therapeutic agent) in a therapeutically effective amount. In embodiments, the second agent is an agent for treating cancer (e.g. leukemia, lung cancer, epidermoid carcinoma (i.e. squamous-cell carcinoma), fibrosarcoma, liver cancer (e.g. hepatocellular carcinoma), prostate cancer, kidney cancer (e.g. renal cell carcinoma or urothelial cell carcinoma), lymphoma, breast cancer, urinary bladder cancer, prostate cancer, or therapy resistant cancer). In embodiments, the second agent is an anti-cancer agent. In embodiments, the second agent is a chemotherapeutic. In embodiments, the second agent is a hormonal therapeutic agent. In embodiments, the second agent is a platinum-based compound. In embodiments, the second agent is tamoxifen. In embodiments, the second agent is trastuzumab. In embodiments, the second agent is cisplatin. In embodiments, the second agent is carboplatin. In embodiments, the second agent is an agent for treating leukemia. In embodiments, the second agent is an agent for treating breast cancer. In embodiments, the second agent is an agent for treating lung cancer. In embodiments, the second agent is an agent for treating non-small cell lung cancer. In embodiments, the second agent is an agent for treating a therapy resistant cancer. In embodiments, the second agent is an agent for reducing NFκB phosphorylation. In embodiments, the second agent is an agent for inhibiting a pathway activated by NFκB phosphorylation. In embodiments, the second agent is an agent for reducing NFκB activity. In embodiments, the second agent is an agent for treating tamoxifen resistant cancer. In embodiments, the second agent is an agent for treating cisplatin resistant cancer. In embodiments, the second agent is an agent for treating carboplatin resistant cancer. In embodiments, the second agent is an agent for treating trastuzumab resistant cancer. In embodiments, the second agent is an agent for treating hormonal therapy resistant cancer. In embodiments, the second agent is an agent for treating platinum-based compound resistant cancer. In embodiments, the second agent is an agent for treating a hyperproliferative disease (e.g. cancer or a non-malignant hyperproliferative disease). In embodiments, the second agent is an agent for treating a hamartomatous lesion. In embodiments, the second agent is an agent for treating angiomyolipoma. In embodiments, the second agent is an agent for treating lymphangioleiomyomatosis. In embodiments, the second agent is an agent for treating tuberous sclerosis complex. In embodiments, the second agent is an agent for treating a hamartia. In embodiments, the second agent is an agent for treating a hamartoma. In embodiments, the second agent is an agent for increasing the activity of a pathway including TSC1. In embodiments, the second agent is an agent for increasing TSC1 activity. In embodiments, the second agent is an agent for increasing the activity of a pathway including TSC2. In embodiments, the second agent is an agent for increasing TSC2 activity. In embodiments, the second agent is an agent for decreasing the activity of a pathway including mTOR. In embodiments, the second agent is an agent for decreasing mTOR activity. In embodiments, the second agent is an agent for decreasing the activity of a pathway including mTORC1. In embodiments, the second agent is an agent for decreasing mTORC1 activity.

In some embodiments, the compound is a compound described in an example, a table, a figure, or a claim. In some embodiments, the compound is a compound described in the Compounds section above.

IV. Methods of Treatment

In another aspect is provided a method of treating cancer in a patient in need of the treatment, the method including administering a therapeutically effective amount of a compound, or a pharmaceutically acceptable salt thereof, as described herein (including embodiments) to the patient.

In embodiments, the cancer is breast cancer. In embodiments, the cancer is a therapy resistant breast cancer. In embodiments, the cancer is a hormonal therapy resistant breast cancer. In embodiments, the cancer is tamoxifen resistant breast cancer. In embodiments, the cancer is trastuzumab (i.e. Herceptin™) resistant breast cancer. In embodiments, the cancer is breast cancer resistant to an aromatase inhibitor. In embodiments, the cancer is fulvestrant resistant breast cancer. In embodiments, the cancer is exemestane resistant breast cancer. In embodiments, the cancer is anastrozole resistant breast cancer. In embodiments, the cancer is aminoglutethimide resistant breast cancer. In embodiments, the cancer is testolactone resistant breast cancer. In embodiments, the cancer is letrozole resistant breast cancer. In embodiments, the cancer is vorozole resistant breast cancer. In embodiments, the cancer is formestane resistant breast cancer. In embodiments, the cancer is fadrozole resistant breast cancer. In embodiments, the cancer is metastatic breast cancer. In embodiments, the cancer is ER positive breast cancer. In embodiments, the cancer is ER negative breast cancer. In embodiments, the cancer is breast cancer resistant to an anti-cancer agent. In embodiments, the cancer is breast cancer expressing a high level of HER2 (e.g. relative to a control such as a non-cancerous sample).

In embodiments, the cancer is lung cancer. In embodiments, the cancer is non-small cell lung cancer (NSCLC). In embodiments, the cancer is a therapy resistant NSCLC. In embodiments, the cancer is oxaliplatin resistant NSCLC. In embodiments, the cancer is cisplatin resistant NSCLC. In embodiments, the cancer is NSCLC resistant to a platinum-based compound. In embodiments, the cancer is carboplatin resistant NSCLC. In embodiments, the cancer is lung cancer resistant to a platinum-based compound. In embodiments, the cancer is metastatic lung cancer. In embodiments, the cancer is metastatic NSCLC. In embodiments, the cancer is lung cancer resistant to an anti-cancer agent. In embodiments, the cancer is NSCLC resistant to an anti-cancer agent. In embodiments, the cancer is resistant to a taxane. In embodiments, the cancer is resistant to a hormonal therapy. In embodiments, the cancer is resistant to a platinum-based compound. In embodiments, the cancer is resistant to docetaxel.

In embodiments, the cancer is urinary bladder cancer. In embodiments, the cancer is a therapy resistant urinary bladder cancer. In embodiments, the cancer is prostate cancer. In embodiments, the cancer is a therapy resistant prostate cancer. In embodiments, the cancer is leukemia. In embodiments, the cancer is a therapy resistant leukemia. In embodiments, the cancer is lymphoma. In embodiments, the cancer is a therapy resistant lymphoma. In embodiments, the cancer is epidermoid carcinoma (i.e. squamous-cell carcinoma). In embodiments, the cancer is a therapy resistant epidermoid carcinoma (i.e. squamous-cell carcinoma). In embodiments, the cancer is fibrosarcoma. In embodiments, the cancer is a therapy resistant fibrosarcoma. In embodiments, the cancer is liver cancer (e.g. hepatocellular carcinoma). In embodiments, the cancer is a therapy resistant liver cancer (e.g. hepatocellular carcinoma). In embodiments, the cancer is kidney cancer (e.g. renal cell carcinoma or urothelial cell carcinoma). In embodiments, the cancer is a therapy resistant kidney cancer (e.g. renal cell carcinoma or urothelial cell carcinoma). In embodiments, the cancer is a hematopoietic cell cancer. In embodiments, the cancer is a therapy resistant hematopoietic cell cancer. In embodiments, the cancer is metastatic cancer. In embodiments, the cancer is resistant to an anti-cancer agent.

In another aspect is provided a method of treating a non-malignant hyperproliferative disease in a patient in need of the treatment, the method including administering a therapeutically effective amount of a compound, or a pharmaceutically acceptable salt thereof, as described herein (including embodiments) to the patient.

In embodiments, the non-malignant hyperproliferative disease is a hamartomatous lesion. In embodiments, the non-malignant hyperproliferative disease is angiomyolipoma. In embodiments, the non-malignant hyperproliferative disease is lymphangioleiomyomatosis. In embodiments, the non-malignant hyperproliferative disease is tuberous sclerosis complex. In embodiments, the non-malignant hyperproliferative disease is a hamartia. In embodiments, the non-malignant hyperproliferative disease is a hamartoma.

In embodiments of the methods of treating a disease (e.g. cancer or a non-malignant hyperproliferative disease), the compound, or pharmaceutically acceptable salt thereof, is provided as a pharmaceutical composition (as described herein, including embodiments).

In embodiments, the compound, or a pharmaceutically acceptable salt thereof, is co-administered with a second agent (e.g. therapeutic agent). In embodiments, the compound, or a pharmaceutically acceptable salt thereof, is co-administered with a second agent (e.g. therapeutic agent), which is administered in a therapeutically effective amount. In embodiments, the second agent is an agent for treating cancer (e.g. leukemia, lung cancer, epidermoid carcinoma (i.e. squamous-cell carcinoma), fibrosarcoma, liver cancer (e.g. hepatocellular carcinoma), prostate cancer, kidney cancer (e.g. renal cell carcinoma or urothelial cell carcinoma), lymphoma, breast cancer, urinary bladder cancer, prostate cancer, or therapy resistant cancer). In embodiments, the second agent is an anti-cancer agent. In embodiments, the second agent is a chemotherapeutic. In embodiments, the second agent is a hormonal therapeutic agent. In embodiments, the second agent is a platinum-based compound. In embodiments, the second agent is tamoxifen. In embodiments, the second agent is trastuzumab. In embodiments, the second agent is cisplatin. In embodiments, the second agent is carboplatin. In embodiments, the second agent is an agent for treating leukemia. In embodiments, the second agent is an agent for treating breast cancer. In embodiments, the second agent is an agent for treating lung cancer. In embodiments, the second agent is an agent for treating non-small cell lung cancer. In embodiments, the second agent is an agent for treating a therapy resistant cancer (e.g. a therapy resistant leukemia, lung cancer, epidermoid carcinoma (i.e. squamous-cell carcinoma), fibrosarcoma, liver cancer (e.g. hepatocellular carcinoma), prostate cancer, kidney cancer (e.g. renal cell carcinoma or urothelial cell carcinoma), lymphoma, breast cancer, urinary bladder cancer, or prostate cancer). In embodiments, the second agent is an agent for reducing NFκB phosphorylation. In embodiments, the second agent is an agent for inhibiting a pathway activated by NFκB phosphorylation. In embodiments, the second agent is an agent for reducing NFκB activity. In embodiments, the second agent is an agent for treating tamoxifen resistant cancer. In embodiments, the second agent is an agent for treating cisplatin resistant cancer. In embodiments, the second agent is an agent for treating carboplatin resistant cancer. In embodiments, the second agent is an agent for treating trastuzumab resistant cancer. In embodiments, the second agent is an agent for treating hormonal therapy resistant cancer. In embodiments, the second agent is an agent for treating platinum-based compound resistant cancer. In embodiments, the second agent is an agent for treating a hyperproliferative disease (e.g. cancer or a non-malignant hyperproliferative disease). In embodiments, the second agent is an agent for treating a hamartomatous lesion. In embodiments, the second agent is an agent for treating angiomyolipoma. In embodiments, the second agent is an agent for treating lymphangioleiomyomatosis. In embodiments, the second agent is an agent for treating tuberous sclerosis complex. In embodiments, the second agent is an agent for treating a hamartia. In embodiments, the second agent is an agent for treating a hamartoma. In embodiments, the second agent is an agent for increasing the activity of a pathway including TSC1. In embodiments, the second agent is an agent for increasing TSC1 activity. In embodiments, the second agent is an agent for increasing the activity of a pathway including TSC2. In embodiments, the second agent is an agent for increasing TSC2 activity. In embodiments, the second agent is an agent for decreasing the activity of a pathway including mTOR. In embodiments, the second agent is an agent for decreasing mTOR activity. In embodiments, the second agent is an agent for decreasing the activity of a pathway including mTORC1. In embodiments, the second agent is an agent for decreasing mTORC1 activity.

In some embodiments, the compound is a compound described in an example, a table, a figure, or a claim. In some embodiments, the compound is a compound described in the Compounds section above.

V. Methods of Modulating a Target

In another aspect is provided a method of inhibiting cancer cell growth or survival including contacting the cell with an effective amount of a compound, or a pharmaceutically acceptable salt thereof, as described herein (including embodiments).

In embodiments, the cancer cell is a stem cell. In embodiments, the cancer cell is a progenitor cell. In embodiments, the cancer cell is a cancer (e.g. leukemia, lung cancer, epidermoid carcinoma (i.e. squamous-cell carcinoma), fibrosarcoma, liver cancer (e.g. hepatocellular carcinoma), prostate cancer, kidney cancer (e.g. renal cell carcinoma or urothelial cell carcinoma), lymphoma, breast cancer, urinary bladder cancer, prostate cancer, or therapy resistant cancer) stem cell. In embodiments, the cancer cell is a cancer (e.g. leukemia, lung cancer, epidermoid carcinoma (i.e. squamous-cell carcinoma), fibrosarcoma, liver cancer (e.g. hepatocellular carcinoma), prostate cancer, kidney cancer (e.g. renal cell carcinoma or urothelial cell carcinoma), lymphoma, breast cancer, urinary bladder cancer, prostate cancer, or therapy resistant cancer) progenitor cell. In embodiments, the cancer cell is a lung cancer stem cell. In embodiments, the cancer cell is a lung cancer progenitor cell. In embodiments, the cancer cell is a breast cancer stem cell. In embodiments, the cancer cell is a breast cancer progenitor cell. In embodiments, the compound, or a pharmaceutically acceptable salt thereof, (as described herein, including embodiments) increases apoptosis in the cancer cell. In embodiments, the compound, or a pharmaceutically acceptable salt thereof, (as described herein, including embodiments) induces apoptosis in the cancer cell.

In another aspect is provided a method of modulating the level of activity of NF-κB in a cell including contacting the cell with an effective amount of a compound, or a pharmaceutically acceptable salt thereof, as described herein (including embodiments).

In embodiments of the methods of modulating NFκB, modulating is inhibiting the level of activity of NFκB. In embodiments of the methods of modulating NFκB, modulating is increasing the level of activity of NFκB. In embodiments of the methods of modulating NFκB, the compound, or pharmaceutically acceptable salt thereof, is provided as a pharmaceutical composition (as described herein, including embodiments). In embodiments of the method of modulating NFκB, the method includes contacting NFκB with a compound as described herein (including embodiments). In embodiments of the method of modulating NFκB, the method includes contacting a component of a pathway including NFκB with a compound as described herein (including embodiments). In embodiments of the methods of modulating NFκB, modulating is inhibiting the phosphorylation of NFκB. In embodiments of the methods of modulating NFκB, modulating is inhibiting a pathway activated by the phosphorylation of NFκB. In embodiments of the methods of modulating NFκB, modulating is inhibiting a pathway including phosphorylated NFκB.

In another aspect is provided a method of modulating the level of activity of TSC1 in a cell including contacting the cell with an effective amount of a compound, or a pharmaceutically acceptable salt thereof, as described herein (including embodiments).

In embodiments of the methods of modulating TSC1, modulating is inhibiting the level of activity of TSC1. In embodiments of the methods of modulating TSC1, modulating is increasing the level of activity of TSC1. In embodiments of the methods of modulating TSC1, the compound, or pharmaceutically acceptable salt thereof, is provided as a pharmaceutical composition (as described herein, including embodiments). In embodiments of the method of modulating TSC1, the method includes contacting TSC1 with a compound as described herein (including embodiments). In embodiments of the method of modulating TSC1, the method includes modulating the level of activity or amount of a component in a pathway including TSC1.

In another aspect is provided a method of modulating the level of activity of TSC2 in a cell including contacting the cell with an effective amount of a compound, or a pharmaceutically acceptable salt thereof, as described herein (including embodiments).

In embodiments of the methods of modulating TSC2, modulating is inhibiting the level of activity of TSC2. In embodiments of the methods of modulating TSC2, modulating is increasing the level of activity of TSC2. In embodiments of the methods of modulating TSC2, the compound, or pharmaceutically acceptable salt thereof, is provided as a pharmaceutical composition (as described herein, including embodiments). In embodiments of the method of modulating TSC2, the method includes contacting TSC2 with a compound as described herein (including embodiments). In embodiments of the method of modulating TSC2, the method includes modulating the level of activity or amount of a component in a pathway including TSC2.

In another aspect is provided a method of modulating the level of activity of mTOR in a cell including contacting the cell with an effective amount of a compound, or a pharmaceutically acceptable salt thereof, as described herein (including embodiments).

In embodiments of the methods of modulating mTOR, modulating is inhibiting the level of activity of mTOR. In embodiments of the methods of modulating mTOR, modulating is increasing the level of activity of mTOR. In embodiments of the methods of modulating mTOR, the compound, or pharmaceutically acceptable salt thereof, is provided as a pharmaceutical composition (as described herein, including embodiments). In embodiments of the method of modulating mTOR, the method includes contacting mTOR with a compound as described herein (including embodiments). In embodiments of the method of modulating mTOR, the method includes modulating the level of activity or amount of a component in a pathway including mTOR. In embodiments of the methods of modulating mTOR, modulating is inhibiting the level of activity of mTORC1. In embodiments of the methods of modulating mTOR, modulating is increasing the level of activity of mTORC1. In embodiments of the methods of modulating mTOR, the compound, or pharmaceutically acceptable salt thereof, is provided as a pharmaceutical composition (as described herein, including embodiments). In embodiments of the method of modulating mTOR, the method includes contacting mTORC1 with a compound as described herein (including embodiments). In embodiments of the method of modulating mTOR, the method includes modulating the level of activity or amount of a component in a pathway including mTORC1.

In embodiments, the compound, or a pharmaceutically acceptable salt thereof, is co-administered with a second agent (e.g. therapeutic agent). In embodiments, the compound, or a pharmaceutically acceptable salt thereof, is co-administered with a second agent (e.g. therapeutic agent), which is administered in a therapeutically effective amount. In embodiments, the second agent is a second agent as described herein, including in the method of treatment section above and including embodiments.

In some embodiments, the compound is a compound described in an example, a table, a figure, or a claim. In some embodiments, the compound is a compound described in the Compounds section above.

Lung cancer is the leading cause of cancer death in men and women worldwide. The poor prognosis of advanced non-small cell lung cancer (NSCLC) is due, in part, to emergence of tumor resistance to chemotherapy. Recent data indicate that human tumors, including NSCLC, contain a small subset of cancer stem/progenitor cells (CSC) responsible for drug resistance and tumor maintenance. If such minute subsets of CSC drive tumor formation and drug resistance, therapies targeting the bulk tumor mass but not CSC will fail. We now confirm identification of subpopulations of chemotherapy-resistant human NSCLC cells with enrichment for CSC biomarkers and exhibiting significant CSC activity. We identified CD133+/ALDH+ tumor stem/progenitor cells from human lung cancer cells in vitro using established Aldefluor assays in combination with labeled anti-CD 133 antibodies. Estrogen, a known risk factor for lung cancer progression, stimulated a modest increase in the numbers of CSC. In contrast to control CD133−/ALDH− tumor cell subsets, CSC subpopulations grew as tumor spheres and maintained self-renewal capacity in vitro and exhibited a greater tumorigenic capability than non-CSC subsets in vivo, properties indicative of CSC. Furthermore, resistance of CSC-like cells to cisplatin (a standard chemotherapy for NSCLC treatment) was fully reversed by treatment with parthenolide (PTL), a naturally-occurring sesquiterpene lactone compound with strong antitumor activity in leukemia and prostate cancer, while sparing normal cells. The antitumor effect of PTL may be due to its action as a potent inhibitor of nuclear factor-KB (NF-κB), which is markedly activated by chemotherapy. To target CSC and suppress tumor progression, we synthesized and tested novel analogs of PTL with improved antitumor properties and aqueous solubility. PTL analogs inhibit proliferation of H157 NSCLC cells using both bulk cell preparations and CSC-subpopulations, with effects significantly different from control at P<0.05. Dose-dependent increments of PTL analogs increase apoptosis of CSC when compared with bulk cells. Moreover, PTL analogs inhibit cell proliferation of H23, A549 and H1975 NSCLC cells with known resistance to cisplatin (P<0.01). These compounds were able to sensitize cells to cisplatin-induced cytotoxicity (P<0.01) when cells were exposed to sub-optimal concentrations of cisplatin. Using Western blots, we find that PTL congeners inhibit phosphorylation of the p65 subunit of phospho-NF-κB and activation of IKKa/β. Thus, targeted inhibition of NF-κB may reverse tumor drug resistance by interfering with known NF-κB actions to regulate genes involved in proliferation, DNA damage response, antiapoptosis and angiogenesis. Further development of PTL analogs as therapeutics may lead to new strategies to treat NSCLC in the clinic.

Chemical modification of parthenolide to enhance its solubility allows the compound to better suppress not only human lung tumor growth in vitro but also tumor xenograft growth in vivo (2, 10). We have chemically synthesized soluble drug-like parthenolide derivatives and tested them in NSCLC cell lines. These novel analogues are able to suppress NSCLC cell proliferation and inhibit activation of NFκB. This invention provides a new method to treat NSCLC and possibly other types of cancers through inhibition of NFκB signaling and activation of cell death pathways. Orally available drug-like parthenolide derivatives could be used as new therapeutics for the treatment of lung cancer and potentially other solid tumors.

An aminoanalog of parthenolide, dimethylaminoparthenolide (DMAPT/LC-1 was demonstrated to have 70% oral bioavaliability, plasma concentrations of 40 micromolar after oral administration and an acceptable toxicology profile (3). DMAPT appears to be active against leukemia, lung, urinary bladder and prostate cancer cells, including cancer stem cells (2, 3-5). We have synthesized novel derivatives of the parental parthenolide and DMAPT that we find to be very active in inhibiting proliferation of NSCLC and inducing cancer stem cell death.

We have synthesized parthenolide derivatives that are unique in their structures and activity. These novel compounds have shown to be equally or more effective than DMAPT and more water-soluble than DMAPT (1). At present, there are no drug-like parthenolides used for treatment of lung cancer or other solid tumors. Development of novel therapies for treatment of lung cancer and other solid tumors are urgently needed. Of note, there are currently no targeted therapies for NSCLC, the predominant form of lung cancer. Identification of a new targeted therapeutic for lung and other solid tumors would be significant. It is notable that a large proportion of antitumor therapeutics currently used in the clinic were developed from natural products and from investigation of the use of herbal constituents in traditional medicines. Aminoparthenolide analogues with oral bioavailability induce cancer cell death without having detrimental effects on normal cells. This invention is intended to advance novel chemical compounds with clinical-translational potential for the benefit of patients with NSCLC and other solid tumors. Given the large population of patients afflicted with NSCLC worldwide, the need for a new treatment strategy in the clinic is urgent. The compounds disclosed herein may be effective in treating other types of solid malignancies such as breast and prostate cancer. Compounds described herein may be useful in cancer prevention among individuals at high risk for cancer (for example, those with a significant history of tobacco smoking or evidence of premalignant lung lesions). Oral administration of the novel compounds may be used in clinical practice.

We have developed a set of novel analogues of parthenolide which have both improved aqueous solubility and antitumor properties. An extensive structure-activity study was done to investigate parthenolide and its analogues. These new compounds are more water soluble than the parental parthenolide and even though the structure is altered significantly, they retain enhanced activity over the parental compound. We have developed some analogues (such as JD203) with improved water solubility and strong anticancer activity as compared to other known parthenolide derivatives such as DMAPT (JD201) (1, 2). These water-soluble compounds, for example analog JD206, may be conjugated to sugars or peptides that may be selectively targeted to cancer cells, particularly cancer stem cells.

Novel parthenolide derivatives for treatment of NSCLC are being tested in a panel of cell line models of lung cancer. In addition, novel parthenolide derivatives are being tested for their toxicity on normal cells such as blood vessels cells (human umbilical vein endothelial cells) and lung cells (human bronquial epithelial cells). Analogues of the present invention may be used alone or in combination with standard chemotherapy treatments currently used in the clinic, such as cisplatin, carboplatin and taxanes. Analogues of the present invention may be used in the treatment or prevention of lung cancer.

Figure 13:
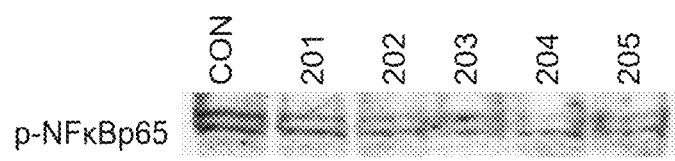
FIG. 13. Parthenolide analogues inhibit phosphorylation of NF-κB/p65; H23 cells were treated with vehicle (CON) or 10 mM parthenolide analogs (JD201, 202, 203, 204 and 205); after 60 min, Western blots were done using anti-phospho-NFκB/p65 antibody (Cell Signaling); membranes were stripped, re-probed with antibody to total NFκB/p65 (not shown); similar findings have been obtained using human breast tumor cells in vitro.

We determined that parthenolide analogues prepared in our laboratory inhibit phosphorylation of NF-κB/p65. Hence, H23 lung tumor cells were treated with vehicle (CON) or 10 mM parthenolide analogs (JD201, 202, 203, 204 and 205). After 60 min, Western blots were done using anti-phospho-NFκB/p65 antibody (Cell Signaling). Results are shown in FIG. 13.

Lung Cancer has one of the lowest survival outcomes of all cancers with overall 5-year survival rate for non-small cell lung cancer at 15%. The poor prognosis of advanced non-small cell lung cancer (NSCLC) is due, in part, to emergence of tumor resistance to chemotherapy. Human tumors contain a small subset of cancer stem cells (CSC) responsible for drug resistance and tumor maintenance. It is important to design effective therapies to target CSC. Parthenolide and analogues enhanced sensitivity to chemotherapy in A549 NSCLC cells by blocking NF-κB signaling. Aberrant activation of NF-κB has been proposed as the major cause of chemoresistance in lung cancer. Parthenolides combined with low-dose chemotherapy may limit cytotoxicity and elicit enhanced antitumor efficacy by blocking NF-κB activation in lung cancer therapy. Subsets of drug-resistant CSCs are present in lung tumors and this resistance phenotype associates with NF-kB signaling to block apoptosis. Use of parthenolide analogues to selectively inhibit NF-κB and reverse antiapoptotic activity may be a new strategy to eradicate lung cancer. Parthenolide analogues inhibit growth of male and female NSCLC cells in vitro. NSCLC cells can be sensitized to cisplatin mediated cytotoxicity by parthenolide derivatives. Cancer stem/progenitor cells occur in the bulk of NSCLC cells and have a response to estrogen exposure. ALDH+/CD133+ tumor cell subpopulations form tumor spheres and exhibit self-renewal properties. Parthenolides inhibit phosphorylation of the p65 subunit of NFκB. Parthenolide analogues block activation of NFκB and are active in restoring breast tumor responses to hormonal and Trastuzumab therapies, thereby potentially helping to improve patient outcomes. Parthenolide analogues are active in suppressing lung cancer stem cells and have the potential to reverse tumor recurrences after primary therapy.

VI. Additional Embodiments

1. A compound, or a pharmaceutically acceptable salt thereof, wherein the compound has a formula selected from the group consisting of:

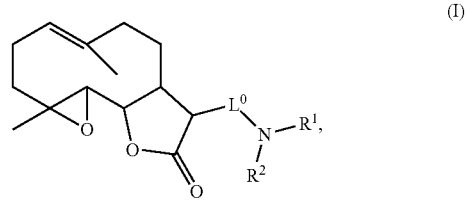

(I)

63

-continued

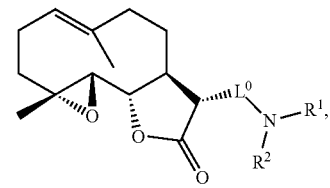
(II)

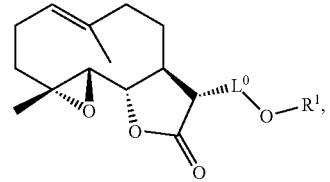
(III)

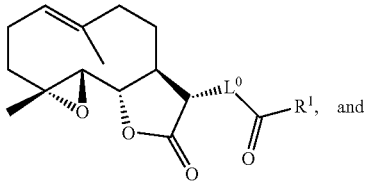
(IV)

wherein, $L^0$ is independently a bond or an unsubstituted $C_1$-$C_{10}$ alkylene; and $R^1$ and $R^2$ are independently hydrogen, —OH, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; where $R^1$ and $R^2$ may optionally be joined to form a substituted or unsubstituted heterocycloalkyl or a substituted or unsubstituted heteroaryl.

2. The compound, or a pharmaceutically acceptable salt thereof, of embodiment 1, wherein the compound, or a pharmaceutically acceptable salt thereof, is not

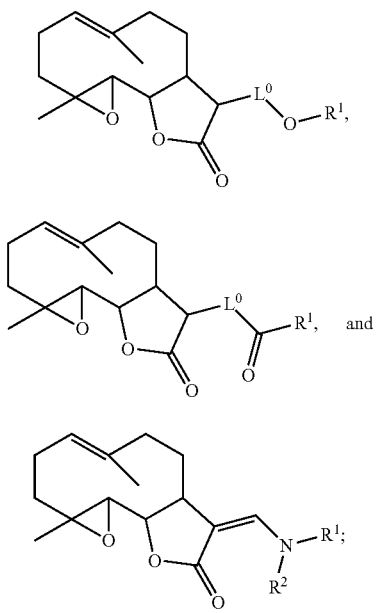

3. The compound, or a pharmaceutically acceptable salt thereof, of any one of embodiments 1 to 2, wherein the compound has a formula selected from the group consisting of:

64

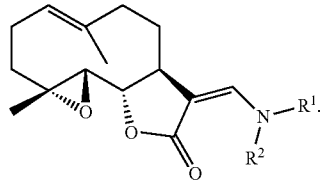
(Ia)

(IIa)

(IIIa)

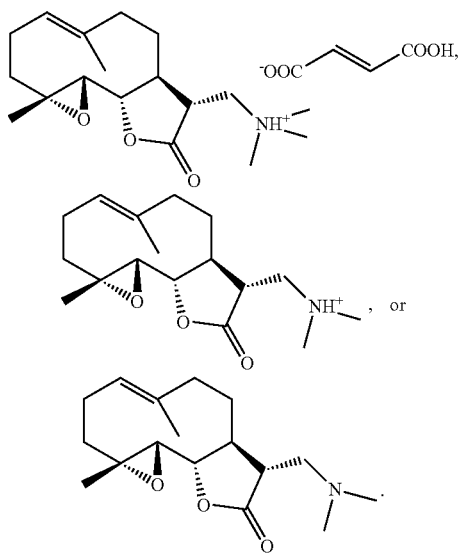
(IVa)

4. The compound of any one of embodiments 1 to 3, or a pharmaceutically acceptable salt thereof, wherein $L^0$ is a bond.

5. The compound of any one of embodiments 1 to 3, or a pharmaceutically acceptable salt thereof, wherein $L^0$ is an unsubstituted $C_1$-$C_6$ alkylene.

6. The compound of any one of embodiments 1 to 3, or a pharmaceutically acceptable salt thereof, wherein $L^0$ is an unsubstituted $C_1$-$C_4$ alkylene.

7. The compound of any one of embodiments 1 to 3, or a pharmaceutically acceptable salt thereof, wherein $L^0$ is an unsubstituted methylene.

8. The compound of any one of embodiments 1 to 7, or a pharmaceutically acceptable salt thereof, wherein $R^1$ is $L^1$-$R^3$; $L^1$ is independently a bond or an unsubstituted $C_1$-$C_{10}$ alkylene; and $R^3$ is independently hydrogen, halogen, —$CH_3$, —$CF_3$, —$CCl_3$, —CN, —S(O)$CH_3$, —OH, —$NH_2$, —COOH, —$CONH_2$, —$NO_2$, —C(O)$CH_3$, —$CH_2CH_3$, —$CH_2CH_2OH$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)OH, —NHOH, —$OCH_3$, —$OCF_3$, —$OCHF_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

9. The compound of any one of embodiments 1 to 8, or a pharmaceutically acceptable salt thereof, wherein $L^0$ is a bond.

10. The compound of any one of embodiments 1 to 8, or a pharmaceutically acceptable salt thereof, wherein $L^1$ is an unsubstituted $C_1$-$C_4$ alkylene.

11. The compound of any one of embodiments 1 to 8, or a pharmaceutically acceptable salt thereof, wherein $L^0$ is an unsubstituted methylene.

12. The compound of any one of embodiments 1 to 11, or a pharmaceutically acceptable salt thereof, wherein $R^3$ is independently hydrogen, halogen, —$CH_3$, —$CF_3$, —$CCl_3$, —CN, —$S(O)CH_3$, —OH, —$NH_2$, —COOH, —$CONH_2$, —$NO_2$, —$C(O)CH_3$, —$CH_2CH_3$, —$CH_2CH_2OH$, —SH, —$SO_2Cl$, —$SO_3H$, —$SO_4H$, —$SO_2NH_2$, —$NHNH_2$, —$ONH_2$, —$NHC$=$(O)NHNH_2$, —$NHC$=$(O)NH_2$, —$NHSO_2H$, —$NHC$=$(O)H$, —$NHC(O)OH$, —NHOH, —$OCH_3$, —$OCF_3$, —$OCHF_2$, 4-methoxybenzyl, 4-methoxyphenyl, or pyridyl.

13. The compound of any one of embodiments 1 to 12, or a pharmaceutically acceptable salt thereof, wherein $R^2$ is $L^2$-$R^4$; $L^2$ is independently a bond or an unsubstituted $C_1$-$C_{10}$ alkylene; and $R^4$ is independently hydrogen, halogen, —$CH_3$, —$CF_3$, —$CCl_3$, —CN, —$S(O)CH_3$, —OH, —$NH_2$, —COOH, —$CONH_2$, —$NO_2$, —$C(O)CH_3$, —$CH_2CH_3$, —$CH_2CH_2OH$, —SH, —$SO_2Cl$, —$SO_3H$, —$SO_4H$, —$SO_2NH_2$, —$NHNH_2$, —$ONH_2$, —$NHC$=$(O)NHNH_2$, —$NHC$=$(O)NH_2$, —$NHSO_2H$, —$NHC$=$(O)H$, —$NHC(O)OH$, —NHOH, —$OCH_3$, —$OCF_3$, —$OCHF_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

14. The compound of any one of embodiments 1 to 13, or a pharmaceutically acceptable salt thereof, wherein $L^2$ is a bond.

15. The compound of any one of embodiments 1 to 13, or a pharmaceutically acceptable salt thereof, wherein $L^2$ is an unsubstituted $C_1$-$C_4$ alkylene.

16. The compound of any one of embodiments 1 to 13, or a pharmaceutically acceptable salt thereof, wherein $L^2$ is an unsubstituted methylene.

17. The compound of any one of embodiments 1 to 16, or a pharmaceutically acceptable salt thereof, wherein $R^4$ is independently hydrogen, halogen, —$CH_3$, —$CF_3$, —$CCl_3$, —CN, —$S(O)CH_3$, —OH, —$NH_2$, —COOH, —$CONH_2$, —$NO_2$, —$C(O)CH_3$, —$CH_2CH_3$, —$CH_2CH_2OH$, —SH, —$SO_2Cl$, —$SO_3H$, —$SO_4H$, —$SO_2NH_2$, —$NHNH_2$, —$ONH_2$, —$NHC$=$(O)NHNH_2$, —$NHC$=$(O)NH_2$, —$NHSO_2H$, —$NHC$=$(O)H$, —$NHC(O)OH$, —NHOH, —$OCH_3$, —$OCF_3$, —$OCHF_2$, 4-methoxybenzyl, 4-methoxyphenyl, or pyridyl.

18. The compound of any one of embodiments 1 to 7, or a pharmaceutically acceptable salt thereof, wherein $R^1$ and $R^2$ are joined to form an unsubstituted heterocycloalkyl.

19. The compound of any one of embodiments 1 to 7, or a pharmaceutically acceptable salt thereof, wherein $R^1$ and $R^2$ are joined to form an unsubstituted piperidinyl.

20. The pharmaceutically acceptable salt of any one of embodiments 1 to 19, wherein the compound has a formula selected from the group consisting of formula I, II, IV, Ia, IIa, and IVa, and wherein the compound comprises a protonated nitrogen cation.

21. The compound, or a pharmaceutically acceptable salt thereof, of any one of embodiments 1 to 2, wherein the compound is selected from the group consisting of

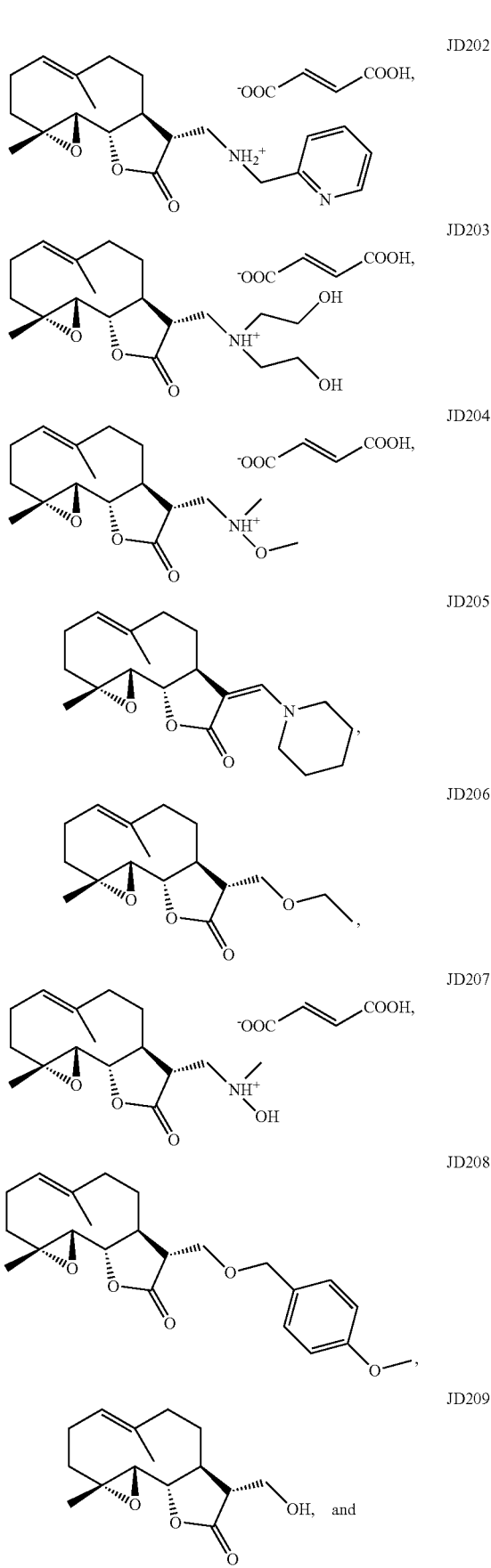

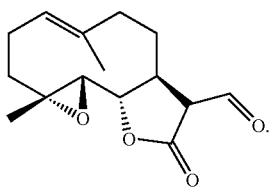
JD210

22. A pharmaceutical composition comprising a pharmaceutically acceptable excipient and a compound, or pharmaceutically acceptable salt thereof, of any one of embodiments 1 to 21.

23. The pharmaceutical composition of embodiment 22, comprising a second agent wherein said second agent is an anti-cancer agent.

24. A method of treating cancer in a patient in need of said treatment, said method comprising administering a therapeutically effective amount of a compound of any one of embodiments 1 to 21, or a pharmaceutically acceptable salt thereof, to said patient.

25. The method of embodiment 24, wherein said cancer is breast cancer.

26. The method of embodiment 25, wherein said breast cancer is resistant to an anti-cancer agent.

27. The method of embodiment 26, wherein said anti-cancer agent is trastuzumab.

28. The method of embodiment 25, wherein said breast cancer is resistant to a hormonal therapeutic agent.

29. The method of embodiment 28, wherein said hormonal therapeutic agent is tamoxifen.

30. The method of embodiment 24, wherein said cancer is lung cancer.

31. The method of embodiment 30, wherein said lung cancer is non-small cell lung cancer.

32. The method of any one of embodiments 30 to 31, wherein said lung cancer is resistant to an anti-cancer agent.

33. The method of embodiment 32, wherein said anti-cancer agent is a platinum-based compound.

34. The method of any one of embodiments 32 to 33, wherein said anti-cancer agent is cisplatin or carboplatin.

35. A method of treating a non-malignant hyperproliferative disease in a patient in need of said treatment, said method comprising administering a therapeutically effective amount of a compound of any one of embodiments 1 to 21, or a pharmaceutically acceptable salt thereof, to said patient.

36. The method of embodiment 35, wherein said non-malignant hyperproliferative disease is selected from the group consisting of a hamartomatous lesion, angiomyolipoma, lymphangioleiomyomatosis, tuberous sclerosis complex, a hamartia, or a hamartoma.

37. A method of inhibiting cancer cell growth or survival comprising contacting the cell with an effective amount of a compound of any one of embodiments 1 to 21, or a pharmaceutically acceptable salt thereof.

38. The method of embodiment 37, wherein said cancer cell is a cancer stem cell.

39. The method of embodiment 37, wherein said cancer cell is a cancer progenitor cell.

40. The method of any one of embodiments 37 to 38, wherein said cancer cell is a lung cancer cell or breast cancer cell.

41. The method of embodiment 37, wherein said compound, or a pharmaceutically acceptable salt thereof, increases apoptosis of said cancer cells.

42. A method of decreasing the level of activity of NF-κB in a cell comprising contacting the cell with an effective amount of a compound of any one of embodiments 1 to 21, or a pharmaceutically acceptable salt thereof.

43. A method of increasing the level of activity of TSC1 in a cell comprising contacting the cell with an effective amount of a compound of any one of embodiments 1 to 21, or a pharmaceutically acceptable salt thereof.

44. A method of increasing the level of activity of TSC2 in a cell comprising contacting the cell with an effective amount of a compound of any one of embodiments 1 to 21, or a pharmaceutically acceptable salt thereof.

45. A method of decreasing the level of activity of mTOR in a cell comprising contacting the cell with an effective amount of a compound of any one of embodiments 1 to 21, or a pharmaceutically acceptable salt thereof.

VII. Examples

The following examples are offered to illustrate, but not to limit the claimed invention.

A. Isolation of Cancer Stem/Progenitor Cells from Lung Cancer Cell Lines

Substantial evidence has accumulated to support the role of a small subset of self-renewing cells that sustain malignant growth. This subpopulation is termed cancer-initiating cells or cancer stem/progenitor cells (CSC) for their high capacity for self-renewal and superior levels of malignancy. Cancer stem cells are identified and isolated in several malignancies including lung cancer. CD133 (prominin-1), a 5-transmembrane glycoprotein, has been reported as an important biomarker to identify subsets of human lung CSC. Further, isolated lung cancer cells with high aldehyde dehydrogenase-1 (ALDH) activity display in vitro and in vivo features of cancer stem cells and express surface marker CD133. Based on these findings, we identified CD133+/ALDH+ tumor stem/progenitor cells from human lung cancer cells in vitro using an Aldefluor assay (to isolate ALDH+ cells) (5, 7, 8) in combination with labeled anti-CD133 antibodies (3, 10) followed by fluorescence-activated cell sorting analysis (11). In brief, ALDH activity and CD133 expression were analyzed by established double labeling methods using the Aldefluor Assay Kit (Stem Cell Technologies) and CD133/1 antibody (Miltenyi) according to the manufacturer's instructions. Cells were suspended in assay buffer and incubated with the ALDH substrate Aldefluor or with Aldefluor and the ALDH inhibitor diethylaminobenzaldehyde DEAB (negative control) for 30 min at 37 C. Cells were subsequently washed and labeled with Allophycocyanin (APC)-conjugated CD133/1 for 30 min on ice. Cells were washed with assay buffer twice and analyzed using FACSCalibur (BD Bioscience) and CellQuest software (BD Bioscience). Data were analyzed using FlowJo (Tree Star Inc.). Treatment with estrogen, a known risk factor for lung cancer progression (12), stimulated a modest increase in the numbers of CSC (FIG. 1). This latter effect of estrogens was blocked by use of antiestrogens (11).

B. Properties of Isolated Cancer Stem Cells

Figure 2:
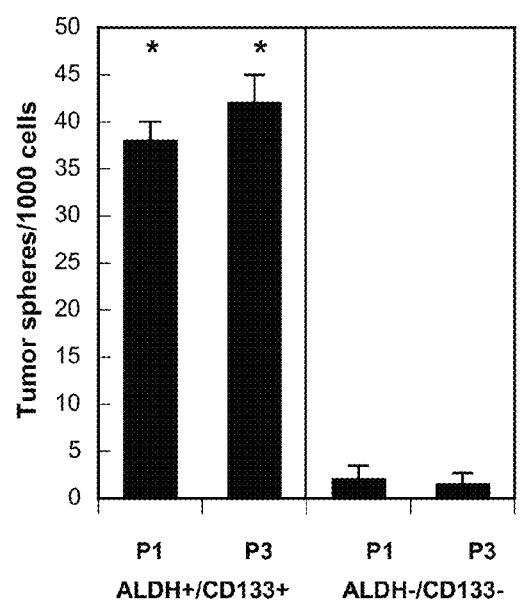
FIG. 2. ALDH+/CD133+ tumor cell subpopulations form tumor spheres and exhibit self-renewal properties. For tumor sphere experiments, single cell suspensions of NSCLC cells (A549) were plated on 1% agarose-coated plates at a density of $1\times10^5$ and grown for 7-10 days. Aldefluor-positive (ALDH⁺) and CD133-positive (CD133+) cells isolated after treatment with steroid hormones (31) formed significantly greater numbers and sizes of tumor spheres as compared to Aldefluor-negative (ALDH−) and CD133-negative (CD133−) controls (P<0.001). Subsequent cultures after dissociation of primary spheres were plated on ultralow attachment plates at a density of $5\times10^3$ to $1\times10^4$ (see P1, P3, $1^{st}$ and $3^{rd}$ passages, respectively). Tumor sphere cultures were grown in a serum-free basal medium as previously described [31]. Among ALDH+/CD133+ cells isolated after control treatment in the absence of steroid hormones (31), the number of tumor spheres formed was only 11±4 (n=3) per 1000 cells after 7-10 days; this result was significantly different than that found with ALDH+/CD133+ cells isolated after treatment with steroids (P<0.01; not shown). *, values significantly different from controls at P<0.001.

We cultivated subpopulations of lung tumor cells isolated following treatment with steroid hormones (11) and determined that these CD133+/ALDH+ subsets were able to grow as tumor spheres and maintain self-renewal capacity, properties indicative of CSC. In contrast, control CD133−/ALDH− subsets were not capable of significant tumor sphere formation (FIG. 2).

Further in vitro studies of CSC subsets indicate that these cells are more resistant to cisplatin and docetaxel chemotherapy treatment than bulk NSCLC cells. Moreover, the CSC subpopulations exhibit constituitive nuclear localization of NFκB as determined by immunofluorescence microscopy.

C. Parthenolide Analogues Inhibit Growth of Lung Cancer Stem Cells

Figure 3:
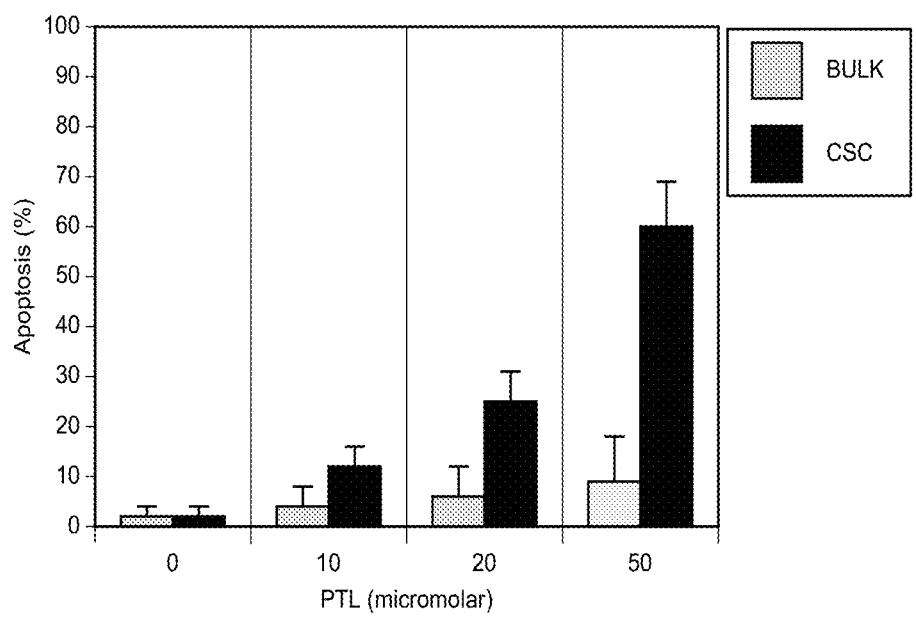
FIG. 3. Parthenolide congener (JD201; DMAPT) elicits dose-dependent increments in apoptosis of cancer stem cells (CSC) derived from NSCLC (H157). A comparison is performed using bulk NSCLC cells. Results based on annexin-V assays in 3 independent experiments.
Figure 4:
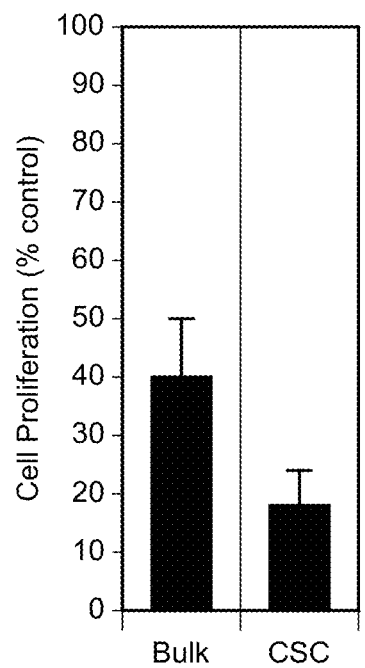
FIG. 4. Parthenolide analogue (JD201; DMAPT) inhibits proliferation of NSCLC cells using both bulk cell preparations (bulk) and CSC-subpopulations (CSC). Effects are significantly different from control at P<0.05. JD201 drug dose=20 micromolar.

Analogues of parthenolide were prepared and purified (FIG. 8) and assessed for antitumor efficacy, to develop the best agents for clinical use. Responses of CSC-like subsets, bulk tumor cells and normal lung epithelial cells to parthenolide (PTL) analogues alone and with chemotherapy are ongoing, with assessments by TUNEL and Annexin-V assay for apoptosis (13) (FIG. 3) and cell proliferation (FIG. 4).

To assess drug interactions in vitro and statistical significance, t-tests, ANOVA or other appropriate tests were used (5, 14, 15). An example of results with parthenolide analogue JD201 (DMAPT) is shown in FIG. 3 (apoptosis data) and FIG. 4 (cell proliferation).

These findings using JD201 (DMAPT) are promising for antitumor activity in NSCLC cells, particularly in CSC subsets.

Figure 5:
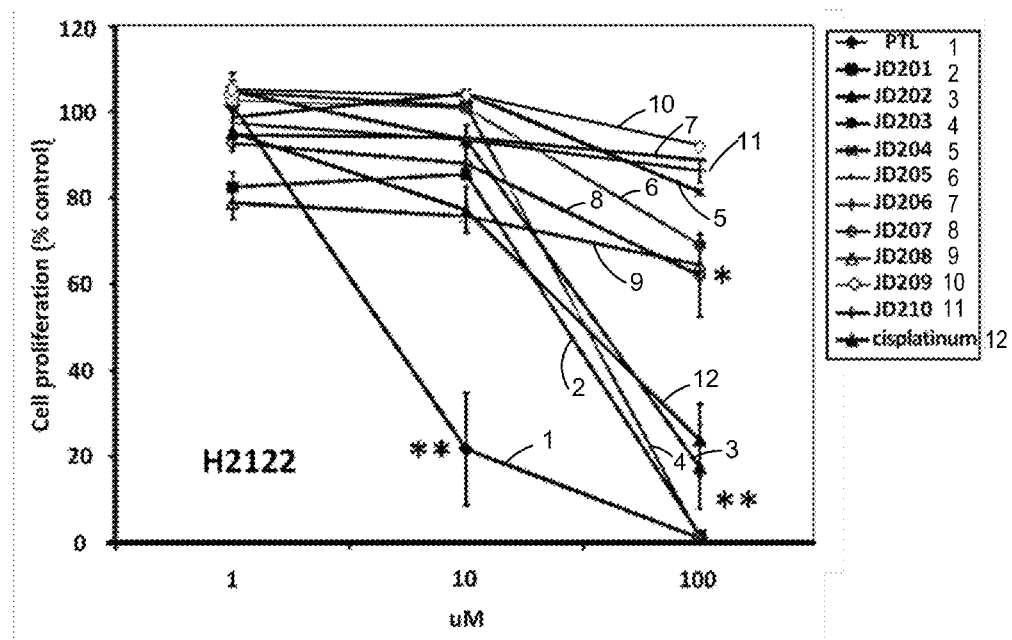
FIG. 5. Parthenolide analogues JD201-JD210 suppress human lung tumor cell proliferation in vitro. A549, H23, H2122 and H1975 NSCLC cells were treated with increasing concentrations of drugs (0.1-100 µM). After 72 h cell viability was assessed by MTS assay. Viable cells are expressed as percentage of vehicle control. P<0.01 (**), versus control group, P<0.05 (*), versus control group. Natural occurring parthenolide (PTL), parthenolide analogues JD201 (DMAPT)-JD210. Parthenolide analogues inhibit female (H1975, H2122) and male (H23, A549) NSCLC cell proliferation. Cells were treated with increasing concentrations of parental parthenolide (PTL), compounds JD201 (DMAPT/LC-1) and JD203 and cisplatin for comparison.
Figure 5:
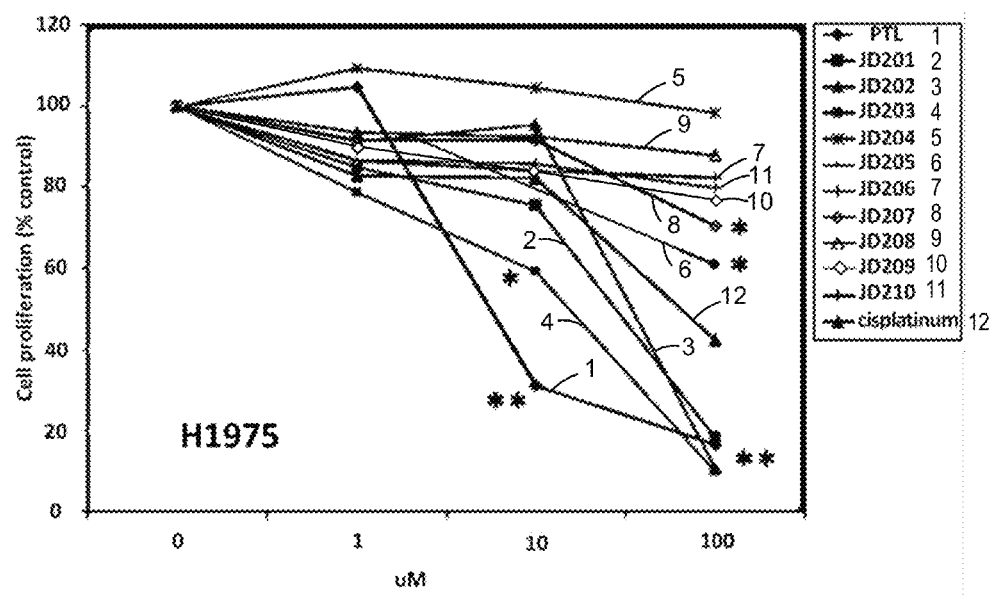
Figure 5:
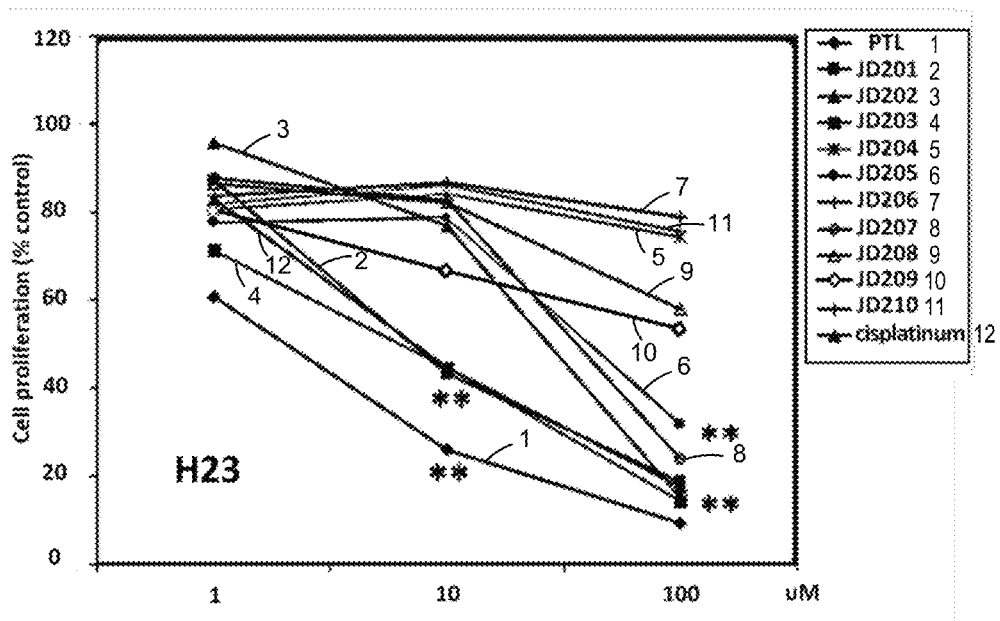
Figure 5:
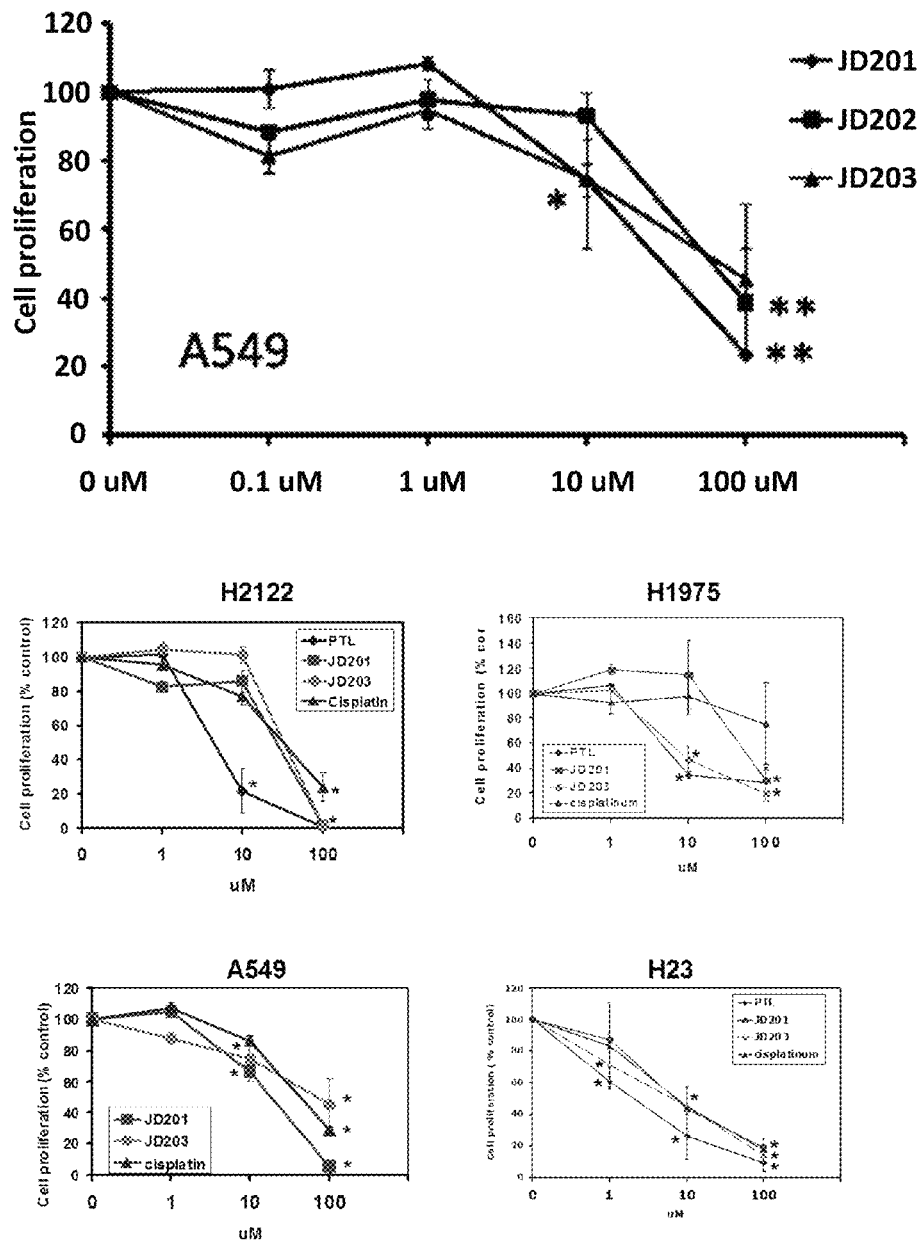

D. Effect of Parthenolide Analogues in Bulk Non-Small Cell Lung Cancer Cell Lines To determine the effect of parthenolide analogues in lung cancer cell proliferation we tested two male (A549, H23) and two female (H2122, H1975) lung cancer cell lines with increasing concentrations of parthenolide analogues (0.1, 1, 10 and 100 μM) for 72 hours. FIG. 5 shows growth inhibition by compounds 201-210 in a dose dependent manner (P>0.01). Significant growth inhibition was observed at 10 μM (201, 202 and 203) and 100 M (201, 202, 203, 205 and 207) concentrations of parthenolides. Data shown in FIG. 5 indicate that parthenolide analogues JD 201, 202 and 203 had greater inhibitory activity than compounds 205 and 207.

Figure 6:
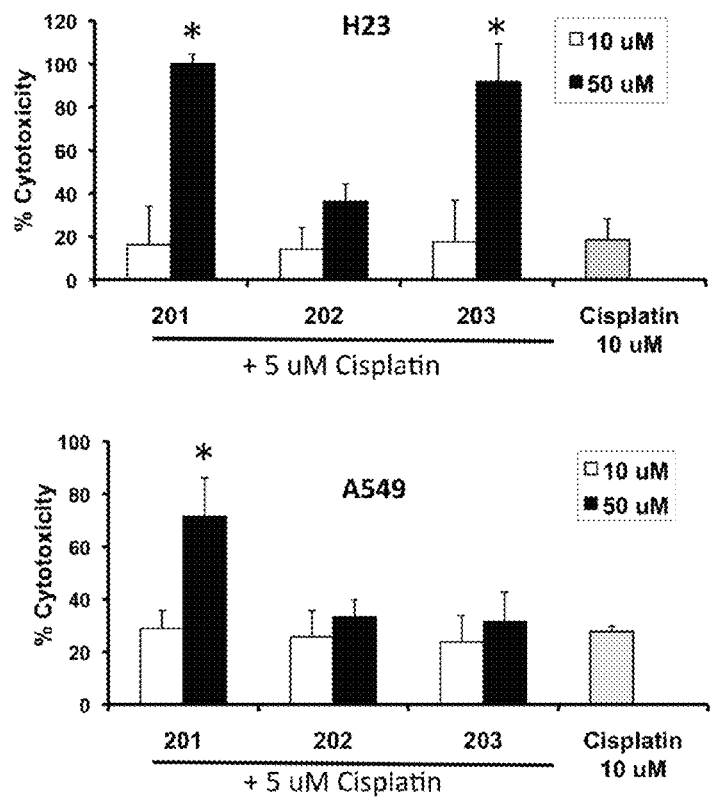
FIG. 6. Parthenolide analogues sensitize lung tumor cells to cisplatin-induced cytotoxicity. Non-small cell lung cancer cells H23 and A549 were exposed to 10 and 50 µM of each parthenolide analogue compound in the presence of 5 µM cisplatin. After 72 hrs, cytotoxicity was measured by use of an LDH release assay. Cisplatin cytotoxicity at 10 µM is shown as an independent reference control. P<0.01, versus control group. Results represent average values from at least 3 different experiments. Parthenolide analogues inhibit female (H1975, H2122) and male (H23, A549) NSCLC cell proliferation.

E. Parthenolide Analogues Sensitize Lung Tumor Cells to Cisplatin-Induced Cytotoxicity In addition, to determine if parthenolides can sensitize lung cancer cells to cytotoxicity induced by cisplatin, a drug commonly used in the clinic, we treated cells with 10 and 50 μM concentrations of parthenolide analogues in the presence of 5 μM cisplatin, a suboptimal dose that does not elicit significant cytotoxicity when administered alone. After 72 hours, LDH release was measured as a correlate of cell death and membrane disruption. Exposure to 10 μM cisplatin is shown as an independent control of cytotoxicity (reduced cell viability) induced by cisplatin. Compound JD201 significantly increased the cytotoxicity induced by cisplatin in both NSCLC cell lines assessed in these studies (see FIG. 6).

Figure 7:
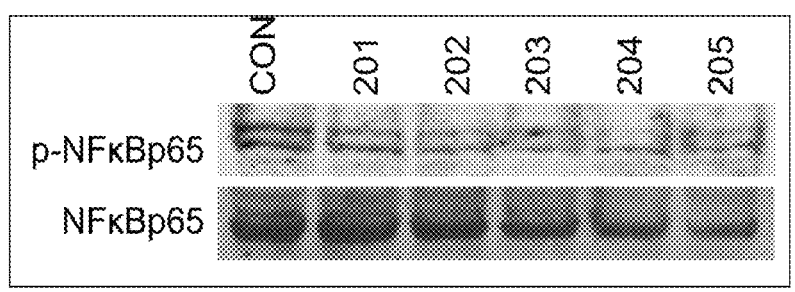
FIG. 7. Parthenolide analogues inhibit phosphory-lation of NF-κB/p65. H23 cells were treated with vehicle (CON) or 10 uM concentration of parthenolide analogues (201, 202, 203, 204, 205). After 60 min Western blot were performed using anti-phospho-NF-κB/p65 antibody (Cell Signaling Technology #3031). Membranes were stripped and re-probed with antibody against total NF-κB/p65 (CST #3037).

Upon confirming that parthenolide analogues can inhibit NSCLC cell proliferation, induce cell death and enhance the cytotoxicity of chemotherapy, we began to investigate potential cellular mechanisms that may underlie this process. For example, we used Western Blot methods to determine phosphorylation of the p65 subunit of NF-κB. H23 cells were incubated in the presence of vehicle control or 10 μM concentration of the parthenolide derivatives (JD 201, 202, 203, 204) for 60 min. After treatment, cells were collected and homogenized in lysis buffer. Extracts were electrophoresed on 4-20% gradient SDS-PAGE gels and transferred to nitrocellulose membranes. Blots were probed with anti-phospho-NF-κB/p65 and NF-κB/p65 for a loading control. Incubation of cells in the presence of parthenolides reduced phosphorylation of the p65 subunit of NF-κB (See FIG. 7).

To further confirm the tumorigenic potential of CSC subsets (CD133+/ALDH+ cells) as compared with non-CSC populations (CD133−/ALDH− cells), we implanted the tumor cell subpopulations subcutaneously in immunosuppressed mice [16]. Tumor growth occurred in all 3 of 3 mice inoculated subcutaneously with either 200 or 20,000 CSC (CD133+/ALDH+ cells). In contrast, no tumor growth was detected with inoculation of 200 non-CSC (CD 133−/ALDH− tumor cells), but 1 of 3 mice developed tumors with injection of 20,000 non-CSC (CD133−/ALDH− cells) (16). Thus, these findings suggest that CSC (CD133+/ALDH+ tumor cells) show a greater tumorigenic capability than non-CSC subsets (CD133−/ALDH− cell) in vivo. Studies of the effects of a parthenolide analogue alone and in combination with chemotherapy are in progress. Initial in vivo findings with A549 NSCLC xenografts implanted in immunodeficient mice indicate that parthenolide analogue JD201 elicits a reduction in tumor progression when administered as an oral gavage (100 mg/kg/day) for 21 days as compared to a vehicle control, with tumor volumes of 55±5 mm$^3$ in the JD201 group versus 252±31 mm$^3$ in controls. Additional studies of the interaction of this drug with chemotherapy in vivo are continuing.

We have identified subpopulations of chemotherapy-resistant human NSCLC cells with enrichment for CSC biomarkers and significant CSC activity. To target cancer stem cells and suppress tumor progression, we synthesized and tested analogues of parthenolide that show strong anticancer activity, with marked suppression of CSC subsets. Use of parthenolide analogues may lead to a new strategy to eradicate lung cancer.

F. General Methods for Breast Cancer Experiments

Studies detailed below were done primarily using a panel of MCF-7 and SKBR3 human breast cancer cells (ATCC) with different properties. Overall, this panel include:

1.

TABLE 1

| Cell Line | Cell Properties |
| --- | --- |
| MCF-7/CON | MCF-7 parent breast tumor cells without HER2 overexpression and ER+ (2) |
| MCF-7/HER2 | MCF-7 breast tumor cells with HER2 overexpression and ER+ (2) |
| MCF-7/TMR | MCF-7 breast tumor cells with acquired tamoxifen resistance and ER+ (38) |
| SKBR3/CON | SKBR3 parent breast tumor cells without HER2 overexpression and ER− |
| SKBR3/TZR | SKBR3 breast tumor cells with HER2 overexpression and acquired traztuzumab (Herceptin) resistance (39) |

MCF-7/CON cells are tamoxifen-sensitive, while MCF-7/HER2 and MCF-7/TMR cells are known to be tamoxifen-resistant (28, 61, 66, 67). Except for TMR (64, 68), cells were routinely cultured in RPMI 1640 media with 10% heat-inactivated FBS (28, 64, 66). For E2-free conditions, media were changed 48 h before studies to phenol-red free RPMI 1640 with 1% dextran-coated, charcoal-treated (DCC) FBS. TMR cells were derived by long-term continuous exposure of cells to $10^{-7}$ M 4-hydroxy-tamoxifen by established methods (64, 68) and were maintained with $10^{-7}$ M 4-hydroxytamoxifen in medium. Levels of ERα and HER2 expression in these several cell lines were determined by use of Western blot methods. SKBR3 cells resistant to trastuzumab were developed and maintained as detailed before (65)

Cell Transfection and NF-kappaB Activity. Activity of NFkB was assessed by using established transient transfection and luciferase reporter assays. Cell cultures were seeded one day before transfection with luciferase (luc) reporters to a density of $1-2 \times 10^3$ cells/well in 96-well plates and using established growth media (67, 69). Cells were transiently transfected with 0.5 μg of NFκB-luc reporter vector (Promega), along with FuGene 6 transfection reagent (Roche). Renilla luciferase vector pRL-tk-luc (Promega) was co-transfected as an internal control reporter vector to normalize for transfection efficiency. Culture media was changed 20 h following transfection and cells were then maintained in appropriate media for 24 h. As per manufacturer's recommendations, cells were subsequently washed with PBS, lysed for Dual-Glo luciferase assay (Promega), and reporter activity measured by luminometer. The ratio of firefly luminescence/Renilla luminescence was used for comparison of NFκB driven gene activities in control cells.

Assays for Tumor Cell Proliferation.

Breast tumor cells were be grown in RPMI 1640 media with 10% heat-inactivated FBS (except for TMR and TZR cells as noted above). For estrogen-free conditions, medium were changed 48 h before studies to phenol-red free RPMI 1640 with 1% dextran-coated, charcoal-treated (DCC) FBS, then treated with selected reagents. Cell counts and viability tests (Trypan blue) will be done every 24 hr for 2-33 days. After 48-72 hr, proliferation was assessed by cell counts.

Statistical Analyses.

For this in vitro work, triplicates of experiments were done. Student's t-test, ANOVA, or Kruskal-Wallis test if outcomes are non-normally distributed, were used as appropriate to compare intervention groups. Analyses were evaluated using bar and scatter graphs with means, SD, SE. Time trend curves for agents under different conditions were obtained as appropriate. Repeated measures ANOVA was used as needed to assess time, condition, time by condition interaction effects. $P<0.05$ was considered significant.

G. Endocrine Resistant Breast Cancer

Figure 12:
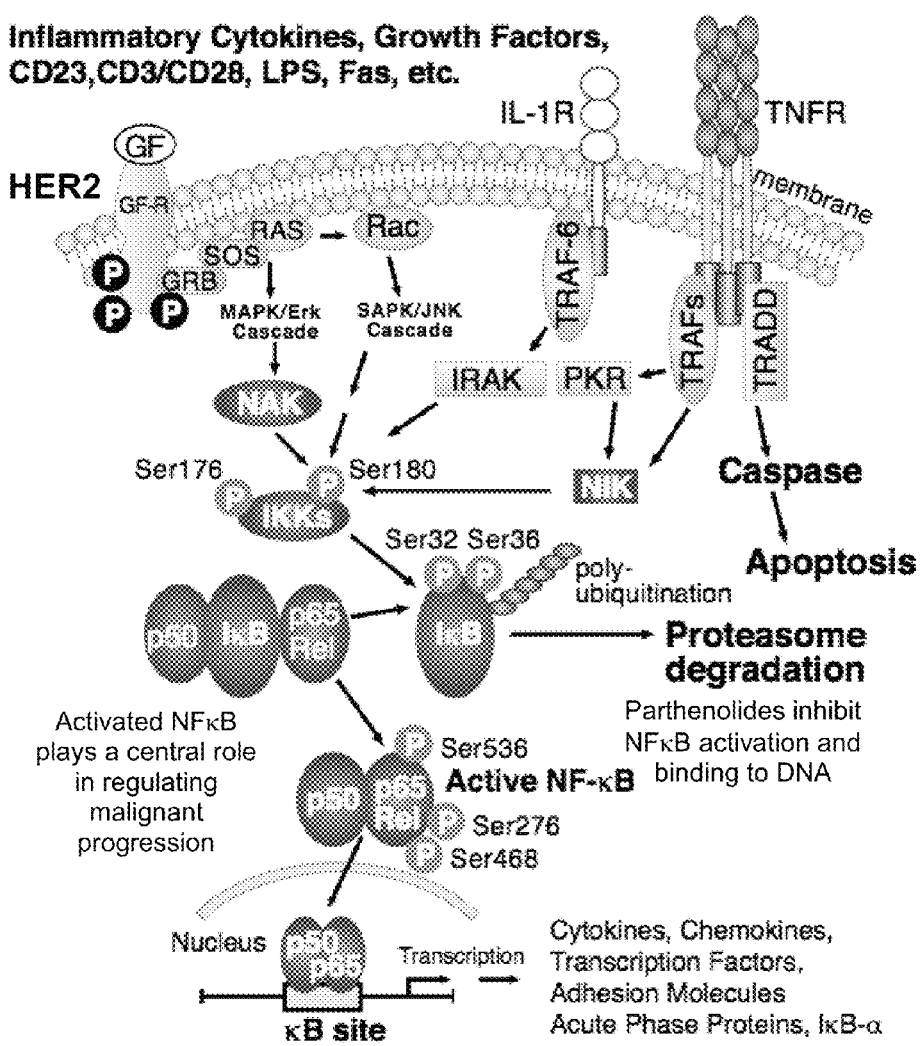
FIG. 12. Parthenolide analogues that inhibit NFκB activation may play a critical role in reversing therapeutic resistance. Top figure modified from Kalaitzidis D et al. (36).
Figure 12:
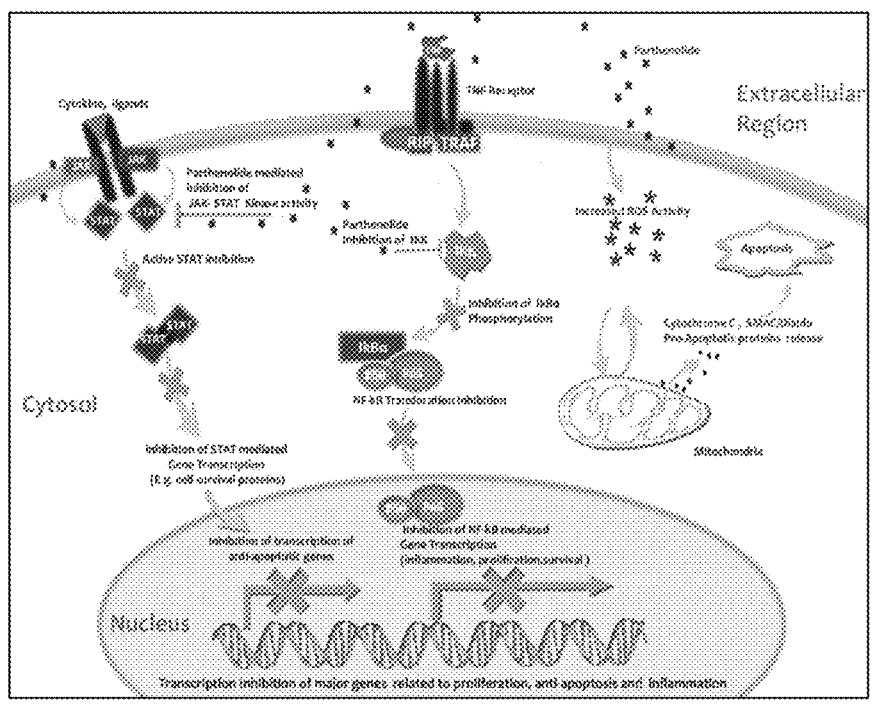

NFkB activity is enhanced in endocrine-resistant breast tumors. To investigate NFκB activation in endocrine-resistant breast cancer cells, we used tumor cell lines with known resistance to tamoxifen. For these studies, we used MCF-7 human breast cancer cells that express abundant ERα and are sensitive to tamoxifen (28, 29, 67). The activity of NFkB in MCF-7 control cells was compared to that of tamoxifen-resistant MCF-7 (MCF-7/TMR) and MCF-7 HER2-overexpressing (MCF-7/HER2) cells (see FIG. 12).

Parthenolide analogues reduce proliferation of breast cancer cells with tamoxifen resistance. To investigate the effects of parthenolide (PTL) analogues on breast tumor cell proliferation in vitro, we cultivated MCF-7 breast cancer cells with HER-2 overexpression (28) in the presence and absence of PTL analogues 201 and 203 (see FIG. 13). As noted above, these MCF-7/HER2 cells are tamoxifen-resistant. Both analogues elicited a dose-dependent reduction in proliferation of MCF-7/HER2 cells as compared to controls.

Figure 14:
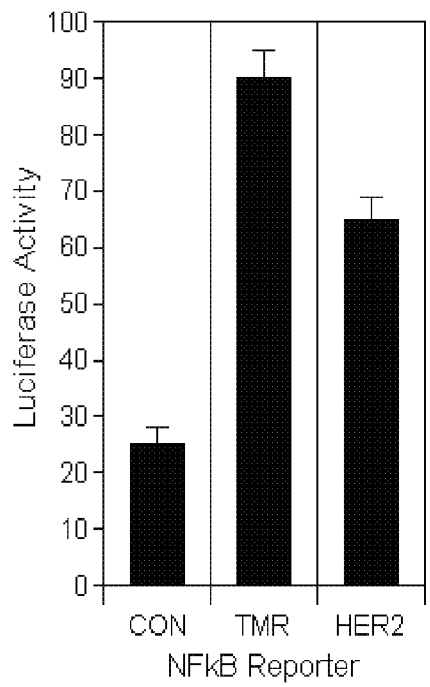
FIG. 14. NFkB activity in MCF-7 breast cancer cells is enhanced with tamoxifen resistance and with HER2 overexpression; activity of NFkB in MCF-7 control cells (CON) was compared to that of tamoxifen-resistant MCF-7 (TMR) and MCF-7 HER2-overexpressing (HER2) cells that were cultivated under established in vitro conditions (28, 29, 67); activity of NFkB was assessed by using established transient transfection and luciferase reporter assays; cell cultures were seeded one day before transfection with luciferase (luc) reporters to a density of 1-2×103 cells/well in 96-well plates and using established growth media (67, 70); cells were transiently transfected with 0.5 g of NFκB-luc reporter vector (Promega), along with FuGene 6 transfection reagent (Roche); Renilla luciferase vector pRL-tk-luc (Promega) was co-transfected as an internal control reporter vector to normalize for transfection efficiency; culture media was changed 20 h following transfection and cells were then maintained in appropriate media for 24 h; as per manufacturer's recommendations, cells were subsequently washed with PBS, lysed for Dual-Glo luciferase assay (Promega), and reporter activity measured by luminometer; the ratio of firefly luminescence/Renilla luminescence was used for comparison of NFκB driven gene activities in control cells; all transient transfection and reporter gene results are presented as means (±SEM) from at least 3 independent experiments; MCF7/HER2 and MCF/TMR results showed significant differences (p<0.001) from comparably cultured MCF7 controls.
Figure 15:
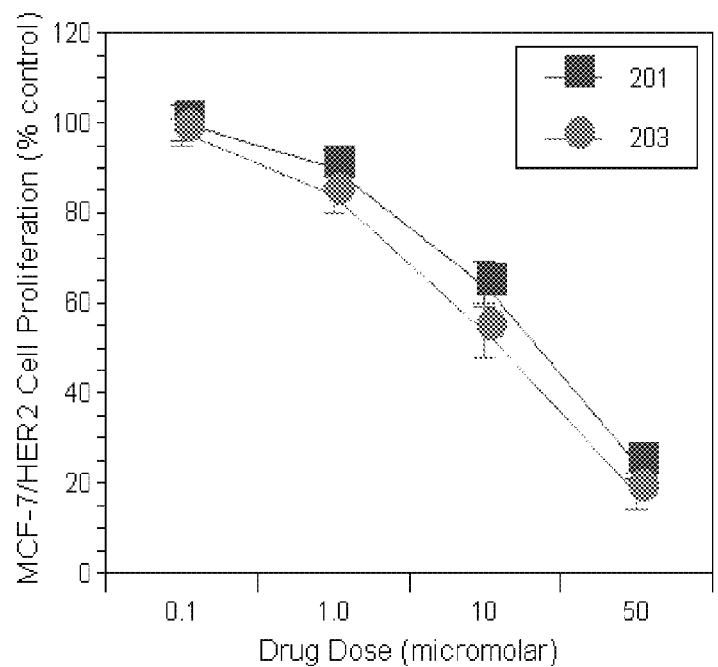
FIG. 15. Parthenolide analogues 201 and 203 reduce proliferation of MCF-7/HER2 cells with tamoxifen resistance; analogues 201 and 203 were both effective in inducing a dose-dependent (0.1-50 micromolar) reduction in proliferation of MCF-7/HER2 as compared to controls (P<0.001); cell proliferation was determined by cell counts after 72 hours incubation in vitro in standard media (28, 29, 67).
Figure 16:
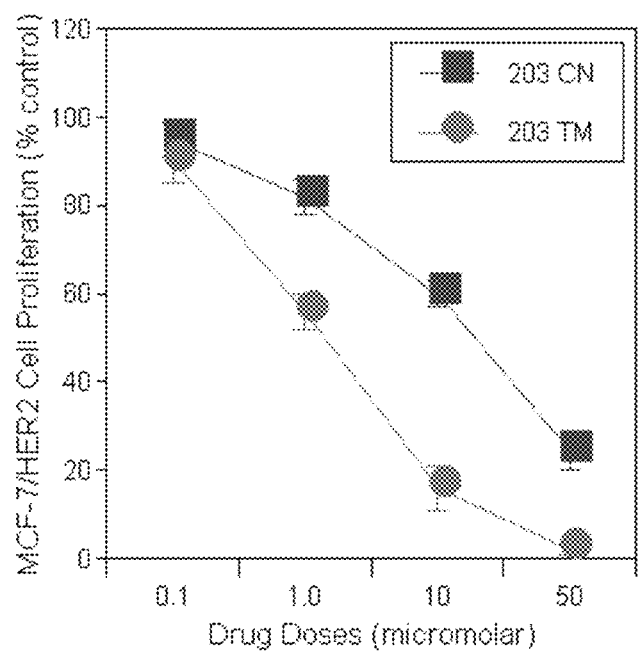
FIG. 16. (A) Parthenolide analogue 203 enhances antitumor efficacy of tamoxifen in tamoxifen-resistant MCF-7/HER2 breast cancer cells; MCF-7/HER2 with tamoxifen resistance were plated in established media (28, 67) and then treated with doses of parthenolide analogue 203 ranging from 0.1 to 50 micromolar for 72 hours; cell proliferation was then determined using cell counts; administration of tamoxifen ($1\times10^{-7}$ M) with parthenolide analogue 203 elicited a greater reduction in cell proliferation than treatment with the analogue alone ($P<0.01$); (B) Parthenolide analogue 203 promotes antitumor effects of tamoxifen in tamoxifen-resistant MCF-7/TAMR breast cancer cells; methods utilized in developing tamoxifen-resistant (TAM-R) cells have been described before (64, 68); wild-type (wt) and TAM-R MCF-7 cells were plated into 6-well plates ($3\times10^4$ cells/well) in RPMI medium containing 5% FBS and grown for 2 days; thereafter, use of estrogen-deprived conditions were used wherein cells were stepped down into phenol red-free media containing 1% dextran-coated charcoal-stripped (DCC) serum (29, 67); cells were then treated with tamoxifen ($1\times10^{-7}$ M) with control vehicle (TM+203 vehicle), analogue 203 alone at varying doses (203 alone) or analogue 203 plus tamoxifen (203+TM) for 48 hours; cell numbers were then quantitated as described previously (29, 67); experiments were repeated three times to ensure reproducibility.
Figure 16:
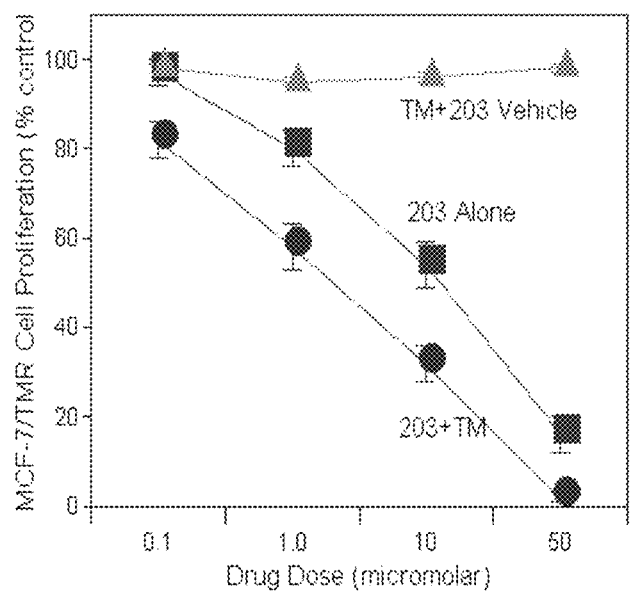

Parthenolide analogue enhances antitumor efficacy of tamoxifen in tamoxifen-resistant MCF-7/HER2 breast cancer cells. To further assess the activity of parthenolide analogue 203 when administered in combination with tamoxifen, we used MCF-7/HER2 cells with established tamoxifen-resistance (see FIG. 14). The results of this study indicate that parthenolide analogue 203 may help to sensitize these endocrine-resistant cells to tamoxifen.

Parthenolide analogue promotes antitumor effects of tamoxifen in tamoxifen-resistant MCF 7/TAMR breast cancer cells. To further assess the activity of parthenolide analogues in reversing tamoxifen resistance in human breast cancer cells, we used tamoxifen-resistant (TAM-R) cells developed as described previously (64, 68). (see FIG. 14).

Results of these studies show that the MCF-7/TMR cells are resistant to tamoxifen treatment in the absence of parthenolide analogues. However, combination of tamoxifen with parthenolide analogue 203 elicits enhanced blockade of tumor cell proliferation over a wide dose range of the analogue as compared to appropriate controls ($P<0.01$).

H. HER2+ Breast Cancers with Resistance to Trastuzumab

Activation of NFkB in HER2-overexpressing breast tumor cells resistant to Herceptin (trastuzumab) and effects of parthenolide analogues. The human breast cancer cell line SKBR3 (ATCC) was obtained from the American Type Culture Collection (ATCC). Unless otherwise stated, monolayer cultures of SKBR3 were maintained in Dulbeccos' Modified Eagle's Media (DMEM):F12 medium with 10% FBS. The cell lines overexpressed the HER2 gene product. Trastuzumab-resistant clones SKBR3/TZR were generated from SKBR3 cells as detailed previously (65). In brief, to select trastuzumab-resistant clones, SKBR3 cells were plated in 24-well plates at low density and maintained in growth medium containing 10, 50, and 100 mg/mL of trastuzumab. SKBR3/TZR cells were maintained in growth medium containing 100 mg/mL of trastuzumab. SKBR3/TZR cells were repeatedly confirmed as insensitive to trastuzumab. Data from routine proliferation assays showed that growth of SKBR3 parental (control) cells was significantly inhibited by fresh treatment with 10 and 100 mg/mL of trastuzumab, whereas the growth of SKBR3/TZR cells which were maintained in media containing 100 mg/mL trastuzumab were not inhibited in 2-5 days. The number of cells overexpressing HER2 receptors was reduced in SKBR3 cells on treatment with trastuzumab (10 mg/mL) for 72 hrs. However, SKBR3/TZR cells maintained in growth media containing 100 mg/mL trastuzumab for extended periods of time did not exhibit any significant difference in overall HER2 receptor overexpression compared with untreated parental cells.

Figure 8:
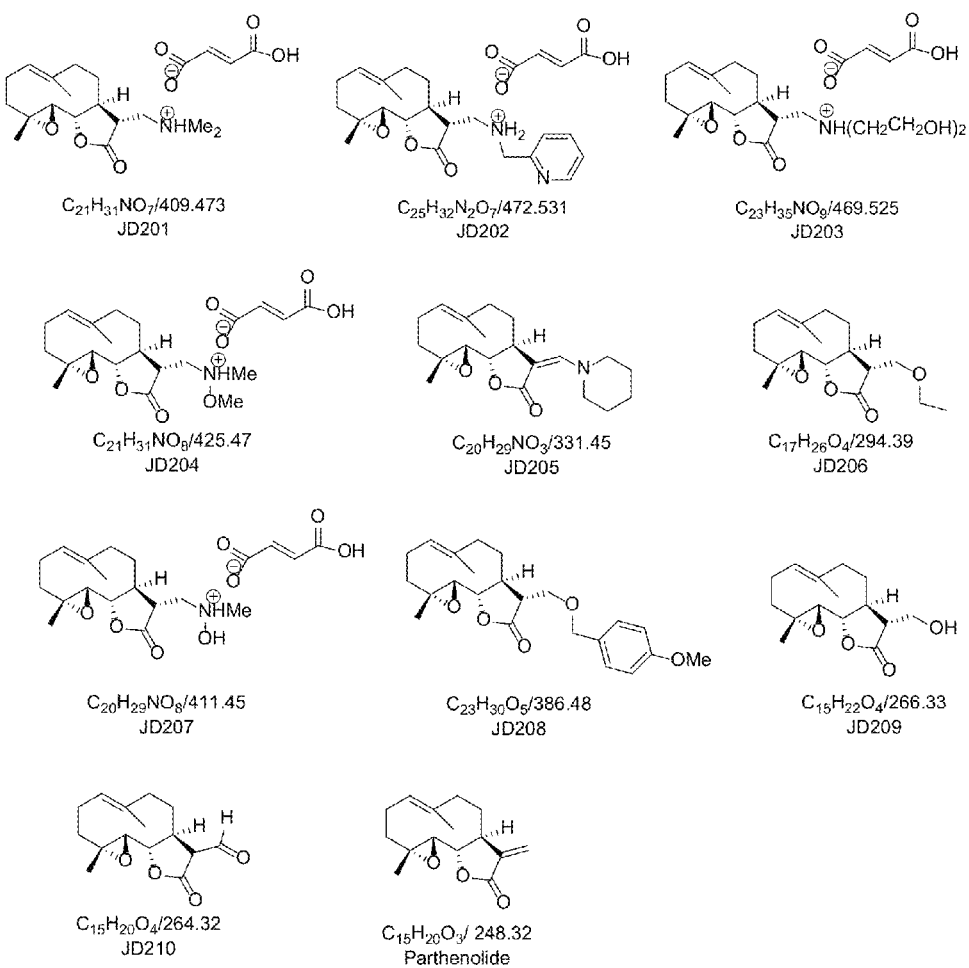
FIG. 8. Parthenolide Analogues. Chemical structure of sesquiterpene lactone parthenolide (Parthenolide) and related analogues, DMAPT (JD201) and JD202-210.
Figure 9:
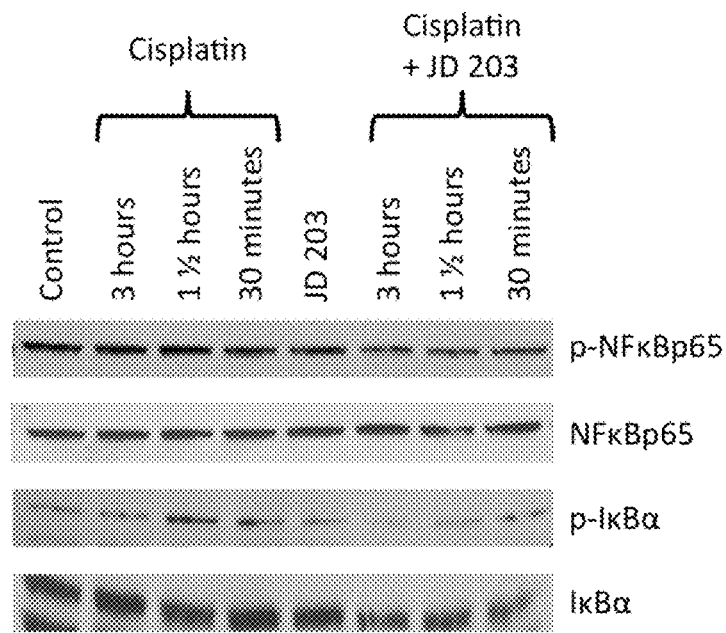
FIG. 9. Parthenolide analogues inhibit cisplatin-mediated phosphorylation of NF-κB/p65; A549 cells were treated with 5 M of cisplatin and/or 20 M of parthenolide analog JD 203 for the various time courses displayed. Western blots were then performed using anti-phospho-NF-κB/p65 antibody (Cell Signaling Technology #3036) and anti-phospho-IκBα antibody (CST #2859). Membranes were then stripped and reprobed with antibody against total NF-κB/p65 (CST #3987) and antibody against total IκBα (CST #4814).
Figure 10:
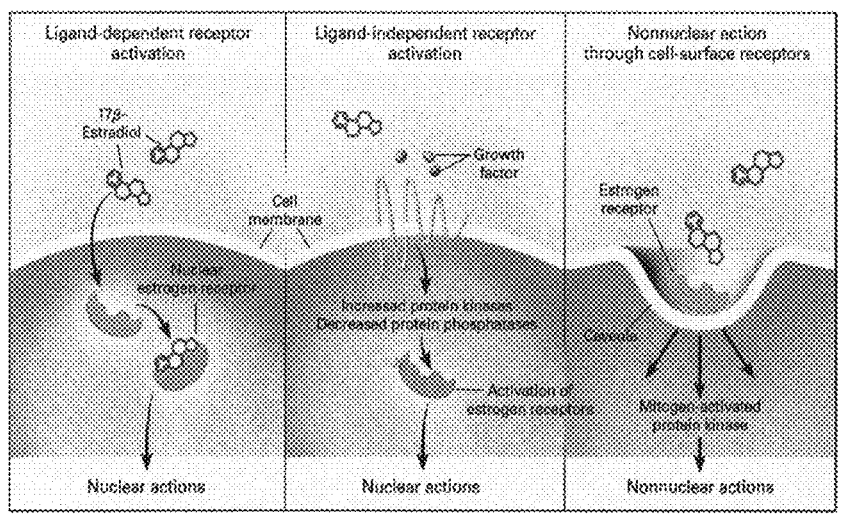
FIG. 10. Mechanisms of estrogen (E2) action; In current models of E2 action, E2 binds ER in the nucleus to promote receptor dimerization and phosphorylation that allows binding with coactivator (SRC) and estrogen-responsive elements (ERE), leading to gene transcription (left panel). Alternate pathways also impact E2 action. HER-2 receptor signaling, which may be altered by heregulin (HRG) or other growth factors, can interact with ER or downstream elements such as coactivators (middle panel). E2 may also bind ER localized in caveolae or lipid rafts to promote interaction with HER receptors, G-proteins, nucleotide cyclases, MAP kinase, PI3/Akt kinase or nuclear ER (right panel). Reprinted from New Engl J Med, 2002 (40).
Figure 11:
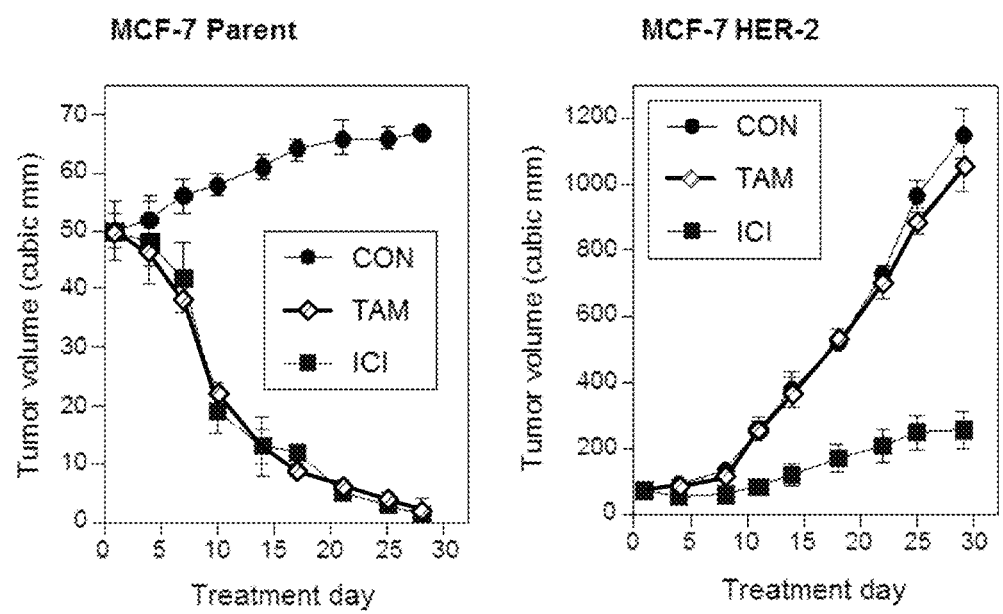
FIG. 11. Overexpression of HER2 gene in MCF7 cells elicits resistance to endocrine therapy in vivo; (a) Antiestrogen sensitivity of MCF7 parent cells without HER2 overexpression (control) in vivo (LEFT PANEL). MCF7 cells were inoculated SQ in ovari-ectomized, nude mice primed with estrogen. After 10 d, mice were randomized to treatment with tamoxifen (TAM; 5 mg sustained-release pellet SQ), ICI-182,780 (ICI; 5 mg in oil SQ Q wk) or control (CON) for 28d. Tumor volumes were recorded. No significant difference in accumulation of [3H]-tamoxifen by MCF-7 parent vs. HER2 cells was found (n=3; not shown). (b) Antiestrogen sensitivity of HER-2-overexpressing MCF-7 cells (HER-2) in vivo (RIGHT PANEL). MCF-7/HER2 cells were inoculated SQ in ovariectomized, athymic mice primed with estrogen. After 10 d, animals were randomized to therapy with tamoxifen (TAM), ICI-182,780 (ICI) or control (CON). Refer to methods as before (28, 29).
Figure 17:
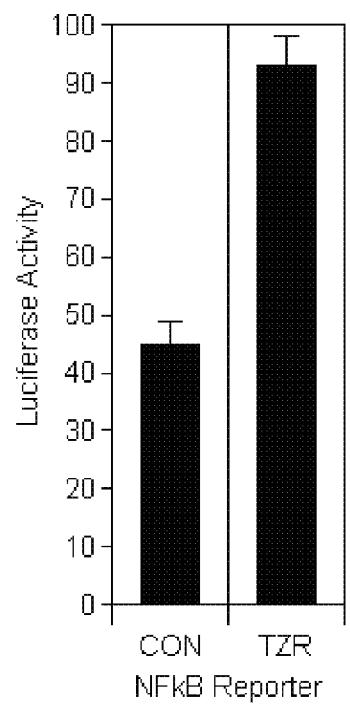
FIG. 17. NFκB activity in SKBR3 breast cancer cells sensitive (CON) and resistant (TZR) to trastuzumab treatment; methods used were as described in FIG. 14 above.
Figure 18:
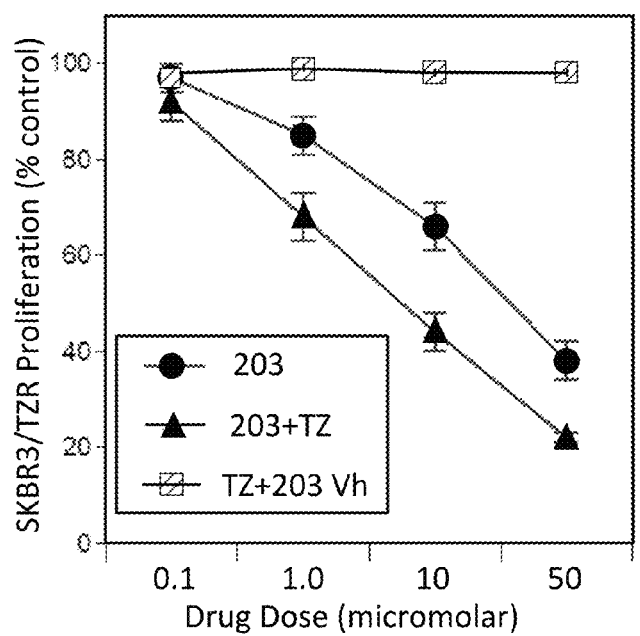
FIG. 18. Parthenolide analogue 203 reduces proliferation of SKBRS/TZR cells alone and in combination with trastuzumab in vitro; SKBR3 cells with resistance to trastuzumab were grown with 50 mg/ml trastuzumab alone (TX+203 Vh), parthenolide analogue 203 alone (203) at doses from 0.1 to 50 micromolar, or analogue 203 in combination with trastuzumab (203+TZ) for 72 hours prior to cell counts.

Results of experiments to assess NFkB activity in SKBR3 cells that sensitive (SKBR3/CON) and resistant to trastuzumab (SKBR3/TZR) treatment in vitro are shown in FIG. 8. These experiments indicate that one consequence of trastuzumab resistance in HER2+ breast cancer cells is the enhancement of NFkB activity. The data in FIG. 17 show that SKBR3/TZR cells have significantly increased NFkB activity as compared to SKBR3/CON cells ($P<0.001$). Such findings correlate with independent observations on the essential role of NFκB in HER2-induced oncogenesis by providing signals that maintain mammary tumor-initiating cells. The notion that HER2 can regulate NFκB and that NFκB can in turn regulate downstream pathways that, in turn, regulate HER2 suggests that these two important stem cell regulatory genes may interact in controlling cancer progression (70).

To determine the antitumor efficacy of parthenolide analogues known to block NFkB activation, we assessed their effects on proliferation of SKBR3/TZR cells in vitro (FIG.

17). These results show that parthenolide analogues elicit significant growth inhibition in HER2-overexpressing cells that are trastuzumab-resistant either when administered alone or in combination with trastuzumab (P<0.001). Further investigation of this unique strategy to block the progression of trastuzumab (Herceptin)-resistant breast cancers has important implications for the management of patients afflicted with this disease in the clinic.

I. Parthenolides in Nonmalignant Proliferative Disease

Figure 19:
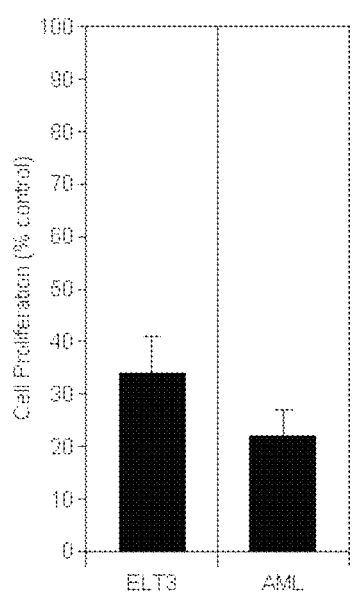
FIG. 19. Parthenolide analogue inhibits proliferation of ELT3 and angiomyolipoma (AML) cells that are in vitro models for TSC-related proliferative diseases. Cells were counted and plated and then treated with parthenolide analogue JD203 or control for 72 hours using IIA medium with 1% FBS. At the end of the experiments, cell proliferation was quantitated based on cell counts. Experimental results (n=3) shown as % control (mean±SE).

We have tested inhibitory activity of parthenolide analogues using cell models for TSC-related proliferative disease. The ELT3 cells are a TSC2-null smooth muscle-derived cell line from a rat uterine leiomyoma and often used as a model for lymphangioleiomyomatosis (LAM) and other TSC-related proliferative diseases (75, 76). Angiomyolipoma cells (AML) that have inactivating mutations in both alleles of the TSC2 gene were also used as an alternate cell model (77, 78). Cells were routinely cultured in IIA complete medium (50% DMEM, 50% F-12, 1.2 g/ml NaHCO$_3$, 1.6 mM FeSO$_4$, 50 nM sodium selenite, 25 mg/ml insulin, 200 nM hydrocortisone, 10 mg/ml transferrin, 1 nM triiodothyronine, 10 mU/ml vasopressin, 10 nM cholesterol, 10 ng/ml epidermal growth factor) containing 15% FBS. For study of proliferation, cells were incubated for 3 days in IIA medium containing 1% FBS. Effects of parthenolide analogue JD203 on proliferation of ELT3 and AML cells in vitro are shown in FIG. 19. Results of these experiments indicate that parthenolides may also have utility in the treatment of TSC-related proliferative diseases that are not classified as malignancies.

J. General Experimental Detail for Chemical Synthesis of Parthenolide Analogues

Dichloromethane and methanol were distilled from calcium hydride under an argon atmosphere. Diethyl ether was distilled from benzoquinone ketyl radical under an argon atmosphere. All other solvents or reagents were purified according to literature procedures. High resolution mass spectrometry data was obtained on a Waters LCT Premier XE Time of Flight LC-MS. $^1$H and $^{13}$C NMR spectra were obtained on AV-300, ARX-400, ARX-500 or Avance-500 spectrometers. The chemical shifts are reported in parts per million (ppm, δ). The coupling constants are reported in Hertz (Hz) and the resonance patterns are reported with the following notations: br (broad), s (singlet), d (doublet), t (triplet), q (quartet) and m (multiplet). Thin-layer chromatography (TLC) was carried out using precoated silica gel sheets (Merck 60 F$_{254}$). Visual detection was performed with ultraviolet light (short wave and long wave), p-anisaldehyde stain, and potassium permanganate stain. Flash chromatography was performed using SilicaFlash™ P60 (60 A, 40-63 mm) silica gel from SiliCycle Inc. with compressed air.

General Procedure a:

For Compounds Dg-2-11, Dg-2-12, Dg-2-13, Dg-2-36b, Dg-2-75. Parthenolide (20 mg, 0.08 mmol) and an excess of the amine (0.24 mmol) were dissolved in methanol (3.0 mL) and the mixture was stirred under argon at 21° C. overnight. The reaction mixture was extracted with ethyl acetate (3×15 mL), washed with water and brine, and dried over MgSO$_4$. After removal of the solvent by rotary evaporation, the crude product was purified by flash column chromatography to obtain the desired dialkylamino pathenolide adducts.

General Procedure B:

For Compounds JD201, JD202, JD203, JD204, JD207. The dialkylamino parthenolide adduct from above (0.01 mmol) was added to the stirred solution of fumaric acid (0.005 M, 2.0 mL) in diethyl ether at 0° C. After the mixture stirred for 10 min at 0° C., the reaction temperature was raised to 21° C. and the mixture was stirred for 2 h. The solvent was removed by rotary evaporation to afford the desired compounds.

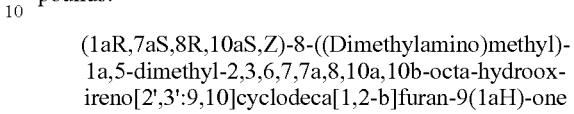

(1aR,7aS,8R,10aS,Z)-8-((Dimethylamino)methyl)-1a,5-dimethyl-2,3,6,7,7a,8,10a,10b-octa-hydrooxireno[2',3':9,10]cyclodeca[1,2-b]furan-9(1aH)-one The title compound, Dg-2-11, was obtained by following general procedure A using dimethylamine in 98% yield after flash column chromatography (eluent: dichloromethane/MeOH=20/1). $^1$H NMR (300 MHz, CDCl$_3$): δ 5.19 (1H, d, J=9.6 Hz), 3.82 (1H, t, J=9.0 Hz), 2.27 (6H, s), 1.68 (3H, s), 1.28 (3H, s). $^{13}$C NMR (75 MHz, CDCl$_3$): δ 176.4, 134.6, 125.0, 82.1, 66.4, 61.4, 57.5, 47.9, 46.4, 46.0, 41.0, 36.6, 29.9, 24.1, 17.2, 16.9. HR-MS (ESI) Calcd for [C$_{17}$H$_{27}$NO$_3$+H]$^+$ 294.2069. found 294.2073.

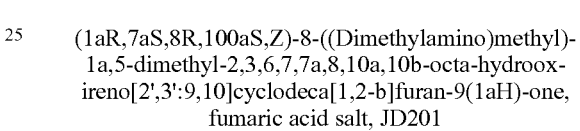

(1aR,7aS,8R,100aS,Z)-8-((Dimethylamino)methyl)-1a,5-dimethyl-2,3,6,7,7a,8,10a,10b-octa-hydrooxireno[2',3':9,10]cyclodeca[1,2-b]furan-9(1aH)-one, fumaric acid salt, JD201

The title compound, JD201, was obtained by following general procedure B. $^1$H NMR (400 MHz, DMSO-d$_6$): δ 6.61 (2H, s), 5.22 (1H, d, J=12.0 Hz), 3.98 (1H, t, J=12.0 Hz), 2.24 (6H, s), 1.65 (3H, s), 1.21 (3H, s). $^{13}$C NMR (75 MHz, CDCl$_3$): δ 177.1, 166.6, 134.8, 134.5, 125.0, 81.9, 65.8, 61.6, 57.7, 47.7, 46.0, 45.5, 40.9, 36.5, 29.1, 24.1, 17.3, 17.0. HR-MS (ESI) Calcd for [C$_{17}$H$_{27}$NO$_3$+H]$^+$294.2069. found 294.2058.

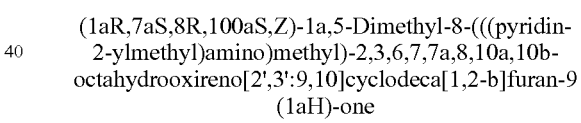

(1aR,7aS,8R,100aS,Z)-1a,5-Dimethyl-8-(((pyridin-2-ylmethyl)amino)methyl)-2,3,6,7,7a,8,10a,10b-octahydrooxireno[2',3':9,10]cyclodeca[1,2-b]furan-9(1aH)-one The title compound, Dg-2-13, was obtained by following general procedure A using 2-(aminomethyl)pyridine in 97% yield after flash column chromatography (eluent: dichloromethane/MeOH=20/1). $^1$H NMR (300 MHz, CDCl$_3$): δ 8.52 (1H, d, J=4.8 Hz), 7.64 (1H, dt, J=1.8, 7.8 Hz), 7.33 (1H, d, J=7.8 Hz), 7.16 (1H, d, J=5.4 Hz), 5.14 (1H, d, J=11.4 Hz), 4.09 (1H, dd, J=6.0, 15.0 Hz), 3.94 (1H, dd, J=15.0, 21.0 Hz), 3.83 (1H, t, J=9.0 Hz), 1.66 (3H, s), 1.26 (3H, s). $^{13}$C NMR (75 MHz, CDCl$_3$): δ 176.6, 159.3, 149.1, 136.5, 134.4, 125.0, 122.1, 122.0, 82.5, 66.2, 61.4, 55.1, 47.9, 46.6, 46.5, 40.9, 36.5, 29.8, 24.0, 17.1, 16.8. HR-MS (ESI) Calcd for [C$_{21}$H$_{28}$N$_2$O$_3$+H]$^+$357.2178. found 357.2191.

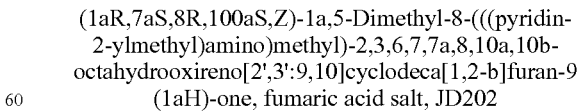

(1aR,7aS,8R,100aS,Z)-1a,5-Dimethyl-8-(((pyridin-2-ylmethyl)amino)methyl)-2,3,6,7,7a,8,10a,10b-octahydrooxireno[2',3':9,10]cyclodeca[1,2-b]furan-9(1aH)-one, fumaric acid salt, JD202

The title compound, JD202, was obtained by following general procedure B. $^1$H NMR (400 MHz, DMSO-d$_6$): δ 8.49 (1H, d, J=4.0 Hz), 7.74 (1H, t, J=7.5 Hz), 7.41 (1H, d, J=7.9 Hz), 7.24 (1H, dd, J=4.8, 7.4 Hz), 6.57 (2H, s), 5.17 (1H, d, J=12.5 Hz), 3.97 (1H, t, J=9.4 Hz), 1.60 (3H, s), 1.16 (3H, s). $^{13}$C NMR (75 MHz, CDCl$_3$): δ 176.6, 166.1, 158.9, 148.8, 136.6, 134.4, 134.1, 124.5, 122.2, 122.0, 81.7, 65.4, 61.2, 54.2, 47.1, 45.7, 45.6, 40.5, 36.1, 28.9, 23.7, 16.8, 16.6. HR-MS (ESI) Calcd for $[C_{21}H_{28}N_2O_3+H]^+$ 357.2178, found 357.2191.

(1aR,7aS,8R,10aS,Z)-8-((Bis(2-hydroxyethyl)amino)methyl)-1a,5-dimethyl-2,3,6,7,7a,8,10a,10b-octahydrooxireno[2',3':9,10]cyclodeca[1,2-b]furan-9(1aH)-one, Dg-2-12

The title compound, Dg-2-12, was obtained by following general procedure A using diethanolamine in 98% yield after flash column chromatography (dichloromethane/MeOH=20/1). $^1$H NMR (300 MHz, CDCl$_3$): δ 5.17 (1H, d, J=11.7 Hz), 3.87 (1H, t, J=9.0 Hz), 1.67 (3H, s), 1.27 (3H, s). $^{13}$C NMR (75 MHz, CDCl$_3$): δ 177.8, 134.3, 125.1, 82.4, 66.2, 61.6, 59.2, 59.2, 56.5, 56.5, 53.0, 47.3, 46.3, 40.9, 36.5, 29.7, 24.0, 17.1, 16.8. HR-MS (ESI) Calcd for $[C_{19}H_{31}NO_5+H]^+$ 354.2281. found 354.2294.

(1aR,7aS,8R,100aS,Z)-8-((Bis(2-hydroxyethyl)amino)methyl)-1a,5-dimethyl-2,3,6,7,7a,8,10a,10b-octahydrooxireno[2',3':9,10]cyclodeca[1,2-b]furan-9(1aH)-one, fumaric acid salt, JD203

The title compound, JD203, was obtained by following general procedure B. $^1$H NMR (500 MHz, DMSO-d$_6$): δ 6.61 (2H, s), 5.18 (1H, d, J=12.4 Hz), 3.94 (1H, t, J=9.5 Hz), 1.63 (3H, s), 1.18 (3H, s). $^{13}$C NMR (125 MHz, DMSO-d$_6$): δ 177.4, 166.3, 134.9, 134.3, 124.5, 82.0, 65.9, 61.5, 59.4, 59.4, 57.2, 57.2, 54.0, 46.7, 46.4, 40.0, 36.5, 29.2, 24.0, 17.2, 17.0. HR-MS (ESI) Calcd for $[C_{19}H_{31}NO_5+H]^+$ 354.2281. found 354.2284.

(1aR,7aS,8R,100aS,Z)-8-((Methoxy(methyl)amino)methyl)-1a,5-dimethyl-2,3,6,7,7a,8,10a,10b-octahydrooxireno[2',3':9,10]cyclodeca[1,2-b]furan-9(1aH)-one, Dg-2-36b The title compound, Dg-2-36b, was obtained by following general procedure A using N,O-dimethyl-hydroxylamine hydrochloride and potassium carbonate (33.2 mg, 0.24 mmol) in ethanol as the solvent in 79% yield after flash column chromatography (eluent: hexane/ethyl acetate=4/1). The ethoxy adduct, JD206, was also obtained in 8% yield in this reaction. $^1$H NMR (300 MHz, CDCl$_3$): δ 5.19 (1H, d, J=11.1 Hz), 3.83 (1H, t, J=9.0 Hz), 3.50 (3H, s), 2.63 (3H, s) 1.71 (3H, s), 1.30 (3H, s). $^{13}$C NMR (75 MHz, CDCl$_3$): δ 176.0, 134.7, 125.0, 82.0, 66.6, 61.4, 59.0, 58.4, 47.5, 46.2, 45.0, 41.1, 36.7, 29.8, 24.1, 17.2, 17.0. HR-MS (ESI) Calcd for $[C_{17}H_{27}NO_4+H]^+$ 310.2018. found 310.2026.

(1aR,7aS,8R,100aS,Z)-8-((Methoxy(methyl)amino)methyl)-1a,5-dimethyl-2,3,6,7,7a,8,10a,10b-octahydrooxireno[2',3':9,10]cyclodeca[1,2-b]furan-9(1aH)-one, fumaric acid salt, JD204

The title compound, JD204, was obtained by following general procedure B. $^1$H NMR (300 MHz, MeOD): δ 6.75 (2H, s), 5.25 (1H, d, J=9.6 Hz), 4.00 (1H, t, J=9.0 Hz), 3.49 (3H, s), 2.60 (3H, s) 1.72 (3H, s), 1.30 (3H, s). $^{13}$C NMR (75 MHz, MeOD): δ 179.1, 168.0, 168.0, 136.2, 135.2, 125.8, 83.6, 68.1, 63.2, 59.4, 59.3, 48.2, 47.2, 45.2, 42.0, 37.7, 30.5, 25.0, 17.2, 17.1. HR-MS (ESI) Calcd for $[C_{17}H_{27}NO_4+H]^+$ 310.2018. found 310.2031.

(1aR,7aS,8R,10aS,Z)-8-((Hydroxy(methyl)amino)methyl)-1a,5-dimethyl-2,3,6,7,7a,8,10a,10b-octahydrooxireno[2',3':9,10]cyclodeca[1,2-b]furan-9(1aH)-one, Dg-2-75

The title compound, Dg-2-75, was obtained by following general procedure A using N-methylhydroxyl-amine hydrochloride and potassium carbonate (33.2 mg, 0.24 mmol) in 93% yield after flash chromatography (eluent: dichloromethane/MeOH=40/1). $^1$H NMR (300 MHz, CDCl$_3$): δ 5.17 (1H, d, J=11.7 Hz), 3.84 (1H, t, J=9.0 Hz), 2.70 (3H, s) 1.68 (3H, s), 1.28 (3H, s). $^{13}$C NMR (75 MHz, CDCl$_3$): δ 176.8, 134.6, 124.9, 82.3, 66.3, 61.6, 59.7, 49.5, 47.5, 45.9, 41.0, 36.6, 29.6, 24.0, 17.1, 16.9. HR-MS (ESI) Calcd for $[C_{16}H_{25}NO_4+H]^+$ 296.1862. found 296.1859.

(1aR,7aS,8R,100aS,Z)-8-((Hydroxy(methyl)amino)methyl)-1a,5-dimethyl-2,3,6,7,7a,8,10a,10b-octahydrooxireno[2',3':9,10]cyclodeca[1,2-b]furan-9(1aH)-one, fumaric acid salt, JD207

The title compound, JD207, The title compound was obtained by following general procedure B. $^1$H NMR (300 MHz, MeOD): δ 6.75 (2H, s), 5.25 (1H, d, J=9.9 Hz), 3.98 (1H, t, J=9.0 Hz), 2.68 (3H, s) 1.72 (3H, s), 1.30 (3H, s). $^{13}$C NMR (75 MHz, MeOD): δ 179.3, 168.2, 168.2, 136.3, 135.2, 135.2, 125.7, 83.9, 68.0, 63.2, 60.1, 49.7, 47.9, 47.1, 41.9, 37.7, 30.5, 25.0, 17.5, 17.1. HR-MS (ESI) Calcd for $[C_{16}H_{25}NO_4+H]^+$ 296.1862. found 296.1864.

(1aR,7aS,8R,10aS,Z)-8-(Ethoxymethyl)-1a,5-dimethyl-2,3,6,7,7a,8,10a,10b-octahydrooxi-reno[2',3':9,10]cyclodeca[1,2-b]furan-9(1aH)-one, JD206

The title compound, JD206, was obtained in the reaction that produced compound Dg-2-36b above in 8% yield. $^1$H NMR (300 MHz, CDCl$_3$): δ 5.22 (1H, d, J=9.9 Hz), 3.83 (1H, t, J=9.0 Hz), 3.75 (1H, dq, J=3.0, 9.0 Hz), 3.54 (1H, dq, J=3.0, 9.0 Hz), 2.77 (1H, d, J=9.0 Hz), 2.41 (1H, d, J=9.0 Hz), 1.70 (3H, s), 1.25 (3H, s), 1.19 (3H, t, J=9.0 Hz). $^{13}$C NMR (75 MHz, CDCl$_3$): δ 175.1, 134.6, 125.1, 82.2, 67.0, 66.4, 66.3, 61.4, 48.6, 45.8, 41.1, 36.6, 30.0, 24.1, 17.2, 16.9, 15.0. HR-MS (ESI) Calcd for $[C_{17}H_{26}O_4+H]^+$ 295.1909. found 295.1918.

(1aR,7aS,8R,10aS,Z)-8-(((4-methoxybenzyl)oxy)methyl)-1a,5-dimethyl-2,3,6,7,7a,8,10a,10b-octahydrooxireno[2',3':9,10]cyclodeca[1,2-b]furan-9(1aH)-one, JD208

Parthenolide (49 mg, 0.2 mmol) and 1,8-diazabicyclo[5.4.0]undec-7-ene (DBU, 0.3 μL, 2.0 mmol) were dissolved in 4-methoxybenzyl alcohol (1.0 mL), and the mixture was stirred under argon at 21° C. overnight. The reaction mixture was extracted with ethyl acetate (3×15 mL), washed with water and brine, and dried over MgSO$_4$. After removal of the solvent by rotary evaporation, the crude product was purified by flash column chromatography (eluent: hexane/ethyl acetate=4/1) to obtain the desired product, JD208. $^1$H NMR (300 MHz, CDCl$_3$): δ 7.24 (2H, d, J=8.4 Hz), 6.88 (2H, d, J=8.4 Hz), 5.17 (1H, d, J=11.4 Hz), 4.49 (2H, q, J=11.7 Hz), 3.80 (3H, s), 3.80 (1H, t, J=9.0 Hz), 3.68 (1H, dd, J=3.0, 9.0 Hz), 2.72 (1H, d, J=9.0 Hz), 1.67 (3H, s), 1.28 (3H, s). $^{13}$C NMR (75 MHz, CDCl$_3$): δ 175.0, 159.2, 134.5, 130.0, 129.2, 129.2, 125.0, 113.7, 113.7, 82.2, 73.0, 66.3, 65.4, 61.4, 55.2, 48.5, 45.6, 40.9, 36.6, 29.8, 24.0, 17.1, 16.8. HR-MS (ESI) Calcd for $[C_{23}H_{30}O_5+H]^+$ 387.2172. found 387.2186.

(1aR,7aS,8R,10aS,Z)-8-(Hydroxymethyl)-1a,5-dimethyl-2,3,6,7,7a,8,10a,10b-octahydrooxi-reno[2',3':9,10]cyclodeca[1,2-b]furan-9(1aH)-one, JD209

A mixture of the PMB ether JD208 (44 mg, 0.114 mmol) and 2,3-dichloro-5,6-dicyano-1,4-benzoquinone (DDQ, 39 mg, 0.171 mmol) in dichloromethane (1.0 mL) and water (0.05 mL) was stirred for 2 h at 0° C. The mixture was diluted with dichloromethane (20 mL) and dried over $MgSO_4$. The dichloromethane was removed by rotary evaporation and the residue was purified by flash column chromatography (eluent: hexane/ethyl acetate=1/1) to obtain the desired product, JD209. $^1$H NMR (300 MHz, $CDCl_3$): δ 5.19 (1H, d, J=11.7 Hz), 4.08 (2H, m), 3.87 (1H, t, J=8.7 Hz), 3.76 (1H, dd, J=4.5, 11.7 Hz), 2.75 (1H, d, J=9.0 Hz), 1.67 (3H, s), 1.28 (3H, s). $^{13}$C NMR (75 MHz, $CDCl_3$): δ 176.4, 134.4, 125.2, 82.7, 66.2, 61.6, 58.7, 50.0, 44.8, 40.9, 36.5, 29.8, 24.0, 17.1, 16.8. HR-MS (ESI) Calcd for $[C_{15}H_{22}O_4+H]^+$ 267.1596. found 267.1608.

(1aR,4Z,7aS,8Z,10aS)-1a,5-Dimethyl-8-(piperidin-1-ylmethylene)-2,3,6,7,7a,8,10a,10b-octahydrooxireno[2',3':9,10]cyclodeca[1,2-b]furan-9(1aH)-one, JD205

A mixture of the hydroxymethyl analogue, JD209 (20 mg, 0.075 mmol), and Dess-Martin periodinane (39 mg, 0.09 mmol) in anhydrous dichloromethane (1.0 mL) was stirred for 2 h at 0° C. The mixture was diluted with dichloromethane (20 mL) and dried over $MgSO_4$. The dichloromethane was removed by rotary evaporation. The crude residue was dissolved in anhydrous methanol (0.5 mL), piperidine (75 µL, 0.76 mmol) was added, and the mixture was stirred at room temperature overnight. The reaction mixture was extracted with ethyl acetate (3×15 mL), washed with water and brine, and dried over $MgSO_4$. After removal of the solvent by rotary evaporation, the crude product was purified by flash column chromatography (eluent: dichloromethane/MeOH=30/1) to obtain the desired product, JD205. $^1$H NMR (300 MHz, $CDCl_3$): δ 7.17 (1H, d, J=1.8 Hz), 5.21 (1H, d, J=12.3 Hz), 3.78 (1H, t, J=6.6 Hz), 1.65 (3H, s), 1.24 (3H, s). $^{13}$C NMR (75 MHz, $CDCl_3$): δ 174.3, 147.1, 134.3, 125.1, 91.9, 82.1, 66.8, 61.3, 51.6, 51.6, 46.9, 40.8, 36.1, 33.3, 26.0, 26.0, 24.4, 23.8, 17.5, 17.5. HR-MS (ESI) Calcd for $[C_{20}H_{29}NO_3+H]^+$ 332.2226. found 332.2232.

K. References

1. Mi J, X Zhang, Z Rabbani, Y Liu, S Reddy, Z Su, F Salahuddin, K Viles, P Giangrande, M Dewhirst, B Sullenger, C Kontos, B Clary (2008). RNA aptamer-targeted inhibition of NF-κB suppresses non-small cell lung cancer resistance to doxorubicin. Molecular Therapy 16: 66-73. 2. Al-Hajj M, Wicha M, Benito-Hernandez A, et al. (2003). Prospective identification of tumorigenic breast cancer cells. Proc Natl Acad Sci USA 100: 3983-3988. 3. Hermann P, S Huber, T Herrler, et al. (2007). Distinct populations of cancer stem cells determine tumor growth and metastatic activity in human pancreatic cancer. Cell Stem Cell 1: 313-323. 4. Fillmore C, Kuperwasser C (2008). Human breast cancer cell lines contain stem-like cells that self-renew, give rise to phenotypically diverse progeny and survive chemotherapy. Breast Cancer Res 10: R25. 5. Ginestier C, Hur M, Charafe-Jauffret E, et al. (2007). ALDH1 is a marker of normal and malignant human mammary stem cells and a predictor of poor clinical outcome. Cell Stem Cell 1: 555-567. 6. Levina V, Marrangoni A M, DeMarco R, Gorelik E, Lokshin A E (2008). Drug-selected human lung cancer stem cells: cytokine network, tumorigenic and metastatic properties. PLoS One 3:e3077. 7. Jiang F, Q Qiu, A Khanna, N Todd, J Deepak, L Xing, H Wang, Z Liu, Y Su, S Stass, R Katz (2009). Aldehyde dehydrogenase-1 is a tumor stem cell-associated marker in lung cancer. Mol Cancer Res 7: 330-338. 8. Moreb J, H Baker, L-J Chang, M Amaya, M C Lopez, B Ostmark, W Chou (2008). ALDH isozymes down-regulation affects cell growth, cell motility and gene expression in lung cancer cells. Mol Cancer 7: 87-105. 9. Zhang D, Qui L, Jin X, Guo Z, Gio C (2009). Nuclear factor-kappaB inhibition by parthenolide potentiates the efficacy of taxol in non-small cell lung cancer in vitro and in vivo. Mol Cancer Res 7: 1139-1149. 10. Eramo A, F Lotti, G Sette, E Pilozzi, M Biffoni, A Di Virgilio, C Conticello, L Ruco, C Peschle, R De Maria (2008). Identification and expansion of the tumorigenic lung cancer stem cell population. Cell Death and Differentiation 15: 504-514. 11. Marquez-Garban D, Erin L. Maresh, Mohammad Alavi, Hsiao-Wang Chen, Vei Mah, Lora Bagryanova, Steve Horvath, David Chia, Edward Garon, Lee Goodglick, Richard J. Pietras (2011). Progesterone and estrogen receptor expression and activity in human non-small cell lung cancer. Steroids (in press). 12. Chlebowski R T. Menopausal hormone therapy, hormone receptor status, and lung cancer in women. Semin Oncol. 2009, 36 (6):566-71. 13. Wu W, A Onn, T Isobe, S Itasaka et al. (2007). Targeted therapy of orthotopic human lung cancer by combined vascular endothelial growth factor and epidermal growth factor receptor signaling blockade. Molecular Cancer Therapeutics 6: 471-483. 14. Pegram M, Konecny G, O'Callaghan C et al. (2004). Rational combinations of trastuzumab with chemotherapeutic drugs used in the treatment of breast cancer. J Natl Cancer Inst 96: 739-749. 15. Chou T C, Talalay P (1984). Quantitative analysis of dose-effect relationships: the combined effects of multiple drugs or enzyme inhibitors. Adv Enzyme Regul 22:27-55 16. C-M Tsai C-M, K-T Chang, L-H Wu, J-Y Chen, A Gazdar, T Mitsudomi, M-H Chen, R-P Perng (1996). Correlations between intrinsic chemoresistance and HER-2/neu gene expression, p53 gene mutations, and cell proliferation characteristics in non-small cell lung cancer cell lines. Cancer Research 56: 206-209. 17. American Cancer Society: Cancer Facts and Figures 2012. Atlanta, Ga.: American Cancer Society, 2012 18. Shanmugan R, Kusumanchi P, Appaiah H, Cheng L, Crooks P, Neelakantan S, Peat T, Klaunig J, Matthews W, Nakshatri H, Sweeney C J. A water soluble parthenolide analog suppresses in vivo tumor growth of two tobacco-associated cancers, lung and bladder cancer, by targeting NF-κB and generating reactive oxygen species. Int J. Cancer. 201, 128 (10):2481-94. 19. Zhang D, Qiu L, Jin X, Guo Z, Guo C. Nuclear factor kappaB inhibition by parthenolide potentiates the efficacy of Taxol in non-small cell lung cancer in vitro and in vivo. Mol Cancer Res. 2009, 7 (7): 1139-49. 20. Neelakantan S, Nasim S, Guzman M L, Jordan C T, Crooks P A. Aminoparthenolides as novel antileukemic agents: discovery of the NF-kappaB inhibitor, DMAPT (LC-1). Bioorg Med Chem Lett 2009; 19:4346-9. 21. Guzman M L, Rossi R M, Neelakantan S, Li X, Corbett C A, Hassane D C, Becker M W, Bennett J M, Sullivan E, Lachowicz J L, Vaughan A, Sweeney C J, et al. (2007). An orally bioavailable parthenolide analog selectively eradicates acute myelogenous leukemia stem and progenitor cells. Blood; 110: 4427-35. 22. Hehner S P, Heinrich M, Bork P M, Vogt M, Ratter F, Lehmann V, Schulze-Osthoff K, Droge W, Schmitz M L. (1998). Sesquiterpene lactones specifically inhibit activation of NF-kappa B by preventing the degradation of I kappa B-alpha and I kappa B-beta. Biol Chem; 273:1288-97. 23. Wen J, You K R, Lee S Y, Song C H, Kim D G. (2002). Oxidative stress-mediated apoptosis. The anticancer effect of the sesquiterpene lactone parthenolide. J Biol Chem; 277: 38954-64. 24. Curry E A, III, Murry D J, Yoder C, Fife K, Armstrong V, Nakshatri H, O'Connell M, Sweeney C J. (2004). Phase I dose escalation trial of feverfew with standardized doses of parthenolide in patients with cancer. Invest New Drugs; 22:299-305. 25. Shanmugam R, Jayaprakasan V, Gokmen-Polar Y, Kelich S, Miller K D, Yip-Schneider M, Cheng L, Bhat-Nakshatri P, Sledge G W, Jr, Nakshatri H, Zheng Q-H, Miller M A, et al. (2006). Restoring chemotherapy and hormone therapy sensitivity by parthenolide in a xenograft hormone refractory prostate cancer model. Prostate; 66:1498-511. 26. Nasim S, Crooks P A. Antileukemic activity of aminoparthenolide analogs. Bioorg Med Chem. Lett. 2008; 18(14):3870-3.

27. Harris J., M. Lippman, U. Veronesi & W. Willett (1992). Breast cancer. N. Engl. J. Med., 327: 473-451. 28. Pietras, R. J., Arboleda, J., Wongvipat, N., Ramos, L., Parker, M. G., Sliwkowski, M. X., and Slamon, D. J. (1995). HER-2 tyrosine kinase pathway targets estrogen receptor and promotes hormone-independent growth in human breast cancer cells. Oncogene, 10: 2435-2446. 29. Marquez, D, Pietras, R J (2001). Membrane-associated binding sites for estrogen contribute to growth regulation in human breast cancer cells. Oncogene, 20: 5420-5430. 30. Bange J, Zwick E, Ullrich A (2001). Molecular targets for breast cancer therapy and prevention. Nat Med 7:548-52. 31. Zwick E, Bange J, Ullrich A (2001). Receptor tyrosine kinase signaling as a target for cancer intervention strategies. Endocrine-Related Cancer 8: 161-173. 32. Slamon D. J., G. M. Clark, S. G. Wong et al. (1987). Human breast cancer: Correlation of relapse and survival with amplification of the HER-2/neu oncogene. Science, 235: 177-181. 33. Slamon D. J., W. Godolphin, L. A. Jones, J. A. Holt, S. G. Wong, D. E. Keith, W. J. Levin, S. G. Stuart, J. Udove, A. Ullrich and M. F. Press (1989). Studies of the HER-2/neu proto-oncogene in human breast and ovarian cancer. Science, 244: 707-711. 34. Wright C., B. Angus, S, Nicholson et al. (1989). Expression of c-erbB-2 oncoprotein: a prognostic indicator in human breast cancer. Cancer Res., 49: 2087-2094. 35. Nicholson S., C. Wright, J. R. C. Sainsbury, P. Halcrow, P. Kelly, B. Angus, J. R. Famdon and A. L. Harris (1990). Epidermal growth factor receptor as a marker for poor prognosis in node-negative breast cancer patients: neu and tamoxifen failure. J. Steroid Biochem., 37: 811-818. 36. Benz C., G. Scott, J. Sarup, R. Johnson, D. Tripathy, E. Coronado, H. Shepard and C. Osborne (1993). Estrogen-dependent, tamoxifen-resistant tumorigenic growth of MCF-7 cells transfected with HER2/neu. Breast Cancer Res. Treatment, 24: 85-92. 37. Pegram, M., G. Pauletti and D. Slamon (1998). Her-2/neu as a predictive marker of response to breast cancer therapy. Brst. Cancer Res. Trtmt., 52: 65-77. 38. Lipton A, Ali S M, Leitzel K, Demers L, Chinchilli V, Engle L, Harvey H A, Brady C, Nalin C M, Dugan M, Carney W, Allard J (2002). Elevated serum Her-2/neu level predicts decreased response to hormone therapy in metastatic breast cancer. J Clin Oncol. 20:1467-72. 39. Green, S, and P. Chambon (1988). Nuclear receptors enhance our understanding of transcription regulation. Trends Genet., 4: 309-314. 40. Gruber C J, W Tschugguel, C Schneeberger and J C Huber (2002). Mechanisms of disease: Production and actions of estrogens. New Engl J Med 346: 340-352. 41. Stoica G, Franke T, Wellstein A, Czubayko F, List H-J, Reiter R, Morgan E, Martin M, Stoica A (2003). Estradiol rapidly activates Akt via the erbB2 signaling pathway. Mol. Endocrinol. 17:818-830. 42. Katzenellenbogen B S (1996). Estrogen receptors: bioactivities and interactions with cell signaling pathways. Biol Reprod. 54: 287-93. 43. Wakeling A, Nicholson R, Gee J (2001). Prospects for combining hormonal and non-hormonal growth factor inhibition. Clin. Cancer Res. 7: 4350s-4355s. 44. Pietras, R. and Szego C. (1977). Specific binding sites for oestrogen at the outer surfaces of isolated endometrial cells. Nature, 265:69-72. 45. Levin E (1999). Cellular functions of the plasma membrane estrogen receptor. Trends Endocrinol. Metabol. 10: 374-377. 46. Marquez D, Pietras R J (2003). Membrane-associated estrogen receptors and breast cancer. In: "The Identities of Membrane Steroid Receptors" (Watson C S, editor), Kluwer Academic Publ.: pp. 1-10. 47. Simons K, van Meer G. (1988). Lipid sorting in epithelial cells. Biochemistry 27: 6197-202. 48. Anderson R G (1998). The caveolae membrane system. Annu Rev Biochem 67:199-225. 49. Song K S, Shengwen L, Okamoto T et al. (1996). Co-purification and direct interaction of ras with caveolin, an integral membrane protein of caveolae microdomains. J. Biol. Chem. 271: 9690-9697. 50. Koleske A J, Baltimore D, $L^0$ isanti M P (1995). Reduction of caveolin and caveolae in oncogenically transformed cells. Proc Natl Acad Sci USA 92: 1381-5. 51. Pietras R. J. and C. M. Szego (1984). Specific internalization of estrogen and binding to nuclear matrix in isolated uterine cells. Biochem. Biophys. Res. Commun., 123: 84-90. 52. Chambliss K, Yuhanna I, Mineo C, et al. (2000). Estrogen receptor alpha and endothelial nitric oxide synthase are organized into a functional signaling module in caveolae. Circ Res. 87: E44-E52. 53. Font de Mora J, Brown M (2000). AIB 1 is a conduit for kinase-mediated growth factor signaling to the estrogen receptor. Mol Cell Biol 20: 5041-7. 54. Katzenellenbogen B S, Montano M M, Ekena K et al. (1997). Antiestrogens: mechanisms of action and resistance in breast cancer. Breast Cancer Res Treat 44: 23-38. 55. Konecny G, Pauletti G, Pegram M, et al. (2003). Quantitative association between HER-2 and steroid hormone receptors in hormone receptor-positive primary breast cancer. J Natl Cancer Inst. 95:142-153. 56. Wright C., S, Nicholson, B. Angus, J. R. Sainsbury, J. Famdon, J. Cairns, A. L. Harris and C. H. Home (1992). Relationship between c-erbB-2 protein product expression and response to endocrine therapy in advanced breast cancer. Br. J. Cancer, 65: 118-124. 57. Borg A., B. Baldetorp, M. Femo, et al. (1994). ErbB2 amplification is associated with tamoxifen resistance in steroid-receptor positive breast cancer. Cancer Letters, 81:137-143. 58. Leitzel K., Y. Teramoto, K. Konrad, et al. (1995). Elevated serum c-erbB-2 antigen levels and decreased response to hormone therapy of breast cancer. J. Clin. Oncol., 13: 1129-1135. 59. De Laurentis M, Arpino G, Massarelli E, et al. (2000). A meta-analysis of the interaction between HER2 and the response to endocrine therapy in metastatic breast cancer. Am Soc Clin Oncol 19: 301. 60. Hu J C, Mokbel K (2001). Does c-erbB2/HER2 overexpression predict adjuvant tamoxifen failure in patients with early breast cancer? Eur J Surg Oncol 27: 335-7. 61. Pietras R J, Marquez D, Chen H-W, Ayala R, Ramos L, and Slamon D (2003). Improved antitumor therapy with Herceptin and Faslodex for dual targeting of HER-2 and estrogen receptor signaling pathways in human breast cancers with overexpression of HER-2/neu gene. Breast Cancer Res Trtmt 82, Suppl 1: 12-13. 62. Kalaitzidis D, Gilmore T D: Transcription factor cross-talk: the estrogen receptor and NF-kappaB. Trends Endocrinol Metab 2005, 16:46-52) 63. Biswas D K, Singh S, Shi Q, Pardee A B, Iglehart J D: Crossroads of estrogen receptor and NF-kappaB signaling. Sci STKE 2005, 288:pe27 64. Knowlden J, Hutcheson I, Jones H et al. (2003). Elevated levels of EGFR/c-erbB2 heterodimers mediate an autocrine growth regulatory pathway in tamoxifen-resistant MCF-7 cells. Endocrinology 144:1032-44. 65. Wu Y, C Ginther, J Kim, N Mosher, S Chung, D Slamon, and J Vadgama (2012). Expression of Wnt3 Activates Wnt/b-Catenin Pathway and Promotes EMT-like Phenotype in Trastuzumab-Resistant HER2-Overexpressing Breast Cancer Cells. Mol Cancer Res 2012; 10:1597-1606. 66. Massarweh S, Osborne C K, Creighton C et al. (2008). Tamoxifen resistance in breast tumors is driven by growth factor receptor signaling with repression of classic ER genomic function. Cancer Res 68:826-33. 67. Marquez D C, Chen H W, Welshons W V and Pietras R J (2006). Estrogen receptor in membrane lipid rafts and signal transduction in breast cancer. Molecular Cellular Endocrinol 246: 91-100. 68. Berstein L M, Yue W, Wang J P, Santen R J (2011). Isolated and combined action of tamoxifen and metformin in wild-type, tamoxifen-resistant, and estrogen-deprived MCF-7 cells. Breast Cancer Res Treat. 128:109-17. 69. Zhou Y, Yau C, Gray J W, Chew K, Dairkee S H, Moore D H, Eppenberger U, Eppenberger-Castori S, Benz C C (2007). Enhanced N F kappa B and AP-1 transcriptional activity associated with antiestrogen resistant breast cancer. BMC Cancer 7:59. 70. Malik F, Korkaya H, Clouthier S G, Wicha M S (2012). Lin28 and HER2: two stem cell regulators conspire to drive aggressive breast cancer. Cell Cycle 11:2780-1. 71. Darling T N, Pacheco-Rodriguez G, Gorio A, Lesma E, Walker C, Moss J (2010). Lymphangioleiomyomatosis and TSC2−/− cells. Lymphat Res Biol. 8(1):59-69. 72. McCormack F X, Inoue Y, Moss J, Singer L G, Strange C, Nakata K, Barker A F, Chapman J T, Brantly M L, Stocks J M, Brown K K, Lynch J P 3rd, Goldberg H J, Young L R, Kinder B W, Downey G P, Sullivan E J, Colby T V, McKay R T, Cohen M M, Korbee L, Taveira-DaSilva A M, Lee H S, Krischer J P, Trapnell B C; National Institutes of Health Rare Lung Diseases Consortium; MILES Trial Group. Efficacy and safety of sirolimus in lymphangioleiomyomatosis (2011). N Engl J Med 364(17):1595-606. Epub 2011 Mar. 16. 73. Darling T N, Pacheco-Rodriguez G, Gorio A, Lesma E, Walker C, Moss J (2010). Lymphangioleiomyomatosis and TSC2−/− cells. Lymphat Res Biol. 8(1):59-69. 74. Astrinidis A, Timothy P Cash, Deborah S Hunter, Cheryl L Walker, Jonathan Chernoff and Elizabeth P Henske (2002). Tuberin, the tuberous sclerosis complex 2 tumor suppressor gene product, regulates Rho activation, cell adhesion and migration. Oncogene 21: 8470-8476. 75. Howe S R, Gottardis M M, Everitt J I, Goldsworthy T L, Wolf D C, Walker C (1995). Rodent model of reproductive tract leiomyomata: establishment and characterization of tumor-derived cell lines. Am J Pathol 146:1568-79. 76. Yu J J, Robb V A, Morrison T A, Ariazi E A, Karbowniczek M, Astrinidis A, Wang C, Hernandez-Cuebas L, Seeholzer L F, Nicolas E, Hensley H, Jordan V C, Walker C L, Henske E P (2009). Estrogen promotes the survival and pulmonary metastasis of tuberin-null cells. Proc Natl Acad Sci USA 106(8):2635-40. Epub 2009 Feb. 6. 77. Arbiser J L, Yeung R, Weiss S W, Arbiser Z K, Amin M B, Cohen C, Frank D, Mahajan S, Herron G S, Yang J, Onda H, Zhang H B, Bai X, Uhlmann E, Loehr A, Northrup H, Au P, Davis I, Fisher D E, and Gutmann D H. The generation and characterization of a cell line derived from a sporadic renal angiomyolipoma: use of telomerase to obtain stable populations of cells from benign neoplasms. Am J Pathol 159: 483-491, 2001. 78. Yu J, Astrinidis A, Howard S, Henske E P. Estradiol and tamoxifen stimulate LAM-associated angiomyolipoma cell growth and activate both genomic and nongenomic signaling pathways. Am J Physiol Lung Cell Mol. Physiol. 2004 April; 286 (4):L694-700. Epub 2003 Aug. 15.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A compound, or a pharmaceutically acceptable salt thereof, wherein the compound is

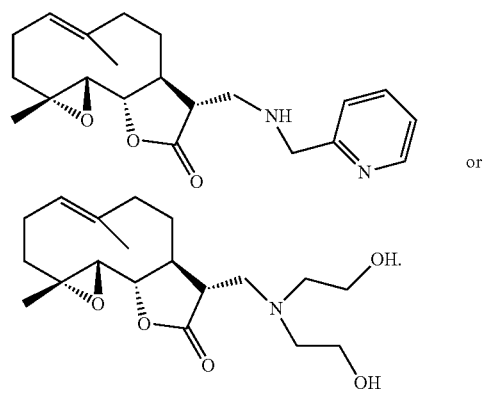

or

2. A pharmaceutical composition comprising a pharmaceutically acceptable excipient and a compound, or pharmaceutically acceptable salt thereof, of claim 1.

3. The pharmaceutical composition of claim 2, comprising a second agent wherein said second agent is an anti-cancer agent.

* * * * *